US012249413B2

(12) United States Patent
Foley et al.

(10) Patent No.: US 12,249,413 B2
(45) Date of Patent: Mar. 11, 2025

(54) EXERCISE SYSTEM AND METHOD

(71) Applicant: PELOTON INTERACTIVE, INC., New York, NY (US)

(72) Inventors: John Paul Foley, New York, NY (US); Hans Schlichting Woolley, West Hollywood, CA (US); Jason Poure, Hastings on Hudson, NY (US); Joseph Intonato, Brooklyn, NY (US)

(73) Assignee: PELOTON INTERACTIVE, INC., New York, NY (US)

( * ) Notice: Subject to any disclaimer, the term of this patent is extended or adjusted under 35 U.S.C. 154(b) by 0 days.

(21) Appl. No.: 18/586,390

(22) Filed: Feb. 23, 2024

(65) Prior Publication Data

US 2024/0203559 A1 Jun. 20, 2024

Related U.S. Application Data

(63) Continuation of application No. 18/186,846, filed on Mar. 20, 2023, now Pat. No. 11,915,817, which is a (Continued)

(51) Int. Cl.
*G16H 20/30* (2018.01)
*A63B 21/005* (2006.01)
(Continued)

(52) U.S. Cl.
CPC ........... *G16H 20/30* (2018.01); *A63B 21/015* (2013.01); *A63B 22/06* (2013.01);
(Continued)

(58) Field of Classification Search
CPC ........ G16H 20/30; G16H 15/00; G16H 20/10; A63B 21/015; A63B 22/06;
(Continued)

(56) References Cited

U.S. PATENT DOCUMENTS 32,345 A * 5/1861 Bartholow ................ F42B 5/18
102/431
219,059 A * 9/1879 Anders .................. G10K 1/063
379/418
(Continued)

FOREIGN PATENT DOCUMENTS

CN 2877780 Y 3/2007
CN 101766891 7/2010
(Continued)

OTHER PUBLICATIONS

US 8,092,344 B2, 01/2012, Tagliabue (withdrawn)
(Continued)

*Primary Examiner* — Garrett K Atkinson
(74) *Attorney, Agent, or Firm* — Haynes and Boone, LLP

(57) ABSTRACT

A method for displaying archived exercise classes comprising displaying information about archived exercise classes that can be accessed by a first user via a computer network on a display screen at a first location, wherein the first user can select among a plurality of archived classes, outputting digital video and audio content comprising the selected archived class, detecting a performance parameter for the first user at a particular point in the selected class, displaying the performance parameter on the display screen, and displaying performance parameters from a second user at a second location on the display screen such that at least one of the performance parameters from the first user and at least one of the performance parameters from the second user at the same point in the class are presented for comparison.

20 Claims, 17 Drawing Sheets

Related U.S. Application Data continuation of application No. 17/709,169, filed on Mar. 30, 2022, now Pat. No. 11,610,664, which is a continuation of application No. 17/492,522, filed on Oct. 1, 2021, now Pat. No. 11,295,849, which is a continuation of application No. 17/220,876, filed on Apr. 1, 2021, now Pat. No. 11,139,061, which is a continuation of application No. 16/902,195, filed on Jun. 15, 2020, now Pat. No. 11,081,224, which is a continuation of application No. 16/866,499, filed on May 4, 2020, now Pat. No. 11,183,288, which is a continuation of application No. 16/666,332, filed on Oct. 28, 2019, now Pat. No. 10,639,521, which is a continuation of application No. 16/412,327, filed on May 14, 2019, now Pat. No. 10,486,026, which is a continuation of application No. 16/036,894, filed on Jul. 16, 2018, now Pat. No. 10,322,315, which is a continuation of application No. 15/865,206, filed on Jan. 8, 2018, now Pat. No. 10,022,590, which is a continuation of application No. 14/992,032, filed on Jan. 11, 2016, now Pat. No. 9,861,855, which is a continuation of application No. 14/930,398, filed on Nov. 2, 2015, now Pat. No. 9,233,276, which is a continuation of application No. 13/956,087, filed on Jul. 31, 2013, now Pat. No. 9,174,085, said application No. 17/709,169 is a continuation-in-part of application No. 17/120,928, filed on Dec. 14, 2020, now Pat. No. 11,400,344, which is a continuation of application No. 15/686,875, filed on Aug. 25, 2017, now Pat. No. 10,864,406.

(60) Provisional application No. 61/677,985, filed on Jul. 31, 2012, provisional application No. 61/798,342, filed on Mar. 15, 2013, provisional application No. 62/380,412, filed on Aug. 27, 2016.

(51) Int. Cl.
| | |
|---|---|
| *A63B 21/015* | (2006.01) |
| *A63B 21/22* | (2006.01) |
| *A63B 22/06* | (2006.01) |
| *A63B 24/00* | (2006.01) |
| *A63B 71/06* | (2006.01) |
| *A63F 13/798* | (2014.01) |
| *G09B 5/10* | (2006.01) |
| *G09B 5/14* | (2006.01) |
| *G16H 15/00* | (2018.01) |
| *G16H 20/10* | (2018.01) |
| *G16Z 99/00* | (2019.01) |

(52) U.S. Cl.
CPC ...... *A63B 22/0605* (2013.01); *A63B 24/0062* (2013.01); *A63B 24/0075* (2013.01); *A63B 24/0084* (2013.01); *A63B 71/0622* (2013.01); *A63F 13/798* (2014.09); *G09B 5/10* (2013.01); *G09B 5/14* (2013.01); *G16H 15/00* (2018.01); *G16H 20/10* (2018.01); *G16Z 99/00* (2019.02); *A63B 21/0051* (2013.01); *A63B 21/225* (2013.01); *A63B 2022/0658* (2013.01); *A63B 2024/0065* (2013.01); *A63B 2024/0068* (2013.01); *A63B 2024/0081* (2013.01); *A63B 2024/0096* (2013.01); *A63B 2071/0658* (2013.01); *A63B 2220/17* (2013.01); *A63B 2220/34* (2013.01); *A63B 2220/58* (2013.01); *A63B 2220/806* (2013.01); *A63B 2225/107* (2013.01); *A63B 2225/20* (2013.01); *A63B 2225/50* (2013.01); *A63B 2230/06* (2013.01); *A63B 2230/40* (2013.01); *A63B 2230/75* (2013.01)

(58) Field of Classification Search
CPC ............ A63B 22/0605; A63B 24/0062; A63B 24/0075; A63B 24/0084; A63B 71/0622; A63B 21/0051; A63B 21/225; A63B 2022/0658; A63B 2024/0065; A63B 2024/0068; A63B 2024/0081; A63B 2024/0096; A63B 2071/0658; A63B 2220/17; A63B 2220/34; A63B 2220/58; A63B 2220/806; A63B 2225/107; A63B 2225/20; A63B 2225/50; A63B 2230/06; A63B 2230/40; A63B 2230/75; A63F 13/798; G09B 5/10; G09B 5/14; G16Z 99/00

See application file for complete search history.

(56) References Cited

U.S. PATENT DOCUMENTS

| | | | |
|---|---|---|---|
| 3,976,192 | A | 8/1976 | Muller |
| 4,452,897 | A | 6/1984 | Umezawa et al. |
| 4,591,147 | A | 5/1986 | Smith |
| 4,614,337 | A | 9/1986 | Schonenberger |
| 4,709,917 | A | 12/1987 | Yang |
| 4,844,451 | A | 7/1989 | Bersonnet et al. |
| D303,414 | S | 9/1989 | Armstrong et al. |
| 4,880,225 | A | 11/1989 | Lucas et al. |
| 4,932,650 | A | 6/1990 | Bingham et al. |
| 4,955,599 | A | 9/1990 | Bersonnet et al. |
| 4,971,316 | A | 11/1990 | Dalebout et al. |
| 4,981,294 | A | 1/1991 | Dalebout et al. |
| 5,000,444 | A | 3/1991 | Dalebout et al. |
| 5,014,980 | A | 5/1991 | Bersonnet et al. |
| 5,029,801 | A | 7/1991 | Dalebout |
| 5,089,960 | A | 2/1992 | Sweeney, Jr. |
| 5,104,120 | A * | 4/1992 | Watterson ............ A63B 22/025 482/7 |
| 5,149,312 | A | 9/1992 | Croft et al. |
| D330,399 | S | 10/1992 | Furline |
| 5,178,594 | A | 1/1993 | Wu |
| 5,203,826 | A | 4/1993 | Dalebout |
| 5,213,555 | A | 5/1993 | Hood et al. |
| 5,247,853 | A | 9/1993 | Dalebout |
| 5,259,611 | A | 11/1993 | Dalebout et al. |
| 5,336,145 | A | 8/1994 | Keiser |
| 5,441,468 | A | 8/1995 | Deckers et al. |
| 5,458,548 | A | 10/1995 | Crossing et al. |
| 5,462,503 | A | 10/1995 | Benjamin et al. |
| 5,466,200 | A | 11/1995 | Ulrich et al. |
| 5,512,025 | A | 4/1996 | Dalebout et al. |
| 5,527,245 | A | 6/1996 | Dalebout et al. |
| 5,529,553 | A | 6/1996 | Finlayson |
| 5,547,439 | A | 8/1996 | Rawls et al. |
| 5,591,104 | A | 1/1997 | Andrus |
| 5,591,106 | A | 1/1997 | Dalebout et al. |
| 5,595,556 | A | 1/1997 | Dalebout et al. |
| 5,645,509 | A | 7/1997 | Brewer et al. |
| 5,656,000 | A | 8/1997 | Russell |
| 5,662,557 | A | 9/1997 | Watterson et al. |
| 5,669,857 | A | 9/1997 | Watterson et al. |
| 5,672,140 | A | 9/1997 | Watterson et al. |
| 5,674,156 | A | 10/1997 | Watterson et al. |
| 5,674,453 | A | 10/1997 | Watterson et al. |
| 5,676,624 | A | 10/1997 | Watterson et al. |
| 5,683,332 | A | 11/1997 | Watterson et al. |
| 5,690,582 | A | 11/1997 | Ulrich et al. |
| 5,702,325 | A | 12/1997 | Watterson et al. |
| 5,704,879 | A | 1/1998 | Watterson et al. |
| 5,718,657 | A | 2/1998 | Dalebout et al. |
| 5,722,922 | A | 3/1998 | Watterson et al. |
| 5,743,833 | A | 4/1998 | Watterson et al. |
| 5,772,560 | A | 6/1998 | Watterson et al. |

(56) References Cited

U.S. PATENT DOCUMENTS

| | | | |
|---|---|---|---|
| 5,827,155 A | 10/1998 | Jensen et al. | |
| D403,313 S | 12/1998 | Peppel | |
| 5,860,893 A | 1/1999 | Watterson et al. | |
| 5,860,894 A | 1/1999 | Dalebout et al. | |
| 5,888,172 A | 3/1999 | Andrus et al. | |
| 5,890,995 A | 4/1999 | Bobick et al. | |
| 5,899,834 A | 5/1999 | Dalebout et al. | |
| 5,947,868 A * | 9/1999 | Dugan | A63F 13/211 |
| | | | 482/4 |
| 5,984,838 A | 11/1999 | Wang et al. | |
| 5,989,161 A | 11/1999 | Wang et al. | |
| RE36,574 E | 2/2000 | Hochstein et al. | |
| 6,033,347 A | 3/2000 | Dalebout et al. | |
| 6,042,514 A | 3/2000 | Abelbeck | |
| 6,050,924 A | 4/2000 | Shea | |
| 6,059,692 A | 5/2000 | Hickman | |
| 6,152,856 A | 11/2000 | Studor et al. | |
| 6,155,927 A | 12/2000 | Levasseur et al. | |
| 6,171,217 B1 | 1/2001 | Cutler | |
| 6,171,218 B1 | 1/2001 | Shea | |
| 6,231,482 B1 | 5/2001 | Thompson | |
| 6,280,362 B1 | 8/2001 | Dalebout et al. | |
| 6,283,896 B1 | 9/2001 | Grunfeld et al. | |
| 6,312,363 B1 | 11/2001 | Watterson et al. | |
| 6,350,218 B1 | 2/2002 | Dalebout et al. | |
| 6,409,633 B1 | 6/2002 | Abelbeck | |
| 6,458,060 B1 | 10/2002 | Watterson et al. | |
| 6,471,622 B1 | 10/2002 | Hammer et al. | |
| 6,569,063 B2 | 5/2003 | Chen | |
| 6,601,016 B1 | 7/2003 | Brown et al. | |
| 6,626,799 B2 | 9/2003 | Watterson et al. | |
| 6,626,803 B1 | 9/2003 | Oglesby | |
| 6,648,798 B2 | 11/2003 | Yoo | |
| 6,695,751 B1 | 2/2004 | Hsu | |
| 6,695,752 B2 | 2/2004 | Lee | |
| 6,702,719 B1 | 3/2004 | Brown et al. | |
| 6,730,002 B2 | 5/2004 | Hald et al. | |
| 6,749,536 B1 | 6/2004 | Cuskaden et al. | |
| 6,749,537 B1 | 6/2004 | Hickman | |
| 6,761,667 B1 | 7/2004 | Cutler et al. | |
| 6,764,430 B1 | 7/2004 | Fencel | |
| 6,808,472 B1 | 10/2004 | Hickman | |
| 6,830,541 B2 | 12/2004 | Wu | |
| 6,899,659 B2 | 5/2005 | Anderson et al. | |
| 6,902,513 B1 * | 6/2005 | McClure | A63B 24/0006 |
| | | | 482/4 |
| 6,918,858 B2 | 7/2005 | Watterson et al. | |
| 6,921,351 B1 | 7/2005 | Hickman et al. | |
| 6,923,746 B1 | 8/2005 | Skowronski et al. | |
| 6,974,404 B1 | 12/2005 | Watterson et al. | |
| 6,984,193 B2 | 1/2006 | Chen | |
| 6,997,852 B2 | 2/2006 | Watterson et al. | |
| 6,997,853 B1 | 2/2006 | Cuskaden et al. | |
| 7,004,888 B1 | 2/2006 | Weng | |
| 7,060,006 B1 | 6/2006 | Watterson et al. | |
| 7,060,008 B2 | 6/2006 | Watterson et al. | |
| 7,077,789 B1 | 7/2006 | Chen | |
| D532,063 S | 11/2006 | Kim et al. | |
| 7,153,241 B2 | 12/2006 | Wang | |
| 7,166,062 B1 | 1/2007 | Watterson et al. | |
| 7,166,064 B2 | 1/2007 | Watterson et al. | |
| 7,192,388 B2 | 3/2007 | Dalebout et al. | |
| 7,252,624 B2 | 8/2007 | Wu et al. | |
| 7,285,075 B2 | 10/2007 | Cutler et al. | |
| 7,455,620 B2 | 11/2008 | Frykman et al. | |
| 7,455,622 B2 | 11/2008 | Watterson et al. | |
| 7,465,257 B1 | 12/2008 | Morgan, Jr. | |
| 7,510,509 B2 | 3/2009 | Hickman | |
| 7,537,546 B2 | 5/2009 | Watterson et al. | |
| 7,537,549 B2 | 5/2009 | Nelson et al. | |
| 7,540,828 B2 | 6/2009 | Watterson et al. | |
| 7,549,947 B2 | 6/2009 | Hickman et al. | |
| 7,556,590 B2 | 7/2009 | Watterson et al. | |
| 7,562,761 B2 | 7/2009 | Tasma et al. | |
| 7,575,536 B1 | 8/2009 | Hickman | |
| 7,594,878 B1 | 9/2009 | Joannou | |
| 7,603,255 B2 | 10/2009 | Case, Jr. et al. | |
| 7,618,350 B2 | 11/2009 | Dalebout et al. | |
| 7,618,352 B1 | 11/2009 | Wei | |
| D606,599 S | 12/2009 | Brian et al. | |
| 7,625,315 B2 | 12/2009 | Hickman | |
| 7,628,730 B1 | 12/2009 | Watterson et al. | |
| 7,637,847 B1 | 12/2009 | Hickman | |
| 7,645,212 B2 | 1/2010 | Ashby et al. | |
| 7,645,213 B2 | 1/2010 | Watterson et al. | |
| 7,658,698 B2 | 2/2010 | Pacheco et al. | |
| 7,674,205 B2 | 3/2010 | Dalebout et al. | |
| 7,678,023 B1 | 3/2010 | Shea | |
| 7,713,171 B1 | 5/2010 | Hickman | |
| 7,713,172 B2 | 5/2010 | Watterson et al. | |
| 7,717,828 B2 | 5/2010 | Simonson et al. | |
| 7,736,272 B2 | 6/2010 | Martens | |
| 7,740,563 B2 | 6/2010 | Dalebout et al. | |
| 7,746,997 B2 * | 6/2010 | Brunson | G09B 5/06 |
| | | | 434/323 |
| 7,766,797 B2 | 8/2010 | Dalebout et al. | |
| 7,775,940 B2 | 8/2010 | Dalebout et al. | |
| 7,785,236 B1 | 8/2010 | Lo | |
| 7,789,800 B1 | 9/2010 | Watterson et al. | |
| 7,833,135 B2 | 11/2010 | Radow et al. | |
| 7,857,731 B2 | 12/2010 | Hickman et al. | |
| 7,862,478 B2 | 1/2011 | Watterson et al. | |
| 7,862,483 B2 | 1/2011 | Hendrickson et al. | |
| 7,874,957 B2 | 1/2011 | Hurwitz et al. | |
| 7,901,323 B2 | 3/2011 | Olason et al. | |
| 7,901,334 B2 | 3/2011 | Chen et al. | |
| 7,909,740 B2 | 3/2011 | Dalebout et al. | |
| 7,927,253 B2 * | 4/2011 | Vincent | H04B 1/385 |
| | | | 482/8 |
| 7,934,983 B1 | 5/2011 | Eisner | |
| 7,980,996 B2 | 7/2011 | Hickman | |
| 7,981,000 B2 | 7/2011 | Watterson et al. | |
| 8,001,472 B2 * | 8/2011 | Gilley | A63B 22/02 |
| | | | 715/834 |
| 8,012,067 B2 | 9/2011 | Joannou | |
| 8,021,270 B2 | 9/2011 | D'Eredita | |
| 8,029,415 B2 | 10/2011 | Ashby et al. | |
| 8,052,581 B1 | 11/2011 | Lohr et al. | |
| 8,068,858 B2 | 11/2011 | Werner et al. | |
| 8,298,123 B2 | 10/2012 | Hickman | |
| 8,348,813 B2 | 1/2013 | Huang | |
| 8,376,910 B2 * | 2/2013 | Cheung | G06F 3/048 |
| | | | 482/901 |
| 8,545,369 B2 * | 10/2013 | Cheung | A63B 71/0622 |
| | | | 482/8 |
| 8,579,767 B2 * | 11/2013 | Ellis | H04W 12/02 |
| | | | 482/901 |
| 8,585,561 B2 | 11/2013 | Watt et al. | |
| 8,608,624 B2 | 12/2013 | Shabodyash et al. | |
| 8,718,927 B2 | 5/2014 | Kitchel et al. | |
| 8,784,270 B2 | 7/2014 | Ashby et al. | |
| 8,829,376 B2 | 9/2014 | Wei | |
| 8,858,400 B2 | 10/2014 | Johnson | |
| 8,892,219 B2 | 11/2014 | Pryor | |
| 8,950,276 B2 | 2/2015 | Wu | |
| 8,986,169 B2 | 3/2015 | Bayerlein et al. | |
| 9,044,635 B2 | 6/2015 | Lull | |
| 9,116,922 B2 | 8/2015 | Shaw et al. | |
| 9,174,085 B2 * | 11/2015 | Foley | A63B 24/0084 |
| 9,233,276 B1 | 1/2016 | Foley et al. | |
| 9,364,712 B2 | 6/2016 | Wu | |
| 9,579,544 B2 | 2/2017 | Watterson | |
| 9,623,285 B1 * | 4/2017 | Ruiz | A61B 5/1122 |
| 9,636,567 B2 * | 5/2017 | Brammer | A63B 71/0622 |
| 9,649,528 B2 | 5/2017 | Hao | |
| 9,664,518 B2 | 5/2017 | Mach | |
| 9,808,672 B2 | 11/2017 | Dalebout | |
| 9,814,929 B2 | 11/2017 | Moser | |
| 9,861,855 B2 | 1/2018 | Foley et al. | |
| 10,009,644 B2 * | 6/2018 | Aimone | H04N 21/4307 |
| 10,022,590 B2 | 7/2018 | Foley et al. | |
| 10,322,315 B2 | 6/2019 | Foley et al. | |
| 10,486,026 B2 | 11/2019 | Foley et al. | |
| 2001/0004622 A1 | 6/2001 | Alessandri | |

(56) References Cited

U.S. PATENT DOCUMENTS

| | | |
|---|---|---|
| 2001/0053735 A1 | 12/2001 | Cohen et al. |
| 2002/0016235 A1 | 2/2002 | Ashby |
| 2002/0091627 A9 | 7/2002 | Yang |
| 2003/0064863 A1 | 4/2003 | Chen |
| 2003/0093248 A1* | 5/2003 | Vock .................... A42B 3/0433 |
| | | 702/188 |
| 2003/0166437 A1 | 9/2003 | Ho |
| 2003/0171190 A1 | 9/2003 | Rice |
| 2003/0199366 A1* | 10/2003 | Anderson .......... A63B 22/0242 |
| | | 482/54 |
| 2004/0102931 A1* | 5/2004 | Ellis ...................... H04W 4/029 |
| | | 702/188 |
| 2004/0121884 A1 | 6/2004 | Chang |
| 2004/0166995 A1 | 8/2004 | Wu |
| 2004/0224741 A1 | 11/2004 | Jen et al. |
| 2005/0020410 A1 | 1/2005 | Chang |
| 2005/0054490 A1 | 3/2005 | Chou |
| 2005/0137062 A1 | 6/2005 | Kuokkanen |
| 2005/0239601 A1 | 10/2005 | Thomas |
| 2006/0058160 A1 | 3/2006 | Lee |
| 2006/0136173 A1* | 6/2006 | Case, Jr. ............. A63B 24/0003 |
| | | 702/182 |
| 2006/0183602 A1 | 8/2006 | Astilean |
| 2006/0184427 A1 | 8/2006 | Singh |
| 2006/0205566 A1 | 9/2006 | Watterson et al. |
| 2006/0207867 A1 | 9/2006 | Waddington |
| 2007/0005395 A1 | 1/2007 | Singh |
| 2007/0011027 A1 | 1/2007 | Melendez |
| 2007/0032345 A1* | 2/2007 | Padmanabhan ........ A63B 24/00 |
| | | 482/8 |
| 2007/0072743 A1 | 3/2007 | Severino et al. |
| 2007/0073592 A1 | 3/2007 | Perry |
| 2007/0116207 A1* | 5/2007 | Brunson .................. G09B 7/02 |
| | | 379/90.01 |
| 2007/0117081 A1 | 5/2007 | Ford |
| 2007/0197345 A1 | 8/2007 | Wallace et al. |
| 2007/0219057 A1 | 9/2007 | Fleishman |
| 2007/0219059 A1* | 9/2007 | Schwartz ........... A61B 5/02405 |
| | | 482/8 |
| 2007/0232452 A1 | 10/2007 | Hanoun |
| 2007/0254778 A1 | 11/2007 | Ashby |
| 2007/0281831 A1 | 12/2007 | Wang |
| 2008/0015089 A1 | 1/2008 | Hurwitz et al. |
| 2008/0051256 A1 | 2/2008 | Ashby et al. |
| 2008/0076637 A1* | 3/2008 | Gilley ................. G06Q 30/0201 |
| | | 482/9 |
| 2008/0086318 A1* | 4/2008 | Gilley .................... G16H 10/20 |
| | | 705/319 |
| 2008/0096725 A1 | 4/2008 | Keiser |
| 2008/0096726 A1 | 4/2008 | Riley et al. |
| 2008/0116036 A1 | 5/2008 | Tasma et al. |
| 2008/0125288 A1 | 5/2008 | Case |
| 2008/0161733 A1 | 7/2008 | Einav et al. |
| 2008/0242514 A1 | 10/2008 | Piccionelli et al. |
| 2008/0300110 A1 | 12/2008 | Smith et al. |
| 2009/0011907 A1 | 1/2009 | Radow et al. |
| 2009/0098524 A1* | 4/2009 | Walton .................... G09B 5/14 |
| | | 434/350 |
| 2009/0098980 A1 | 4/2009 | Waters |
| 2009/0227429 A1 | 9/2009 | Baudhuin |
| 2009/0233769 A1 | 9/2009 | Pryor |
| 2009/0233771 A1* | 9/2009 | Quatrochi .......... A63B 71/0622 |
| | | 434/247 |
| 2009/0258758 A1 | 10/2009 | Hickman et al. |
| 2009/0291805 A1 | 11/2009 | Blum et al. |
| 2010/0009810 A1 | 1/2010 | Trzecieski |
| 2010/0022354 A1 | 1/2010 | Fisher |
| 2010/0029386 A1 | 2/2010 | Pitsch |
| 2010/0035726 A1 | 2/2010 | Fisher et al. |
| 2010/0048358 A1* | 2/2010 | Tchao .................... G06F 3/016 |
| | | 482/8 |
| 2010/0062818 A1 | 3/2010 | Haughay, Jr. et al. |
| 2010/0156625 A1 | 6/2010 | Ruha |
| 2010/0160115 A1 | 6/2010 | Morris |
| 2010/0197460 A1 | 8/2010 | Czarnecki |
| 2010/0197461 A1 | 8/2010 | Czarnecki |
| 2010/0234185 A1 | 9/2010 | Watt et al. |
| 2010/0279823 A1 | 11/2010 | Waters |
| 2011/0071003 A1 | 3/2011 | Watterson et al. |
| 2011/0082008 A1* | 4/2011 | Cheung ............. A63B 71/0622 |
| | | 482/8 |
| 2011/0082011 A1 | 4/2011 | Ellis |
| 2011/0086707 A1 | 4/2011 | Loveland |
| 2011/0172059 A1 | 7/2011 | Watterson et al. |
| 2011/0172060 A1* | 7/2011 | Morales ............. A63B 69/0053 |
| | | 482/8 |
| 2011/0190097 A1 | 8/2011 | Daly et al. |
| 2011/0224999 A1 | 9/2011 | Baccarella-garcia |
| 2011/0098156 A1 | 12/2011 | Ng et al. |
| 2011/0300917 A1 | 12/2011 | Hill |
| 2011/0306911 A1 | 12/2011 | Tran |
| 2011/0319229 A1 | 12/2011 | Corbalis et al. |
| 2012/0023191 A1 | 1/2012 | Kang et al. |
| 2012/0088633 A1 | 4/2012 | Crafton |
| 2012/0108394 A1 | 5/2012 | Jones |
| 2012/0162351 A1 | 6/2012 | Feldman et al. |
| 2012/0277891 A1 | 11/2012 | Aragones et al. |
| 2012/0283855 A1 | 11/2012 | Hoffman |
| 2013/0125025 A1* | 5/2013 | Cheung .................. G06F 3/048 |
| | | 715/753 |
| 2013/0135115 A1 | 5/2013 | Johnson et al. |
| 2013/0159928 A1 | 6/2013 | Joynes et al. |
| 2013/0222597 A1 | 8/2013 | Brink et al. |
| 2013/0237374 A1* | 9/2013 | Ashby ................. A63B 71/0054 |
| | | 482/4 |
| 2013/0281241 A1 | 10/2013 | Watterson et al. |
| 2014/0082526 A1 | 3/2014 | Park et al. |
| 2014/0172135 A1* | 6/2014 | Eisner ...................... A63K 3/00 |
| | | 700/91 |
| 2014/0223462 A1* | 8/2014 | Aimone ................. G16H 40/67 |
| | | 725/10 |
| 2015/0182800 A1* | 7/2015 | Watterson ............. A63B 22/02 |
| | | 482/4 |
| 2015/0238817 A1 | 8/2015 | Watterson et al. |
| 2015/0273272 A1 | 10/2015 | Wang |
| 2015/0350861 A1 | 12/2015 | Soli et al. |
| 2017/0123390 A1 | 5/2017 | Barco et al. |
| 2017/0186444 A1* | 6/2017 | Lu ........................... G10L 15/08 |
| 2017/0281079 A1* | 10/2017 | Nachman ............... A63B 22/02 |
| 2018/0056132 A1 | 3/2018 | Foley et al. |
| 2018/0126248 A1* | 5/2018 | Dion ......................... A63B 1/00 |
| 2018/0126249 A1* | 5/2018 | Consiglio .......... A63B 22/0023 |
| 2018/0140903 A1* | 5/2018 | Poure ................. A63B 23/1227 |
| 2020/0015736 A1* | 1/2020 | Alhathal .................. A61B 5/11 |

FOREIGN PATENT DOCUMENTS

| | | |
|---|---|---|
| EP | 0919259 | 6/1999 |
| WO | WO 1997/041925 | 11/1997 |
| WO | WO 2005/087323 | 9/2005 |

OTHER PUBLICATIONS

"NetAthlon 2XF Software, WebRacing Component of NetAthlon 2XF Software and/or WebRacer Bike incorporating NetAthlon Software", Software on sale at http://www.webracingstore.com/index.php/netathlon.html, Publication date is unknown, [retrieved on Apr. 1, 2019], Retrieved from the internet: <URL: https://web.archive.org/web/20110418014442/http://www.instyleaerobiking.co.uk:80/catalog/index.php?main_page=index&cPath=66>, 1 page.

"NetAthlon Version 2XF", Cycling 2XF User Guide, Publication date is unknown, [retrieved on Apr. 1, 2019], Retrieved from the internet: <URL: https://web.archive.org/web/20110313210842/http://www.webracing.org/trail_downloads/NA%202XF%20for%20Cycling%202.2.pdf>, 40 pages.

Instylefitness, "Instyle Fitness WebRacer Bike", Published on Mar. 15, 2011, [retrieved on Apr. 1, 2019], Retrieved from the internet: <URL: https://youtu.be/bWFtxEuZUZY>, 2 pages.

(56) References Cited

OTHER PUBLICATIONS

"Virtual Reality Fitness Experience", Publication date is unknown, [retrieved on Apr. 1, 2019], Retrieved from the internet: <URL: https://web.archive.org/web/20110424065356/http://www.webracing.org/index.htm>, 1 page.
"Commercial Products", Fitness Is Evolving, A revolution is taking place in our gym culture, Publication date is unknown, [retrieved on Apr. 1, 2019], Retrieved from the internet: <URL: https://web.archive.org/web/20110424050520/http://www.webracing.org/commercial.htm>, 1 page.
"Turn your fitness equipment into a fitness experience", RA Sports, Publication date is unknown, [retrieved on Apr. 1, 2019], Retrieved from the internet: <URL: https://web.archive.org/web/20110113140506/http://www.riderunrow.com/index.htm>, 1 page.
"Fitness Machines Compatibility", NetAthlon® Compatible Fitness Equipments,WebRacing, Inc., Publication date is unknown, [retrieved on Apr. 1, 2019], Retrieved from the internet: <URL: https://web.archive.org/web/20110123111916/http://www.riderunrow.com/fitness_machines.htm>, 1 page.
"NetAthlon® 2XF Virtual Interactive Fitness Software for Cycling", NetAthlon® Products, WebRacing, Inc., Publication date is unknown, [retrieved on Apr. 1, 2019], Retrieved from the internet: <URL: https://web.archive.org/web/20110113140511/http://www.riderunrow.com/products_na2.htm>, 3 pages.
"Turn Any Bike Trainer, ExerciseBike, Treadmill, or Rowing Machine into a Virtual Reality Experiencefor home and club use.", PEAK Virtual Indoor Training System, WebRacing, Inc., Publication date is unknown, [retrieved on Apr. 1, 2019], Retrieved from the internet: <URL: https://web.archive.org/web/20110113142318/http://www.riderunrow.com/products_sensors.htm>, 2 pages.
"WebRacing®", WebRacing, Inc., Publication date is unknown, [retrieved on Apr. 1, 2019], Retrieved from the internet: <URL: https://web.archive.org/web/20110503225914/http://riderunrow.com/products_webracing.htm>, 2 pages.
"Peak Sensor Kit Installation and User's Guide", Model ITS-2, WebRacing™ Ltd., Publication date is unknown, [retrieved on Apr. 1, 2019], Retrieved from the internet: <URL: https://web.archive.org/web/20120816050742/http://www.riderunrow.com/pdf/CYCLEFXSens orGuide.pdf>, 18 pages.
"Expresso S3 Bike and Expresso Live service", On sale by various dealers, Publication date is unknown, [retrieved on Apr. 1, 2019], Retrieved from the internet: <URL: https://web.archive.org/web/20101101203035/http://www.ifholdings.com/buy_now/dealers.htm>, 2 pages.
"Expresso S3 Novo", Publication date is unknown, [retrieved on Apr. 1, 2019], Retrieved from the internet: <URL: https://web.archive.org/web/20110713004606/http://www.ifholdings.com/index.htm>, 1 page.
"Ride on Expresso Biles", Publication date is unknown, [retrieved on Apr. 1, 2019], Retrieved from the internet: <URL: https://web.archive.org/web/20110111201822/http://www.expresso.net/UserPortal/welcome.do>, 1 page.
"Rider Experience", Publication date is unknown, [retrieved on Apr. 1, 2019], Retrieved from the internet: <URL: https://web.archive.org/web/20111001031535/http://ifholdings.com/experience/index.html>, 1 page.
"Expresso Rider Experience", Publication date is unknown, [retrieved on Apr. 1, 2019], Retrieved from the internet: <URL: https://web.archive.org/web/20111001031358/http:/ifholdings.com/experience/rider_interactive_experience.html>, 3 pages.
"The Expresso Interactive Cardio System", Publication date is unknown, [retrieved on Apr. 1, 2019], Retrieved from the internet: <URL: https://web.archive.org/web/20120123205226/http://www.ifholdings.com/pdf/product_services/s3_novo_brochure_2011.pdf>, 4 pages.
"Expresso S3 Novo Products Specification", Publication date is unknown, [retrieved on Apr. 1, 2019], Retrieved from the internet: <URL: https://web.archive.org/web/20120402221412/http://www.ifholdings.com/pdf/product_services/s3_novo_el_spec.pdf>, 5 pages.

"Expresso Live!", Harnessing the Internet and social media for you, Publication date is unknown, [retrieved on Apr. 1, 2019], Retrieved from the internet: <URL: https://web.archive.org/web/20111005111028/http://ifholdings.com/pdf/product_services/expresso_live_bro.pdf>, 2 pages.
"Expresso S3 Upright Bike", User Guide, Publication date is unknown, [retrieved on Apr. 1, 2019], Retrieved from the internet: <URL: https://s3.amazonaws.com/docs.ifholdings.com/IFH_S3_UG.pdf>, 8 pages.
"Expresso Bikes, The Experience", Publication date is unknown, [retrieved on Apr. 1, 2019], Retrieved from the internet: <URL: http://www.ucfitness.pitt.edu/img/equip/cardio/exp_s3ur_bro_100808_web.pdf>, 2 pages.
Expressorussia, Expresso Interactive Exercise Bike, [retrieved on Apr. 1, 2019], Retrieved from the internet: <URL: https://www.youtube.com/watch?v=41tNF1AWuBU>, Nov. 14, 2012, 2 pages.
"Wayback Machine", Publication date is unknown, [retrieved on Apr. 1, 2019], Retrieved from the internet: <URL: https://web.archive.org/web/20110614001441/http://singularityhub.com/2010/12/06/video-game-exercisebikes-ride-onto-the-social-network/>, 4 pages.
Wattbike, On sale at http://wattbike.com/us/shop, Publication date is unknown, [retrieved on Apr. 1, 2019], Retrieved from the internet: <URL: http://wattbike.com/us/shop>, 3 pages.
Wattbike, Publication date is unknown, [retrieved on Apr. 1, 2019], Retrieved from the internet: <URL: https://web.archive.org/web/20110702220339/http://wattbike.com/uk/wattbike/>, 5 pages.
Wattbike, Publication date is unknown, [retrieved on Apr. 1, 2019], Retrieved from the internet: <URL: https://web.archive.org/web/20110604140446/http://wattbike.com/us/>, 3 pages.
Wattbike, Train Less, Ride Faster, Publication date is unknown, [retrieved on Apr. 1, 2019], Retrieved from the internet: <URL: https://web.archive.org/web/20110708052957/http://wattbike.com/assets/docs/wattbike_brochure.pdf>, 6 pages.
Wattbike, User Manual, Publication date is unknown, [retrieved on Apr. 1, 2019], Retrieved from the internet: <URL: https://web.archive.org/web/20140712065824/http://wattbike.com/assets/docs/wattbike_user_manual.pdf>, 32 pages.
Shaman Clown, "Wattbike Indoor Trainer", [retrieved on Apr. 1, 2019], Retrieved from the internet: <URL: https://www.youtube.com/watch?v=t0jmUpFdoRA>, Mar. 30, 2010, 2 pages.
STTu, "Wattbike computer racing", [retrieved on Apr. 1, 2019], Retrieved from the internet: <URL: https://www.youtube.com/watch?v=YMHGtbg-Qeg>, Sep. 26, 2011, 2 pages.
"An introduction to the Wattbike", Publication date is unknown, [retrieved on Apr. 1, 2019], Retrieved from the internet: <URL: https://web.archive.org/web/20110604140626/http://wattbike.com/us/wattbike>, 4 pages.
"Race Power Cycling", Publication date is unknown, [retrieved on Apr. 1, 2019], Retrieved from the internet: < URL: https://web.archive.org/web/20110926050934/http://wattbike.com/uk/wattbike/power_cycling_software/race_power_cycling>, 1 page.
"Fitness, Group Cycling and PT", Publication date is unknown, [retrieved on Apr. 1, 2019], Retrieved from the internet: <URL: https://web.archive.org/web/20110604140508/http://wattbike.com/us/gyms_and_schools/gyms>, 3 pages.
"Group Power Cycling", Publication date is unknown, [retrieved on Apr. 1, 2019], Retrieved from the internet: <URL: https://web.archive.org/web/20110926051143/http://wattbike.com/uk/wattbike/power_cycling_software/group_power_cycling>, 1 page.
"Expert Software", Publication date is unknown, [retrieved on Apr. 1, 2019], Retrieved from the internet: <URL: https://web.archive.org/web/20110901133907/http://wattbike.com/uk/wattbike/expert_software/>, 1 page.
Flywheel Sports, Inc.'s cycling classes offered in New York, Florida, and Illinois, Publication date is unknown, class Schedules retrieved on Apr. 1, 2019, Retrieved from the internet: <URL: https://www.flywheelsports.com/classes/stadium-cycling>, 4 pages.
Flywheel Stadium Cycling New York, Performance Metrics, 2012, pp. 1-2.
*Peloton Interactive, Inc.* v. *Flywheel Sports, Inc.*, 2-18-cv-00390 (TXED), "Motion to Dismiss Plaintiff's Amended Complaint for

(56) References Cited

OTHER PUBLICATIONS

Failure to State a Claim Pursuant to Federal Rule of Civil Procedure 12 (b)(6) filed by Flywheel Sport, Inc.", Filed on Dec. 3, 2018.
*Peloton Interactive, Inc.* v. *Flywheel Sports, Inc.*, 2-18-cv-00390 (TXED), "Response in Opposition re 23 Motion to Dismiss Plaintiff's Amended Complaint for Failure to State a Claim Pursuant to Federal Rule of Civil Procedure 12 (b)(6) filed by Peloton Interactive. Inc.", Filed on Dec. 24, 2018.
*Peloton Interactive, Inc.* v. *Flywheel Sports, Inc.*, 2-18-cv-00390 (TXED), "Reply to Reponses to Motion re 23 Motion to Dismiss Plaintiff's Amended Complaint for Failure to State a Claim Pursuant to Federal Rule of Civil Procedure 12 (b)(6) filed by Flywheel Sport, Inc.", Filed on Jan. 9, 2019.
*Peloton Interactive, Inc.* v. *Flywheel Sports, Inc.*, 2-18-cv-00390 (TXED), "Sur-Reply to Reply to Response to Motion re 23 Motion to Dismiss Plaintiff's Amended Complaint for Failure to State a Claim Pursuant to Federal Rule of Civil Procedure 12 (b)(6) filed by Peloton Interactive. Inc.", Filed on Jan. 23, 2019.
*Flywheel Sports, Inc* et al v. *Peloton Interactive, Inc.*, IPR2019-00295 (PTAB), "Patent Owner's Preliminary Response to Petition for Inter Partes Review and Exhibits", U.S. Pat. No. 9,233,276, filed on Mar. 6, 2019.
*Flywheel Sports, Inc* et al v. *Peloton Interactive, Inc.*, IPR2019-00295 (PTAB), "Reply to Patent Owner's Preliminary Response," U.S. Pat. No. 9,233,276, filed on Mar. 21, 2019.
*Flywheel Sports, Inc* et al v. *Peloton Interactive, Inc.*, IPR2019-00295 (PTAB), "Patent Owner's Sur-Reply to Petitioner's Reply to Preliminary Response to Petition from Inter Partes review", U.S. Pat. No. 9,233,276, filed on Mar. 27, 2019.
*Flywheel Sports, Inc* et al v. *Peloton Interactive, Inc.*, IPR2019-00294 (PTAB), "Patent Owner's Preliminary Response to Petition for Inter Partes Review and Exhibits", U.S. Pat. No. 9,174,085, filed on Mar. 6, 2019.
*Flywheel Sports, Inc* et al v. *Peloton Interactive, Inc.*, IPR2019-00294 (PTAB), "Reply to Patent Owner's Preliminary Response," U.S. Pat. No. 9,174,085, filed on Mar. 21, 2019.
*Flywheel Sports, Inc* et al v. *Peloton Interactive, Inc.*, IPR2019-00294 (PTAB), "Patent Owner's Sur-Reply to Petitioner's Reply to Preliminary Response to Petition from Inter Partes review", U.S. Pat. No. 9,174,085, filed on Mar. 27, 2019.
*Flywheel Sports, Inc* et al v. *Peloton Interactive, Inc.*, IPR2019-00295 (PTAB), "Trial Instituted Document", U.S. Pat. No. 9,233,276, filed on Jun. 5, 2019.
*Flywheel Sports, Inc* et al v. *Peloton Interactive, Inc.*, IPR2019-00295 (PTAB), "Patent Owner's Objections to Petitioner's Pre-Trial Evidence", U.S. Pat. No. 9,233,276, filed on Jun. 19, 2019.
*Flywheel Sports, Inc* et al v. *Peloton Interactive, Inc.*, IPR2019-00564 (PTAB), "Patent Owner's Preliminary Response to Petition for Inter Partes Review and Exhibits", U.S. Pat. No. 9,861,855, filed on May 8, 2019.
*Flywheel Sports, Inc* et al v. *Peloton Interactive, Inc.*, IPR2019-00564 (PTAB), "Reply to Patent Owner's Preliminary Response", U.S. Pat. No. 9,861,855, filed on May 22, 2019.
*Flywheel Sports, Inc* et al v. *Peloton Interactive, Inc.*, IPR2019-00564 (PTAB), "Patent Owner's Sur-reply to Petitioner's Reply to Preliminary Response to Petition for Inter Partes Review", U.S. Pat. No. 9,861,855, filed on May 28, 2019.
*Flywheel Sports, Inc* et al v. *Peloton Interactive, Inc.*, IPR2019-00564 (PTAB), "Trial Instituted Document", U.S. Pat. No. 9,861,855, filed on Jun. 5, 2019.
*Flywheel Sports, Inc* et al v. *Peloton Interactive, Inc.*, IPR2019-00564 (PTAB), "Patent Owner's Objections to Petitioner's Pre-Trial Evidence", U.S. Pat. No. 9,861,855, filed on Jun. 19, 2019.
*Flywheel Sports, Inc* et al v. *Peloton Interactive, Inc.*, IPR2019-00294 (PTAB), "Trial Instituted Document", U.S. Pat. No. 9,174,085, filed on Jun. 5, 2019.
*Flywheel Sports, Inc* et al v. *Peloton Interactive, Inc.*, IPR2019-00294 (PTAB), "Patent Owner's Objections to Petitioner's Pre-Trial Evidence", U.S. Pat. No. 9,174,085, filed on Jun. 19, 2019.
*Flywheel Sports, Inc* et al v. *Peloton Interactive, Inc.*, IPR2019-00295 (PTAB), "Petition for Inter Partes Review and Exhibits", U.S. Pat. No. 9,233,276, filed on Nov. 15, 2018.
*Flywheel Sports, Inc* et al v. *Peloton Interactive, Inc.*, IPR2019-00564 (PTAB), "Petition for Inter Partes Review and Exhibits", U.S. Pat. No. 9,861,855, filed on Jan. 17, 2019.
*Flywheel Sports, Inc* et al v. *Peloton Interactive, Inc.*, IPR2019-00294 (PTAB), "Petition for Inter Partes Review and Exhibits", U.S. Pat. No. 9,174,085, filed on Nov. 15, 2018.
*Peloton Interactive, Inc.* v. *Flywheel Sports, Inc.*, 2-18-cv-00390 (TXED), "Notice by Flywheel Sports, Inc. of Compliance of service of P.R. 3-3 and 3-4 Invalidity Contention Disclosures (Ginsberg Jeffrey)", Filed on Mar. 21, 2019.
*Peloton Interactive, Inc.* v. *Flywheel Sports, Inc.*, 2-18-cv-00390-RWS-RSP, "Amended Complaint for Patent Infringement" filed by Peloton Interactive, Inc., U.S. Pat. No. 9,174,085, filed on Nov. 19, 2018.
Alshammari et al., "An Investigation on the Identification of VoIP Traffic: Case study on Gtalk and Skype," Retrieved at <https://www.cs.dal.ca/sites/default/files/technical_reports/CS-2010-05.pdf> (cited at reference 1 in paper by same name in 2010 International Conference on Network and Service Management, Niagara Falls, ON, 2010, pp. 310-313, Retrieved at <http://ieeexplore.ieee.org/stamp/stamp.jsp?tp=&arnumber=569121 0&isnumber=5691186>).
Bonfiglio et al., "Detailed Analysis of Skype Traffic," in IEEE Transactions on Multimedia, vol. 11, No. 1, pp. 117-127, Jan. 2009, Retrieved at <http://ieeexplore.ieee.org/stamp/stamp.jsp?tp=&arnumber=471721 0&isnumber=4749480>.
Xu et al., "Video Telephony for End-consumers: Measurement Study of Google+, iChat, and Skype," Proceedings of the 2012 Internet Measurement Conference (IMC '12). Boston, Massachusetts, Nov. 14-16, 2012, pp. 371-384. DOI: https://doi.org/10.1145/2398776.2398816 , Retrieved at <https://dl.acm.org/citation.cfm?doid=2398776.2398816>.
Lu et al., "Measurement Study of Multi-party Video Conferencing," Networking 2010, Lecture Notes in Computer Science, vol. 6091, Springer, Berlin, Heidelberg, pp. 96-108, Retrieved at https://doi.org/10.1007/978-3-642-12963-6_8 , Retrieved at <https://link.springer.com/chapter/10.1007/978-3-642-12963-6_8>.
Leena Rao, "Skype Teams Up With Citrix To Bring GoToMeeting Web Conferencing To Business Offerings," TechCrunch, Mar. 1, 2011, Retrieved at <https://web.archive.org/web/20110305033430/http://techcrunch.co m:80/2011/03/01/skype-teams-up-with-citrix-to-bring-gotomeeting-web-conferencing-to-business-offerings/> (pp. 4-8 of Ex. 1036 (Butler Affidavit and Ex. A to Affidavit)).
Elizabeth Woyke, "Facebook, Google Battle To Be Video-Calling Home Base," www.forbes.com, Jul. 6, 2011 Retrieved at <https://web.archive.org/web/20141019021702/http://www.forbes.com/sites/elizabethwoyke/2011/07/06/facebook-google-battle-to-be-video-calling-home-base/> (pp. 9-11 of Ex. 1036 (Butler Affidavit and Ex. A to Affidavit)).
Megan Geuss, " Group Video Chat Showdown: Google Hangouts and AnyMeeting Come Out on Top," PCWorld, Nov. 7, 2011, Retrieved at <https://web.archive.org/web/20120928000621/http://www.pcworld.com:80/article/243238/group_video_chat_showdown_google_hangouts_and_anymeeting_come_out_on_top.html> and <https://web.archive.org/web/20120930044906/http://www.pcworld.com:80/article/243238/group_video_chat_showdown_google_hangouts_and_anymeeting_come_out_on_top.html?page=2> (pp. 12-25 of Ex. 1036 (Butler Affidavit and Ex. A to Affidavit)).
Catherine Saint Louis, In New York, a Rivalry Shifts into High Gear, The New York Times (Oct. 8, 2010), Retrieved at <https://web.archive.org/web/20101014044600/http://www.nytimes.com/2010/10/10/fashion/10Spin.html> and <https://web.archive.org/web/20101014073935/http://www.nytimes.com/2010/10/10/fashion/10Spin.html?pagewanted=2> (pp. 26-30 of Ex. 1036 (Butler Affidavit and Ex. A to Affidavit)).
"Soul Cycle vs. Flywheel: A comparison shop and spin," WellandGoodNYC.com (Feb. 22, 2010), Retrieved at https://web.archive.org/web/20161115223126/http://www.welland good.com:80/good-sweat/soul-cycle-vs-flywheel-a-comparison-shop-and-spin/ (pp. 31-36 of Ex. 1036 (Butler Affidavit and Ex. A to Affidavit)).

(56) References Cited

OTHER PUBLICATIONS

Lauren Glassberg, "Flatiron studio takes spin class up a notch," abclocal.go.com (Mar. 11, 2010), Retrieved at <https://web.archive.org/web/20100409054516/http://abclocal.go.com:80/wabc/story?section=news/local&id=7325608> (pp. 37-42 Ex. 1036 (Butler Affidavit and Ex. A to Affidavit)).
Nick Sortal, "Flywheel brings high-tech cycling to South Florida," Sun Sentinel.com (Apr. 16, 2011), Retrieved at <https://web.archive.org/web/20110423072458/http://articles.sun-sentinel.com/2011-04-16/health/fl-hk-flywheel-cycling-041711-20110415_1_stationary-cycling-flywheel-specific-bike> and <https://web.archive.org/web/20110423043400/http://articles.sun-sentinel.com:80/2011-04-16/health/fl-hk-flywheel-cycling-041711-20110415_1_stationary-cycling-flywheel-specific-bike/2> (pp. 43-44 of Ex. 1036 (Butler Affidavit and Ex. A to Affidavit).
Flywheel Website, Retrieved at <https://web.archive.org/web/20120529111518/http://www.flywheelsp orts.com/locations> (p. 45 of Ex. 1036 (Butler Affidavit and Ex. A to Affidavit)).
Katherine Rosman, "The Latest Spin in Studio Cycling: Anti-Sweat Bikes," Wall Street Journal (Oct. 18, 2011), Retrieved at <https://web.archive.org/web/20111221022728/http://online.wsj.com:80/article/SB20001424052970204346104576636910111184694.html> (pp. 46-48 of Ex. 1036 (Butler Affidavit and Ex. A to Affidavit).
"Adding some friendly competition to your class," ICI/PRO Indoor Cycling 2.0 (Nov. 9, 2011), Retrieved at <https://web.archive.org/web/20120916013819/https://www.indoorcycl einstructor.com/icipro-instructor-training/training-with-power/adding-some-friendly-competition-to-your-class/> (pp. 49-54 of Ex. 1036 (Butler Affidavit and Ex. A to Affidavit)).
Screen captures from Mirror/Mirror, Episode 24, Season 4, Segment 4 ("Flywheel Sports") The Live Well Network, Retrieved at <http://livewellnetwork.com/Mirror-Mirror/episodes/Flywheel-Sports/8577947>.
"Random House Compact Unabridged Dictionary," Special 2nd Edition, Random House, Inc., 1996.
"The American Heritage Dictionary of the English Language," 5th Edition, Houghton Mifflin Harcourt Publishing Co., 2011.
"The Random House Dictionary of the English Language," 2nd Edition, Random House, Inc., 1987.
"The Pocket Oxford American Dictionary of Current English," Oxford University Press, 2002.
2012 Flywheel publication, Retrieved at <http://web.archive.org/web/20120128121139/http://new-york.flywheelsports.com:80/performance-metrics> (pp. 56-57 of Ex. 1036 (Butler Affidavit and Ex. A to Affidavit)).
Flywheel Website, Retrieved at <http://web.archive.org/web/20120106083132/http://www.flywheelspo rts.com:80/locations>.
NetAthlon Manual, Retrieved at <https://web.archive.org/web/20100331050623/http://www.riderunrow.com:80/pdf/NA%201.0%20User%20Guide.PDF> (pp. 62-101 of Ex. 1036 (Butler Affidavit and Ex. A to Affidavit)).
Michel Marriott, "Your Shot, He Said, Distantly," The New York Times (Aug. 26, 2004), Retrieved at <https://web.archive.org/web/20130405063028/http://www.nytimes.com/2004/08/26/technology/your-shot-he-said-distantly.html> and <https://web.archive.org/web/20150528054454/http://www.nytimes.com/2004/08/26/technology/your-shot-he-said-distantly.html?pagewanted=2>.
Mueller et al., "The Design of Networked Exertion Games," JVRB—Journal of Virtual Reality and Broadcasting, 5(2008), No. 13, Retrieved at <https://www.jvrb.org/past-issues/5.2008/1617/5200813.pdf>.
*Flywheel Sports, Inc.* v. *Peloton Interactive, Inc.,* IPR2019-01411 (PTAB), U.S. Pat. No. 10,322,315, "Petition for Inter Partes Review", Filed on Aug. 9, 2019.
*Peloton Interactive, Inc.* v. *Flywheel Sports, Inc.,* Civil Action 2:18-cv-00390 (TXED), "Notice by Peloton Interactive, Inc. re 29 Response in Opposition to Motion, 38 Sur-Reply to Reply to Response to Motion, Notice of Supplemental Authority (Attachments: #1 Supplemental Authority) (Smith, Melissa)", Filed on Jul. 30, 2019.
*Peloton Interactive, Inc.* v. *Flywheel Sports, Inc.,* Civil Action 2:18-cv-00390 (TXED), "Order finding as moot 23 Motion to Dismiss Plaintiff's Amended Complaint for Failure to State a Claim Pursuant to Federal Rule of Civil Procedure 12(b)(6), signed by Magistrate Judge Roy S. Payne on Aug. 13, 2019. (nkl,)", Entered on Aug. 13, 2019.
*Peloton Interactive, Inc.* v. *Flywheel Sports, Inc.,* Civil Action 2:18-cv-00390 (TXED), "Memorandum Order—denying 62 Motion to Stay Pending Inter Partes Review Proceedings, Signed by Magistrate Judge Roy S. Payne on Aug. 14, 2019. (ch.)", Entered on Aug. 15, 2019.
*Peloton Interactive, Inc.* v. *Flywheel Sports, Inc.,* 2-18-cv-00390 (TXED), "Joint Claim Construction and Prehearing Statement by Peloton Interactive, Inc.", filed by Flywheel Sports, Inc., (Smith, Melissa) filed on Nov. 4, 2019.
*Peloton Interactive, Inc.* v. *Flywheel Sports, Inc.,* IPR2019-01411 (PTAB), "Patent Owner's Preliminary Response to Petition for Inter Partes Review", filed by Peloton Interactive, Inc., filed on Nov. 14, 2019.
*Peloton Interactive, Inc.* v. *Flywheel Sports, Inc.,* IPR2019-01411 (PTAB), "Patent Owner's Updated Exhibit List", filed by Peloton Interactive, Inc., filed on Nov. 14, 2019.
*Peloton Interactive, Inc.* v. *Flywheel Sports, Inc.,* IPR2019-01411 (PTAB), Transcript of Conference Call, filed on Nov. 22, 2019.
*Peloton Interactive, Inc.* v. *Flywheel Sports, Inc.,* 2-19-cv-00317 (TXED), "Motion to Dismiss Plaintiff's Complaint Under Federal Rule of Civil Procedure 12(b)(6) For Improper Claim Splitting" filed by Flywheel Sports, Inc., (Budwin, Joshua), filed on Nov. 22, 2019.
*Peloton Interactive, Inc.* v. *Flywheel Sports, Inc.,* 2-18-cv-00390 (TXED), "Claim Construction Brief filed by Peloton Interactive, Inc.", filed by Peloton Interactive, Inc., (Smith, Melissa), filed on Nov. 22, 2019.
*Peloton Interactive, Inc.* v. *Flywheel Sports, Inc.,* 2-19-cv-00317 (TXED), "Amended Complaint against Flywheel Sports, Inc., filed by Peloton Interactive, Inc.", filed by Peloton Interactive, Inc., (Smith, Melissa), filed on: Nov. 25, 2019.
*Flywheel Sports, Inc et al* v. *Peloton Interactive, Inc.,* IPR2019-00294 (PTAB), "Patent Owner's Updated Exhibit List", filed by Peloton Interactive, Inc., filed on Nov. 25, 2019.
*Flywheel Sports, Inc et al* v. *Peloton Interactive, Inc.,* IPR2019-01411 (PTAB), "Peloton's Motion for Permission to Request Correction of Inventorship", filed by Peloton Interactive, Inc., filed on Nov. 26, 2019.
*Flywheel Sports, Inc et al* v. *Peloton Interactive, Inc.,* IPR2019-00294 (PTAB), "Peloton's Motion for Permission to Request Correction of Inventorship", filed by Peloton Interactive, Inc., filed on Nov. 26, 2019.
*Flywheel Sports, Inc et al* v. *Peloton Interactive, Inc.,* IPR2019-00295 (PTAB), "Peloton's Motion for Permission to Request Correction of Inventorship", filed by Peloton Interactive, Inc., filed on Nov. 26, 2019.
*Flywheel Sports, Inc et al* v. *Peloton Interactive, Inc.,* IPR2019-00564 (PTAB)," Peloton's Motion for Permission to Request Correction of Inventorship", filed by Peloton Interactive, Inc., filed on Nov. 26, 2019.
*Flywheel Sports, Inc et al* v. *Peloton Interactive, Inc.,* IPR2019-00294 (PTAB), "Petitioner's Reply to PO Response (Public Redacted)", filed by Flywheel Sports, Inc., filed on Nov. 27, 2019.
*Flywheel Sports, Inc et al* v. *Peloton Interactive, Inc.,* IPR2019-00295 (PTAB), "Petitioner's Reply to PO Response (Public Redacted)", filed by Flywheel Sports, Inc., filed on Nov. 27, 2019.
*Flywheel Sports, Inc et al* v. *Peloton Interactive, Inc.,* IPR2019-00564 (PTAB), "Petitioner's Reply to PO Response (Public Redacted)", filed by Flywheel Sports, Inc., filed on Nov. 27, 2019.
*Flywheel Sports, Inc et al* v. *Peloton Interactive, Inc.,* IPR2019-00294 (PTAB), "Transcript of Conference Call", filed on Dec. 5, 2019.

(56) References Cited

OTHER PUBLICATIONS

*Peloton Interactive, Inc. v. Echelon Fitness, LLC*, 1-19-cv-01903 (DED), "Motion to Dismiss—filed by Echelon Fitness, LLC",. (Schladweiler, Benjamin), filed on Dec. 6, 2019.
*Peloton Interactive, Inc. v. Echelon Fitness, LLC*, 1-19-cv-01903 (DED), "Opening Brief in Support re 9 MOTION to Dismiss", filed by Echelon Fitness, LLC. (Schladweiler, Benjamin), filed on Dec. 6, 2019.
*Flywheel Sports, Inc et al v. Peloton Interactive, Inc.*, IPR2019-01411 (PTAB), "Response to PO Motion for Permission to Request Correction of Inventorship", filed by Flywheel Sports, Inc., filed on Dec. 6, 2019.
*Flywheel Sports, Inc et al v. Peloton Interactive, Inc.*, IPR2019-00294 (PTAB), "Response to PO Motion for Permission to Request Correction of Inventorship", filed by Flywheel Sports, Inc., filed on Dec. 6, 2019.
*Flywheel Sports, Inc et al v. Peloton Interactive, Inc.*, IPR2019-00295 (PTAB), "Response to PO Motion for Permission to Request Correction of Inventorship", filed by Flywheel Sports, Inc., filed on Dec. 6, 2019.
*Flywheel Sports, Inc et al v. Peloton Interactive, Inc.*, IPR2019-00564 (PTAB), "Response to PO Motion for Permission to Request Correction of Inventorship", filed by Flywheel Sports, Inc., filed on Dec. 6, 2019.
*Peloton Interactive, Inc. v. Flywheel Sports, Inc.*, 2-19-cv-00317 (TXED), "Motion to Dismiss Plaintiff's First Amended Complaint Under Federal Rule of Civil Procedure 12(B)(6) for Improper Claim Splitting", filed by Flywheel Sports, Inc., (Budwin, Joshua), filed on Dec. 10, 2019.
*Peloton Interactive, Inc. v. Flywheel Sports, Inc.*, 2-18-cv-00390 (TXED), "Reply to 133 Claim Construction Brief", filed by Flywheel Sports, Inc., (Budwin, Joshua), filed on Dec. 10, 2019.
*Peloton Interactive, Inc. v. Flywheel Sports, Inc.*, 2-18-cv-00390 (TXED), "Reply to 133 Claim Construction Brief", filed by Peloton Interactive, Inc., (Smith, Melissa), filed on Dec. 17, 2019.
*Peloton Interactive, Inc. v. Flywheel Sports, Inc.*, 2-18-cv-00390 (TXED), "Claim Construction Chart by Peloton Interactive, Inc.", (Smith, Melissa), filed on Dec. 20, 2019.
*Flywheel Sports, Inc et al v. Peloton Interactive, Inc.*, IPR2019-00294 (PTAB), "Patent Owner's Surreply", filed by Peloton Interactive, Inc., filed on Dec. 26, 2019.
*Peloton Interactive, Inc. v. Flywheel Sports, Inc.*, 2-18-cv-00390 (TXED), "Response in Opposition re 89 Motion to Dismiss Plaintiff's Second Amended Complaint for Failure to State a Claim Pursuant to Federal Rule of Civil Procedure 12(b)(6)" filed by Peloton Interactive, Inc., (Smith, Melissa), filed on Aug. 21, 2019.
*Peloton Interactive, Inc. v. Flywheel Sports, Inc.*, 2-18-cv-00390 (TXED), "Reply to Response to Motion re 89 Motion to Dismiss Plaintiff's Second Amended Complaint for Failure to State a Claim Pursuant to Federal Rule of Civil Procedure 12(b)(6)", filed by Flywheel Sports, Inc., (Ginsberg, Jeffrey), filed on Aug. 23, 2019.
*Peloton Interactive, Inc. v. Flywheel Sports, Inc.*, 2-18-cv-00390 (TXED), "Sur-Reply to Reply to Response to Motion re 89 Motion to Dismiss Plaintiff's Second Amended Complaint for Failure to State a Claim Pursuant to Federal Rule of Civil Procedure 12(b)(6)", filed by Peloton Interactive, Inc.,(Smith, Melissa), filed on Aug. 30, 2019.
*Peloton Interactive, Inc. v. Flywheel Sports, Inc.*, 2-18-cv-00390 (TXED), "Report and Recommendations re 89 Motion to Dismiss Plaintiff's Second Amended Complaint for Failure to State a Claim Pursuant to Federal Rule of Civil Procedure 12(b)(6)", filed by Flywheel Sports, Inc., signed by Magistrate Judge Roy S. Payne on Sep. 5, 2019, entered on Sep. 6, 2019.
*Peloton Interactive, Inc. v. Flywheel Sports, Inc.*, 2-18-cv-00390 (TXED), "Objection to 108 Report and Recommendations by Flywheel Sports, Inc.", (Ginsberg, Jeffrey), entered on Sep. 20, 2019.
*Peloton Interactive, Inc. v. Flywheel Sports, Inc.*, 2-18-cv-00390 (TXED), "Response to 112 Objection to Report and Recommendations filed by Peloton Interactive, Inc.", (Smith, Melissa), entered on Oct. 4, 2019.
*Flywheel Sports, Inc et al v. Peloton Interactive, Inc.*, PTAB-IPR-2019-00564, "Patent Owner's Response to Petition for Inter Partes Review [Public Redacted] and Exhibits", Sep. 3, 2019.
*Flywheel Sports, Inc et al v. Peloton Interactive, Inc.*, PTAB-IPR-2019-00295, "Flywheel Infringement Contentions", Sep. 3, 2019.
*Peloton Interactive, Inc. v. Flywheel Sports, Inc.*, 2-19-cv-00317 (TXED), "Complaint against Flywheel Sports, Inc. with attachments", filed by Peloton Interactive, Inc., (Smith, Melissa), entered on Sep. 20, 2019.
*Flywheel Sports, Inc. v. Peloton Interactive, Inc.*, PTAB-IPR-2019-00294, "Peloton's Opposition to Motion to Stay", entered on Oct. 3, 2019.
*Peloton Interactive, Inc. v. Echelon Fitness, LLC.*, 1-19-cv-01903 (DED), "Complaint for Patent Infringement with attachments"—filed with Jury, Magistrate Consent Notice to Plaintiff, entered on Oct. 8, 2019.
*Flywheel Sports, Inc. v. Peloton Interactive, Inc.*, PTAB-IPR-2019-00294, "Peloton Bike Claim Charts", filed Sep. 3, 2019.
*Peloton Interactive, Inc. v. Flywheel Sports, Inc.*, 2-19-cv-00317 (TXED), "Response in Opposition re 25 Motion to Dismiss Plaintiff's Complaint Under Federal Rule of Civil Procedure 12(b)(6) For Improper Claim Splitting.", filed by Peloton Interactive, Inc., filed on Jan. 7, 2020.
*Peloton Interactive, Inc. v. Echelon Fitness, LLC.*, 1-19-cv-01903 (DED), "Amended Complaint for Patent Infringement, Trademark Infringement, Trade Dress Infringement, Trademark and Trade Dress Dilution, Trade Libel, False Advertising, and Unfair Business Practices against Echelon Fitness, LLC", filed by Peloton Interactive, Inc., (Smith, Melissa), filed on Jan. 13, 2020.
*Peloton Interactive, Inc. v. Echelon Fitness, LLC.*, 1-19-cv-01903 (DED), "Motion to Dismiss Patent Infringement Claims", filed by Echelon Fitness, LLC, (Schladweiler, Benjamin), filed on Jan. 17, 2020.
*Peloton Interactive, Inc. v. Echelon Fitness, LLC.*, 1-19-cv-01903 (DED), "Opening Brief in Support re 17 Motion to Dismiss Patent Infringement Claims", filed by Echelon Fitness, LLC, ((Schladweiler, Benjamin), filed on Jan. 17, 2020.
*Peloton Interactive, Inc. v. Flywheel Sports, Inc.*, 2-19-cv-00317 (TXED), "Reply to Response to Motion re 25 Motion to Dismiss Plaintiff's First Amended Complaint Under Federal Rule of Civil Procedure 12(b)(6) For Improper Claim Splitting.", filed by Flywheel Sports, Inc., (Budwin, Joshua), filed on Jan. 22, 2020.
*Peloton Interactive, Inc. v. Echelon Fitness, LLC.*, 1-19-cv-01903 (DED), "Answering Brief in Opposition re 17 Motion to Dismiss Patent Infringement Claims", filed by Peloton Interactive, Inc., (Flynn, Michael), filed on Jan. 27, 2020.
*Flywheel Sports, Inc. et al v. Peloton Interactive, Inc.*, IPR2019-00294 (PTAB), "Joint Motion to Terminate Proceeding", filed on Jan. 30, 2020.
*Flywheel Sports, Inc. et al v. Peloton Interactive, Inc.*, IPR2019-00564 (PTAB), ), "Joint Motion to Terminate Proceeding", filed on Jan. 31, 2020.
*Flywheel Sports, Inc. et al v. Peloton Interactive, Inc.*, IPR2019-01411 (PTAB), Decision Settlement Prior to Institution of Trial 37 C.F.R § 42.74, filed on Feb. 3, 2020.
*Flywheel Sports, Inc. et al v. Peloton Interactive, Inc.*, IPR2019-00294 (PTAB), Termination Due to Settlement After Institution of Trial 35 U.S.C § 317; 37 C.F.R § 42.74, filed on Feb. 3, 2020.
*Peloton Interactive, Inc. v. Flywheel Sports, Inc.*, 2-18-cv-00390 (TXED), "Notice by Peloton Interactive, Inc., Notice of Settlement", (Smith, Melissa), filed Feb. 3, 2020.
*Peloton Interactive, Inc. v. Flywheel Sports, Inc.*, 2-18-cv-00390 (TXED), Joint Motion to Dismiss by Peloton Interactive, Inc. and Proposed Order, (Smith, Melissa), filed on Feb. 3, 2020.
*Peloton Interactive, Inc. v. Echelon Fitness, LLC*, Civil Action No. 1-19-cv-01903 (DDE), "Reply Brief re 17 Motion to Dismiss Patent Infringement Claims", filed by Echelon Fitness, LLC., (Schladweiler, Benjamin), filed on Feb. 6, 2020.

(56) References Cited

OTHER PUBLICATIONS

*Peloton Interactive, Inc.* v. *Echelon Fitness, LLC,* Civil Action No. 1-19-cv-01903 (DDE), Request for Oral Argument by Echolon Fitness, LLC re 17 Motion to Dismiss Patent Infringement Claims, (Schladweiler, Benjamin), filed on Feb. 6, 2020.
*Peloton Interactive, Inc.* v. *Flywheel Sports, Inc.,* Civil Action No. 2-19-cv-00317 (EDTX), "Order granting 42 Motion to Dismiss", Ordered that Plaintiffs claims for relief against Defendant are Dismissed with prejudice, signed by District Judge Rodney Gilstrap, entered: Feb. 6, 2020.
*Peloton Interactive, Inc.* v. *Flywheel Sports, Inc.,* Civil Action No. 2-18-cv-00390 (EDTX), "Order granting 200 Motion to Dismiss", Ordered that Plaintiffs claims against Defendant Flywheel Sports, Inc. are Dismissed With Prejudice, signed by District Judge Robert W. Schroeder, III, entered: Feb. 6, 2020.
*Peloton Interactive, Inc.* v. *Flywheel Sports, Inc.,* Civil Action No. 2-18-cv-00390 (EDTX), "Final Judgment", signed by District Judge Robert W. Schroeder, III on Feb. 6, 2020, entered: Feb. 6, 2020.
*Peloton Interactive, Inc.* v. *ICON Health & Fitness, Inc.,* Civil Action No. 1-20-cv-00662 (DDE), "Complaint for Patent Infringement", filed with Jury Demand against ICON Health & Fitness, Inc.—Magistrate Consent Notice to Plaintiff, filed by Peloton Interactive, Inc., entered: May 18, 2020.
*Echelon Fitness Multimedia, LLC* v. *Peloton Interactive, Inc.,* IPR2020-01187 (PTAB), "Petition for Inter Partes Review of U.S. Pat. No. 10,022,590", filed on Jun. 29, 2020.
*Echelon Fitness Multimedia, LLC* v. *Peloton Interactive, Inc.,* IPR2020-01187 (PTAB), "Petitioner's Power of Attorney", filed on Jun. 29, 2020.
*Echelon Fitness Multimedia, LLC* v. *Peloton Interactive, Inc.,* IPR2020-01187 (PTAB), "Declaration of Kevin Jeffay, Ph.D.", filed on Jun. 29, 2020.
*Echelon Fitness Multimedia, LLC* v. *Peloton Interactive, Inc.,* IPR2020-01187 (PTAB), "Jeff Carlson, the Ipad 2 Pocket Guide", filed on Jun. 29, 2020.
*Echelon Fitness Multimedia, LLC* v. *Peloton Interactive, Inc.,* IPR2020-01187 (PTAB), "Amended Complaint in Peloton Interactive, Inc. v. Echelon Fitness, LLC, Civil Action No. 1:19-cv-01903-RGA, D.E. 16 (D. Del. Jan. 1, 2013)", filed on Jun. 29, 2020.
*Echelon Fitness Multimedia, LLC* v. *Peloton Interactive, Inc.,* IPR2020-01187 (PTAB), "Petition *Flywheel Sports, Inc.* v. *Peloton Interactive, Inc.*", IPR2019-00564, filed Jun. 29, 2020.
*Echelon Fitness Multimedia, LLC* v. *Peloton Interactive, Inc.,* IPR2020-01187 (PTAB), "Preliminary Patent Owner Response in IPR2019-00564", filed Jun. 29, 2020.
*Echelon Fitness Multimedia, LLC* v. *Peloton Interactive, Inc.,* IPR2020-01187 (PTAB), "Institution Decision in IPR2019-00564", filed Jun. 29, 2020.
*Echelon Fitness Multimedia, LLC* v. *Peloton Interactive, Inc.,* IPR2020-01187 (PTAB), "Patent Owner Response in IPR2019-00564", filed Jun. 29, 2020.
*Echelon Fitness Multimedia, LLC* v. *Peloton Interactive, Inc.,* IPR2020-01187 (PTAB), "Petitioners Reply in IPR2019-00564", filed on Jun. 29, 2020.
*Echelon Fitness Multimedia, LLC* v. *Peloton Interactive, Inc.,* IPR2020-01187 (PTAB), "Patent Owner Surreply in IPR2019-00564", filed on Jun. 29, 2020.
*Echelon Fitness Multimedia, LLC* v. *Peloton Interactive, Inc.,* IPR2020-01187 (PTAB), "Joint Claim Construction Chart", *Peloton Interactive, Inc.* v. *Flywheel Sports, Inc.,* Civil Action No. 2:18-cv-00390-RWS-RSP, filed on Jun. 29, 2020.
*Echelon Fitness Multimedia, LLC* v. *Peloton Interactive, Inc.,* IPR2020-01187 (PTAB), "Institution Decision in IPR2019-00294", filed on Jun. 29, 2020.
*Echelon Fitness Multimedia, LLC* v. *Peloton Interactive, Inc.,* IPR2020-01187 (PTAB), "Institution Decision in IPR2019-00295", filed on Jun. 29, 2020.
*Echelon Fitness Multimedia, LLC* v. *Peloton Interactive, Inc.,* IPR2020-01187 (PTAB), "Peloton Interactive, Inc. Brochure", filed on Jun. 29, 2020.
*Echelon Fitness Multimedia, LLC* v. *Peloton Interactive, Inc.,* IPR2020-01187 (PTAB), "Library of Congress Record for Jeff Carlson, the Ipad 2 Pocket Guide", filed on Jun. 29, 2020.
*Echelon Fitness Multimedia, LLC* v. *Peloton Interactive, Inc.,* IPR2020-01186 (PTAB), "Petition for Inter Partes Review of U.S. Pat. No. 10,322,315", filed on Jul. 2, 2020.
*Peloton Interactive, Inc.* v. *Echelon Fitness Multimedia LLC,* Civil Action No. 1-19-cv-01903 (DDE), "Memorandum Opinion", signed by Judge Richard G. Andrews on Jul. 6, 2020, entered on Jul. 6, 2020.
*Peloton Interactive, Inc.* v. *Echelon Fitness Multimedia LLC,* Civil Action No. 1-19-cv-01903 (DDE), "Stipulation of Dismissal of Echelon Fitness, LLC and Substitution of Echelon Fitness Multimedia, LLC by Echelon Fitness, LLC.", (Schladweiler, Benjamin), entered: Jul. 13, 2020.
*Peloton Interactive, Inc.* v. *ICON Health & Fitness, Inc.,* 1-20-cv-00662 (DDE), "Redacted Version of 9 Answer to Complaint, Counterclaim by ICON Health & Fitness, Inc.." (Attachments: # 1 Exhibit A-B) (Haynes, Christine), Docket 12, entered: Jul. 17, 2020.
*Peloton Interactive, Inc.* v. *Echelon Fitness Multimedia LLC,* Civil Action No. 1-19-cv-01903 (DDE), "Answer to 16 Amended Complaint, with Jury Demand and Counterclaims against Peloton Interactive, Inc. by Echelon Fitness Multimedia LLC.", (Schladweiler, Benjamin), modified on Jul. 20, 2020, entered: Jul. 20, 2020.
*Peloton Interactive, Inc.* v. *Echelon Fitness Multimedia LLC,* Civil Action No. 1-19-cv-01903 (DDE), "Answer to 31 Answer to Amended Complaint and Counterclaim and Affirmative Defenses", by Peloton Interactive, Inc., (Moshos, Andrew), modified on Aug. 10, 2020, entered: Aug. 10, 2020.
*Peloton Interactive, Inc.* v. *ICON Health & Fitness, Inc.,* Civil Action No. 1-20-cv-00662 (DDE), "Motion to Partially Dismiss Defendant ICON Health & Fitness, Inc.'s Counterclaims", filed by Peloton Interactive, Inc., (Moshos, Andrew), entered: Aug. 14, 2020.
*Peloton Interactive, Inc.* v. *ICON Health & Fitness, Inc.,* Civil Action No. 1-20-cv-00662 (DDE), "Redacted Version of 18 Declaration, by Peloton Interactive, Inc.", (Attachments: # 1 Exhibit 1, # 2 Exhibit 2, # 3 Exhibit 3) (Moshos, Andrew), entered: Aug. 21, 2020.
*Peloton Interactive, Inc.* v. *ICON Health & Fitness, Inc.,* Civil Action No. 1-20-cv-00662 (DDE), "Redacted Version of 17 Opening Brief in Support", by Peloton Interactive, Inc., (Moshos, Andrew), entered: Aug. 21, 2020.
*Echelon Fitness Multimedia, LLC* v. *Peloton Interactive, Inc.,* IPR2020-01541 (PTAB), "Petition for Inter Partes Review of U.S. Pat. No. 10,486,026", filed on Sep. 1, 2020.
*Peloton Interactive, Inc.* v. *ICON Health & Fitness, Inc.,* Civil Action No. 1-20-cv-00662 (DDE), "Redacted Version of 27 Answer to First Amended Counterclaims", filed by ICON Health & Fitness, Inc., (Haynes, Christine), entered: Sep. 9, 2020.
*Peloton Interactive, Inc.* v. *ICON Health & Fitness, Inc.,* Civil Action No. 1-20-cv-00662 (DDE), "Partial Motion to Dismiss Defendant ICON Health & Fitness, Inc.'s First Amended Counterclaims", filed by Peloton Interactive, Inc., (Moshos, Andrew), entered: Sep. 11, 2020.
*Peloton Interactive, Inc.* v. *ICON Health & Fitness, Inc.,* Civil Action No. 1-20-cv-00662 (DDE), "Redacted Version of 40 Opening Brief in Support", filed by Peloton Interactive, Inc., (Moshos, Andrew), entered: Sep. 18, 2020.
*Peloton Interactive, Inc.* v. *ICON Health & Fitness, Inc.,* Civil Action No. 1-20-cv-00662 (DDE), "Redacted Version of 41 Declaration", filed by Peloton Interactive, Inc., (Moshos, Andrew), entered: Sep. 18, 2020.
*Peloton Interactive, Inc.* v. *ICON Health & Fitness, Inc.,* Civil Action No. 1-20-cv-00662 (DDE), "Redacted Version of 46 Answering Brief in Opposition", filed by ICON Health & Fitness, Inc., (Haynes, Christine), entered: Oct. 6, 2020.
*Peloton Interactive, Inc.* v. *ICON Health & Fitness, Inc.,* Civil Action No. 1-20-cv-00662 (Dde), "Redacted Version of 47 Reply Brief by Peloton Interactive, Inc.", (Moshos, Andrew), entered: Oct. 9, 2020.

(56) References Cited

OTHER PUBLICATIONS

*Echelon Fitness Multimedia, LLC* v. *Peloton Interactive, Inc.,* IPR2020-01186 (PTAB), "Patent Owner's Preliminary Response", filed on Oct. 28, 2020.
*Echelon Fitness Multimedia, LLC* v. *Peloton Interactive, Inc.,* IPR2020-01187 (PTAB), "Patent Owner's Preliminary Response", filed on Oct. 28, 2020.
*Peloton Interactive, Inc.* v. *Echelon Fitness Multimedia LLC, et al.,* Civil Action No. 1-19-cv-01903 (DDE), "Second Amended Complaint for Patent Infringement, Trademark Infringement, Trade Dress Infringement, Trademark and Trade Dress Dilution, Trade Libel, False Advertising, and Unfair Business Practices against Echelon Fitness Multimedia LLC, Echelon Fitness, LLC, Echelon Studio, LLC, and Viatek Consumer Products Group, Inc.", filed by Peloton Interactive, Inc., entered: Dec. 1, 2020.
*Echelon Fitness Multimedia, LLC* v. *Peloton Interactive, Inc.,* IPR2020-01541 (PTAB), "Patent Owner's Preliminary Response", filed on Dec. 7, 2020.
*Peloton Interactive, Inc.* v. *Echelon Fitness Multimedia LLC, et al.,* Civil Action No. 1-19-cv-01903 (DDE), Answer to 77 Amended Complaint with Jury Demand, and Counterclaims against Peloton Interactive, Inc., by Echelon Studio, LLC, Echelon Fitness Multimedia LLC, Echelon Fitness, LLC, Viatek Consumer Products Group, Inc., (Schladweiler, Benjamin), entered: Dec. 14, 2020.
*Peloton Interactive, Inc.* v. *Echelon Fitness Multimedia LLC, et al.,* Civil Action No. 1-19-cv-01903 (DDE), "Answer to 16 Amended Complaint, with Jury Demand and Counterclaims against Peloton Interactive, Inc., by Echelon Fitness Multimedia LLC, Echelon Fitness, LLC, Echelon Studio, LLC, Viatek Consumer Products Group, Inc.", (Schladweiler, Benjamin), entered Dec. 17, 2020.
*Peloton Interactive, Inc.* v. *Echelon Fitness Multimedia LLC, et al.,* Civil Action No. 1-19-cv-01903 (DDE), "Answer to 86 Answer to Amended Complaint and Counterclaim, by Peloton Interactive, Inc.", (Flynn, Michael), entered: Dec. 28, 2020.
*Echelon Fitness Multimedia, LLC* v. *Peloton Interactive, Inc.,* IPR2020-01187 (PTAB), " Granting Institution of Inter Partes Review 35 U.S.C. sec 314, 37 C.F.R. sec 42.4", filed on Jan. 26, 2001.
*Echelon Fitness Multimedia, LLC* v. *Peloton Interactive, Inc.,* IPR2020-01186 (PTAB), " Granting Institution of Inter Partes Review 35 U.S.C. sec 314, 37 C.F.R. sec 42.4", filed on Jan. 26, 2001.
*Peloton Interactive, Inc.* v. *Echelon Fitness Multimedia LLC, et al.,* Civil Action No. 1-19-cv-01903 (DDE), "Stipulation of Dismissal of Certain Claims and Counterclaims", filed by Peloton Interactive, Inc., (Flynn, Michael), entered: Feb. 5, 2021.
*Peloton Interactive, Inc.* v. *Echelon Fitness Multimedia LLC, et al.,* Civil Action No. 1-19-cv-01903 (DDE), "So Ordered Granting 105 Joint Stipulation of Dismissal of Certain Claims and Counterclaims", signed by Judge Richard G. Andrews on Feb. 8, 2021. (nms).
*Peloton Interactive, Inc.* v. *ICON Health & Fitness, Inc.,* Civil Action No. 1-20-cv-00662 (DDE), "Joint Claim Construction Chart", by Peloton Interactive, Inc., (Flynn, Michael), modified on Feb. 11, 2021, entered: Feb. 11, 2021.
*Peloton Interactive, Inc.* v. *Echelon Fitness Multimedia LLC, et al.,* Civil Action No. 1-19-cv-01903 (DDE), "Joint Claim Construction Chart", by Peloton Interactive, Inc., (Flynn, Michael), modified on Feb. 11, 2021, entered: Feb. 11, 2021.
*Peloton Interactive, Inc.* v. *ICON Health & Fitness, Inc.,* Civil Action No. 1-20-cv-00662 (DDE), "Claim Construction Chart" by ICON Health & Fitness, Inc., (Haynes, Christine), entered: Feb. 18, 2021.
*Echelon Fitness Multimedia, LLC* v. *Peloton Interactive, Inc.,* IPR2020-01541 (PTAB), "Trial Instituted Document", filed Mar. 3, 2021.
"CompuTrainer", Racermate, 2017, retrieved Nov. 30, 2018 from http://www.racermateinc.com/computrainer/, 1 page.

*Echelon Fitness Multimedia, LLC* v. *Peloton Interactive, Inc.,* IPR2021-00848 (PTAB), U.S. Pat. No. 10,639,521, "Petition for Inter Partes Review", entered on May 3, 2021.
*Echelon Fitness Multimedia, LLC* v. *Peloton Interactive, Inc.,* IPR2021-00848 (PTAB) and IPR2019-00564, U.S. Pat. No. 9,861,855, "Patent Owner's Preliminary Response To Petition for Inter Partes Review", entered on May 3, 2021.
*Echelon Fitness Multimedia, LLC* v. *Peloton Interactive, Inc.,* IPR2021-00848 (PTAB) and IPR2019-00564, U.S. Pat. No. 9,861,855, "Patent Owner's Response To Petition for Inter Partes Review", entered on May 3, 2021.
*Echelon Fitness Multimedia, LLC* v. *Peloton Interactive, Inc.,* IPR2021-00848 (PTAB) and IPR2020-01541, U.S. Pat. No. 10,486,026, "Patent Owner's Preliminary Response", entered on May 3, 2021.
*Echelon Fitness Multimedia, LLC* v. *Peloton Interactive, Inc.,* IPR2021-00848 (PTAB) and IPR2020-01541, U.S. Pat. No. 10,486,026, "Decision Granting Institution of Inter Partes Review 35 U.S.C. § 314, 37 C.F.R. § 42.4", Paper 16, entered on May 3, 2021.
*Echelon Fitness Multimedia, LLC* v. *Peloton Interactive, Inc.,* IPR2021-00848 (PTAB), Civil Case Action No. 21-160 (RGA), "Peloton Interactive, Inc.'S Opposition To Echelon's Motion To Dismiss", entered on May 3, 2021.
*Echelon Fitness Multimedia, LLC* v. *Peloton Interactive, Inc.,* IPR2020-01186 (PTAB), Patent No. 10,322,315, "Patent Owner's Response", entered on May 5, 2021.
*Echelon Fitness Multimedia, LLC* v. *Peloton Interactive, Inc.,* IPR2020-01187 (PTAB), Patent No. 10,022,590, "Patent Owner's Response", entered on May 5, 2021.
*Echelon Fitness Multimedia, LLC* v. *Peloton Interactive, Inc.,* IPR2020-01186 (PTAB) and IPR2020-01187 (PTAB), U.S. Pat. No. 10,322,315 and U.S. Pat. No. 10,022,590, Exhibit 2002, "Declaration of Henry H. Houh in Support of Patent Owner's Response", entered on May 5, 2021.
*Echelon Fitness Multimedia, LLC* v. *Peloton Interactive, Inc.,* IPR2020-01186 (PTAB) and IPR2020-01187 (PTAB), U.S. Pat. No. 10,322,315 and U.S. Pat. No. 10,022,590, Exhibit 2003, "Henry H. Houh's Curriculum Vitae", entered on May 5, 2021.
*Echelon Fitness Multimedia, LLC* v. *Peloton Interactive, Inc.,* IPR2020-01186 (PTAB) and IPR2020-01187 (PTAB), U.S. Pat. No. 10,322,315 and U.S. Pat. No. 10,022,590, Exhibit 2004, "Declaration of Jim Rutberg in Support of Patent Owner's Response", entered on May 5, 2021.
*Echelon Fitness Multimedia, LLC* v. *Peloton Interactive, Inc.,* IPR2020-01186 (PTAB) and IPR2020-01187 (PTAB), U.S. Pat. No. 10,322,315 and U.S. Pat. No. 10,022,590, Exhibit 2005, "Jim Rutberg's Curriculum Vitae", entered on May 5, 2021.
*Echelon Fitness Multimedia, LLC* v. *Peloton Interactive, Inc.,* IPR2020-01186 (PTAB), U.S. Pat. No. 10,322,315, Exhibit 2006, "Deposition of Kevin Jeffray, Ph.D.", conducted virtually on Mar. 29, 2021, entered on May 5, 2021.
*Echelon Fitness Multimedia, LLC* v. *Peloton Interactive, Inc.,* IPR2020-01186 (PTAB), Exhibit 2007, entered on May 5, 2021.
*Echelon Fitness Multimedia, LLC* v. *Peloton Interactive, Inc.,* IPR2020-01186 (PTAB), Exhibit 2008, "JJ's Last Ride and the Power of Peloton", entered on May 5, 2021.
*Echelon Fitness Multimedia, LLC* v. *Peloton Interactive, Inc.,* IPR2020-01186 (PTAB), Exhibit 2009, entered on May 5, 2021.
*Echelon Fitness Multimedia, LLC* v. *Peloton Interactive, Inc.,* IPR2020-01186 (PTAB), Exhibit 2010, entered on May 5, 2021.
*Echelon Fitness Multimedia, LLC* v. *Peloton Interactive, Inc.,* IPR2020-01186 (PTAB), Exhibit 2011, entered on May 5, 2021.
*Echelon Fitness Multimedia, LLC* v. *Peloton Interactive, Inc.,* IPR2020-01186 (PTAB) and IPR2020-01187 (PTAB), Exhibit 2012, "Spinning Trademarked; Gyms being threatened for holding Spinning Classes Sans License", (Mike Masnick), entered on May 5, 2021.
*Echelon Fitness Multimedia, LLC* v. *Peloton Interactive, Inc.,* IPR2020-01186 (PTAB), Exhibit 2013, entered on May 5, 2021.
*Echelon Fitness Multimedia, LLC* v. *Peloton Interactive, Inc.,* IPR2020-01186 (PTAB), Exhibit 2014, entered on May 5, 2021.
*Echelon Fitness Multimedia, LLC* v. *Peloton Interactive, Inc.,* IPR2020-01186 (PTAB), Exhibit 2015, entered on May 5, 2021.

(56) References Cited

OTHER PUBLICATIONS

*Echelon Fitness Multimedia, LLC v. Peloton Interactive, Inc.*, IPR2020-01186 (PTAB), Exhibit 2016, entered on May 5, 2021.
*Echelon Fitness Multimedia, LLC v. Peloton Interactive, Inc.*, IPR2020-01186 (PTAB), Exhibit 2017, entered on May 5, 2021.
*Echelon Fitness Multimedia, LLC v. Peloton Interactive, Inc.*, IPR2020-01186 (PTAB), Exhibit 2018, entered on May 5, 2021.
*Echelon Fitness Multimedia, LLC v. Peloton Interactive, Inc.*, IPR2020-01186 (PTAB), Exhibit 2019, entered on May 5, 2021.
*Echelon Fitness Multimedia, LLC v. Peloton Interactive, Inc.*, IPR2020-01186 (PTAB), Exhibit 2020, entered on May 5, 2021.
*Echelon Fitness Multimedia, LLC v. Peloton Interactive, Inc.*, IPR2020-01186 (PTAB), Exhibit 2021, entered on May 5, 2021.
*Peloton Interactive, Inc. v. ICON Health & Fitness, Inc.*, Docket, Civil Action No. 1-20-cv-00662 (D.D.E), "Joint Claim Construction Brief", by Peloton Interactive, Inc., Document 106, entered on Jun. 2, 2021 (Moshos, Andrew).
*Peloton Interactive, Inc. v. ICON Health & Fitness, Inc.*, Docket, Civil Action No. 1-20-cv-00662 (D.D.E), "Appendix of Exhibits in Support of Joint Claim Construction Brief", by Peloton Interactive, Inc., (Attachments: # 1 Exhibits P1-P15, D1-D12), Document 107, entered on Jun. 2, 2021 (Moshos, Andrew).
*Echelon Fitness Multimedia, LLC v. Peloton Interactive, Inc.*, PTAB-IPR-2020-01541, U.S. Pat. No. 10,486,026, "Patent Owner's Response (Redacted)", by Peloton Interactive, Inc., entered on Jun. 11, 2021.
*Peloton Interactive, Inc. v. ICON Health & Fitness, Inc.*, Docket, Civil Action No. 1-20-cv-00662 (D.D.E), "Markman Order", Signed by Judge Richard G. Andrews, entered on Jun. 23, 2021.
*Peloton Interactive, Inc. v. Echelon Fitness, LLC*, Civil Action No. 1:19-cv-01903 (D.D.E), "Markman Order", Signed by Judge Richard G. Andrews, entered on Jun. 23, 2021.
*Echelon Fitness Multimedia, LLC v. Peloton Interactive, Inc.*, IPR2020-01186 (PTAB), U.S. Pat. No. 10,322,315, "Petitioner's Reply" with Exhibits, document 35, Aug. 3, 2021.
*Echelon Fitness Multimedia, LLC v. Peloton Interactive, Inc.*, IPR2020-01187 (PTAB), U.S. Pat. No. 10,022,590, "Petitioner's Reply", document 35, Aug. 3, 2021.
*Peloton Interactive, Inc. v. ICON Health & Fitness, Inc.*, Civil Action No. 1-20-cv-00662 (DDE), Document 132, Memorandum Opinion: Within five days the parties shall submit a proposed order consistent with this Memorandum Opinion suitable for submission to the jury. Signed by Judge Richard G. Andrews on Aug. 3, 2021. Associated Cases: 1:20-cv-00662-RGA, 1:19-cv-01903-RGA (Entered: Aug. 3, 2021).
*Peloton Interactive, Inc. v. ICON Health & Fitness, Inc.*, Civil Action No. 1-20-cv-00662 (DDE), "Letter To the Honorable Richard G. Andrews", from Michael Flynn, regarding pro-proposed claim construction order Memorandum Opinion. (Attachments: # 1 Exhibit 1, # 2 Exhibit 2) (Flynn, Michael) Modified on Aug. 10, 2021 (Entered: Aug. 9, 2021).
*Echelon Fitness Multimedia, LLC v. Peloton Interactive, Inc.*, IPR2021-00848 (PTAB), U.S. Pat. No. 10,639,521, Document 6, "Patent Owner's Preliminary Response" with Exhibits, Aug. 20, 2021.
*Echelon Fitness Multimedia, LLC v. Peloton Interactive, Inc.*, IPR2020-01541 (PTAB), U.S. Pat. No. 10,486,026, "Petitioner's Reply" [Redacted] with Exhibits, Document 38, Sep. 13, 2021.
*Echelon Fitness Multimedia, LLC v. Peloton Interactive, Inc.*, IPR2020-01187 (PTAB), U.S. Pat. No. 10,022,590, "Patent Owner's Surreply" with Exhibits, Document 43, Sep. 14, 2021.
*Echelon Fitness Multimedia, LLC v. Peloton Interactive, Inc.*, IPR2020-01186 (PTAB), U.S. Pat. No. 10,322,315, "Corrected Patent Owner's Surreply", Document 44, Sep. 21, 2021.
*Echelon Fitness Multimedia, LLC v. Peloton Interactive, Inc.*, IPR2020-01541 (PTAB), U.S. Pat. No. 10,486,026, "Patent Owner's Surreply" with Exhibits, document 2108, Oct. 22, 2021.
*Peloton Interactive, Inc. v. iFIT, Inc., f/k/a ICON Health & Fitness*, Civil Action No. 1-21-cv-01605 (DDE), Document 1, Complaint for Patent Infringement: filed with Jury Demand against iFIT, Inc.— Magistrate Consent Notice to Pltf—filed by Peloton Interactive, Inc., (Entered: Nov. 15, 2021).
*Peloton Interactive, Inc. v. Echelon Fitness Multimedia LLC*, Civil Action No. 1-21-cv-01607 (DDE), Document 1, Complaint for Patent Infringement: filed with Jury Demand against Echelon Fitness Multimedia, LLC—Magistrate Consent Notice to Pltf—filed by Peloton Interactive, Inc., (Entered: Nov. 15, 2021).
*Peloton Interactive, Inc. v. Echelon Fitness Multimedia LLC*, Civil Action No. 1-19-cv-01903 (DDE), Answer to 1 Complaint, with Jury Demand Coutnerclaim against Peloton Interactive, Inc. by Echelon Fitness Multimedia, LLC, (Entered: Nov. 15, 2021).
*Peloton Interactive, Inc. v. Echelon Fitness Multimedia LLC*, Civil Action No. 1-21-cv-00160 (DDE), Answer to Amended Complaint, with Jury Demand and Coutnerclaim against Peloton Interactive, Inc. by Echelon Fitness Multimedia, LLC, (Entered: Nov. 17, 2021).
*Peloton Interactive, Inc. v. Echelon Fitness Multimedia LLC*, Civil Action No. 1-19-cv-01903 (DDE), Answer to 209 Answer to Amended Complaint and Coutnerclaims, by Peloton Interactive, Inc., (Entered: Dec. 6, 2021).
*IFIT, Inc., f/k/a ICON Health & Fitness, Inc. v. Peloton Interactive, Inc. v.*, IPR2022-00323 (PTAB), U.S. Pat. No. 10,639,521, Petition For Inter Partes Review of Claims 1-20 of U.S. Pat. No. 10,639,421, Dec. 17, 2021.
*Peloton Interactive, Inc. v. Echelon Fitness Multimedia LLC*, 1-19-cv-01903-247 (DDE), "Defendant's Amended Counterclaims for Antitrust, Tortious Interference, Unfair Competition, False Advertising, and Declaratory Judgement of Patent Invalidity and Non-Infringement Against Peloton Interactive, Inc." [Redacted Version], filed on: Jan. 12, 2022.
*Echelon Fitness Multimedia, LLC v. Peloton Interactive, Inc.*, IPR2020-01186 (PTAB), U.S. Pat. No. 10,322,315, "Final Written Decision", Document 52, Jan. 25, 2022.
*Echelon Fitness Multimedia, LLC v. Peloton Interactive, Inc.*, IPR2020-01187 (PTAB), U.S. Pat. No. 10,022,590, "Final Written Decision", Document 51, Jan. 25, 2022.
*Peloton Interactive, Inc. v. ICON Health & Fitness, Inc.*, 1-20-cv-00662 (DDE), Stipulation of Dismissal by Peloton Interactive, Inc., (Flynn, Michael) (Entered: May 16, 2022).
*Peloton Interactive, Inc. v. IFIT, Inc. f/k/a ICON Health & Fitness, Inc.*, 1-21-cv-01605 (DDE), so Ordered Granting 25 Stipulation and Proposed Order of Dismissal, (***Civil Case Terminated). Signed by Judge Richard G. Andrews on May 17, 2022. (nms) (Entered: May 17, 2022).
*Peloton Interactive, Inc. v. ICON Health & Fitness, Inc.*, 1-20-cv-00662 (DDE), so Ordered Granting 25 Stipulation and Proposed Order of Dismissal, (***Civil Case Terminated). Signed by Judge Richard G. Andrews on May 17, 2022. (nms) (Entered: May 17, 2022).
Certain Interactive Fitness Products Including Stationary Exercise Bikes, Treadmills, Elliptical Machines, and Rowing Machines and Components Thereof; Inc. No. 337-TA-1310 (Violation) 337-TA-1310 (ITC), Joint Motion to Terminate the Investigation, May 19, 2022.
*IFIT, Inc., f/k/a ICON Health & Fitness, Inc. v. Peloton Interactive, Inc. v.*, IPR2022-00323 (PTAB), Joint Motion to Terminate Proceeding, May 20, 2022.
*IFIT, Inc., f/k/a ICON Health & Fitness, Inc. v. Peloton Interactive, Inc. v.*, IPR2022-00323 (PTAB), Termination Decision: Pre-DI Settlement, Jun. 2, 2022.
*Echelon Fitness Multimedia, LLC v. Peloton Interactive, Inc.*, IPR2021-00848 (PTAB), [Public] Petitioner's Reply, Jun. 6, 2022.
*Echelon Fitness Multimedia, LLC v. Peloton Interactive, Inc.*, IPR2021-00848 (PTAB), Transcript of Deposition of Jim Rutberg, taken Jun. 25, 2021, Jun. 6, 2022.
*Echelon Fitness Multimedia, LLC v. Peloton Interactive, Inc.*, IPR2021-00848 (PTAB), Declaration of Dr. Houh, filed by Petitioner as Exhibit 1003 in *Peloton Interactive, Inc. v. ICON Health & Fitness, Inc.*, IPR2021-00342 (Houh-062-IPR-Declaration), Jun. 6, 2022.
*Echelon Fitness Multimedia, LLC v. Peloton Interactive, Inc.*, IPR2021-00848 (PTAB), Jan. 11, 2012 Internet Archive capture of

(56) References Cited

OTHER PUBLICATIONS www.thefreedictionary.com/leaderboard showing the American Heritage 2009 definition of leaderboard (American Heritage Definition (1999)), Jun. 6, 2022.
*Echelon Fitness Multimedia, LLC v. Peloton Interactive, Inc.,* IPR2021-00848 (PTAB), Declaration of Dr. Kevin C. Almeroth, Document 62, *Peloton Interactive, Inc. v. Echelon Fitness, LLC,* 1:19-cv-01903-RGA, (D. Del.) (Redacted Filing Date December 7. 2020) (Almeroth Declaration), Jun. 6, 2022.
*Echelon Fitness Multimedia LLC v. Peloton Interactive, Inc.,* IPR2021-00848 (PTAB), Petition, *Peloton Interactive, Inc. v. ICON Health & Fitness, Inc.* IPR2021-00342, Paper 2 (Dec. 18, 2020) (062-IPR-Petition), Jun. 6, 2022.
*Echelon Fitness Multimedia LLC v. Peloton Interactive, Inc.,* IPR2021-00848 (PTAB), Transcript of deposition of Dr. Henry Houh, taken Jul. 8, 2021 (Houh Transcript), Jun. 6, 2022.
*Echelon Fitness Multimedia LLC v. Peloton Interactive, Inc.,* IPR2021-00848 (PTAB), Reply Declaration of Dr. Kevin Jeffay, previously submitted as Ex-1056 in IPR2020-01186 and IPR2020-01187 (Jeffay Reply Declaration 315-590), Jun. 6, 2022.
*Echelon Fitness Multimedia LLC v. Peloton Interactive, Inc.,* IPR2021-00848 (PTAB), Notice of Settlement, *Peloton Interactive, Inc. v. Flywheel Sports, Inc.,* Civil Action No. 2:18-CV-00390-RWS-RSP (E.D. Tex. Feb. 3, 2020) (Notice of Settlement), Jun. 6, 2022.
*Echelon Fitness Multimedia LLC v. Peloton Interactive, Inc.,* IPR2021-00848 (PTAB), Defendant Answer and Counterclaims, *Peloton Interactive, Inc. v. ICON Health & Fitness, Inc.,* Civil Action No. 20-662-RGA (Jul. 13, 2020 (ICON Answer and Counterclaims), Jun. 6, 2022.
*Echelon Fitness Multimedia LLC v. Peloton Interactive, Inc.,* IPR2021-00848 (PTAB), Final Written Decision in IPR2020-01541, Paper 56 (Mar. 2, 2022) (026-FWD), Jun. 6, 2022.
*Echelon Fitness Multimedia LLC v. Peloton Interactive, Inc.,* IPR2021-00848 (PTAB), Final Written Decision in IPR2020-01187, Paper 51 (Jan. 25, 2022) (590-FWD), Jun. 6, 2022.
*Echelon Fitness Multimedia LLC v. Peloton Interactive, Inc.,* IPR2021-00848 (PTAB), Declaration of Dr. Mark Ehsani, filed by Patent Owner as Exhibit 2012 in IPRs 2019-00294, 2019-00295 and 2019-00564 (Ehsani Declaration), Jun. 6, 2022.
*Echelon Fitness Multimedia LLC v. Peloton Interactive, Inc.,* IPR2021-00848 (PTAB), 2012 Flywheel publication, available at http://web.archive.org/web/20120128121139/http://new-york.flywheelsports.com:80/performance-metrics, Jun. 6, 2022.
*Echelon Fitness Multimedia LLC v. Peloton Interactive, Inc.,* IPR2021-00848 (PTAB), [Public] Reply Declaration of Kevin Jeffay, Ph.D. (Jeffay Reply), Jun. 6, 2022.
*Echelon Fitness Multimedia LLC v. Peloton Interactive, Inc.,* IPR2021-00848 (PTAB), Soul Cycle vs. Flywheel: A comparison shop and spin, WellandGoodNYC.com (Feb. 22, 2010) available at https://web.archive.org/web/20161115223126/http://www.wellandgoodsweat/soul-cycle-vs-flywheel-a-comparison-shop-and-spin/, Jun. 6, 2022.
*Echelon Fitness Multimedia LLC v. Peloton Interactive, Inc.,* IPR2021-00848 (PTAB), ICI/PRO Indoor Cycling 2.0 (Nov. 9, 2011), Adding some friendly competition to your class, Jun. 6, 2022.
Certain Interactive Fitness Products Including Stationary Exercise Bikes, Treadmills, Elliptical Machines, and Rowing Machines and Components Thereof; Inc. No. 337-TA-1310 (Violation) 337-TA-1310 (ITC), Supplement to Joint Motion to Terminate the Investigation, Jun. 13, 2022.
Certain Interactive Fitness Products Including Stationary Exercise Bikes, Treadmills, Elliptical Machines, and Rowing Machines and Components Thereof; Inc. No. 337-TA-1310 (Violation) 337-TA-1310 (ITC), Initial Determination Terminating the Investigation Based on a Settlement Agreement, Jun. 23, 2022.
*Peloton Interactive, Inc. Echelon Fitness Multimedia LLC* 1-21-cv-01607 (DDE), Second Amended Complaint against Echelon Fitness Multimedia, LLC—filed by Peloton Interactive, Inc. (Attachments: #1 Exhibit 1) (Flynn, Michael) Modified on Jun. 30, 2022 (nms). (Entered: Jun. 30, 2022), Jun. 30, 2022.
*Peloton Interactive, Inc. Echelon Fitness Multimedia LLC* 1-21-cv-01607 (DDE), Answer to 30 Amended Complaint with Jury Demand, by Echolon Fitness Multimedia, LLC. (Schladweiler, Benjamin) Modified on Jul. 14, 2022 (nms). (Entered: Jul. 14, 2022), Jul. 14, 2022.
Patent Owner's Unopposed Motion to File Documents Under Seal *Echelon Fitness Multimedia LLC v. Peloton Interactive, Inc.,* IPR2021-00848 (PTAB), Jul. 18, 2022.
*Echelon Fitness Multimedia LLC v. Peloton Interactive, Inc.,* IPR2021-00848 (PTAB), Patent Owner's Surreply—Redacted, Jul. 18, 2022.
Certain Interactive Fitness Products Including Stationary Exercise Bikes, Treadmills, Elliptical Machines, and Rowing Machines and Components Thereof; Inc. No. 337-TA-1310 (Violation) 337-TA-1310 (ITC), Commission Determination Not to Review an Initial Determination Terminating the Investigation Based on Settlement; Termination of the Investigation, Jul. 25, 2022.
*Echelon Fitness Multimedia LLC v. Peloton Interactive, Inc.,* IPR2021-00848 (PTAB), Order Setting Oral Argument, Aug. 3, 2022.

\* cited by examiner

EXERCISE SYSTEM AND METHOD

CROSS-REFERENCE TO RELATED APPLICATIONS

This application is a continuation of and claims priority to U.S. patent application Ser. No. 18/186,846, filed Mar. 20, 2023, which is a continuation of U.S. patent application Ser. No. 17/709,169, filed Mar. 30, 2022, and issued as U.S. Pat. No. 11,610,664 on Mar. 21, 2023, which is a continuation of and claims priority to U.S. patent application Ser. No. 17/492,522, filed Oct. 1, 2021, and issued as U.S. Pat. No. 11,295,849 on Apr. 5, 2022, which is a continuation of and claims priority to U.S. patent application Ser. No. 17/220,876, filed Apr. 1, 2021, and issued as U.S. Pat. No. 11,139,061 on Oct. 5, 2021, which is continuation of and claims priority to U.S. patent application Ser. No. 16/902,195, filed Jun. 15, 2020, and issued as U.S. Pat. No. 11,081,224 on Aug. 3, 2021, which is a continuation of and claims priority to U.S. patent application Ser. No. 16/866,499, filed May 4, 2020, and issued as U.S. Pat. No. 11,183,288 on Nov. 23, 2021, which is a continuation of and claims priority to U.S. patent application Ser. No. 16/666,332, filed Oct. 28, 2019, and issued as U.S. Pat. No. 10,639,521 on May 5, 2020, which is a continuation of and claims priority to U.S. patent application Ser. No. 16/412,327, filed May 14, 2019, and issued as U.S. Pat. No. 10,486,026 on Nov. 26, 2019, which is a continuation of and claims priority to U.S. patent Ser. No. 16/036,894, filed Jul. 16, 2018, and issued as U.S. Pat. No. 10,322,315 on Jun. 18, 2019, which is a continuation of and claims priority to U.S. patent application Ser. No. 15/865,206 filed Jan. 8, 2018, and issued as U.S. Pat. No. 10,022,590 on Jul. 17, 2018, which is a continuation of and claims priority to U.S. patent application Ser. No. 14/992,032 filed Jan. 11, 2016, and issued as U.S. Pat. No. 9,861,855 on Jan. 9, 2018, which is a continuation of and claims priority to U.S. patent application Ser. No. 14/930,398 filed on Nov. 2, 2015, and issued as U.S. Pat. No. 9,233,276 on Jan. 12, 2016, which is a continuation of and claims priority to U.S. patent application Ser. No. 13/956,087 filed on Jul. 31, 2013, and issued as U.S. Pat. No. 9,174,085 on Nov. 3, 2015, which claims the benefit of U.S. Provisional Patent Application No. 61/677,985 filed on Jul. 31, 2012, and U.S. Provisional Patent Application No. 61/798,342 filed on Mar. 15, 2013, all of which are hereby incorporated by reference in their entirety as if set forth herein.

This application is a continuation of and claims priority to U.S. patent application Ser. No. 18/186,846, filed Mar. 20, 2023, which is a continuation of U.S. patent application Ser. No. 17/709,169, filed Mar. 30, 2022, and issued as U.S. Pat. No. 11,610,664 on Mar. 21, 2023, which is a continuation-in-part of and claims priority to U.S. application Ser. No. 17/120,928, filed Dec. 14, 2020, and issued as U.S. Pat. No. 11,400,344 on Aug. 2, 2022, which is a continuation of and claims priority to U.S. application Ser. No. 15/686,875, filed Aug. 25, 2017, and issued as U.S. Pat. No. 10,864,406 on Dec. 15, 2020, which is a nonprovisional of and claims the benefit of U.S. Provisional Application No. 62/380,412, filed Aug. 27, 2016, all of which are hereby incorporated by reference in their entirety as if set forth herein.

BACKGROUND OF THE INVENTION

Field of the Invention

The invention relates generally to the field of exercise equipment and methods. In particular, the invention relates to a system and method for providing streaming and on-demand exercise classes.

Description of Related Art

Humans are competitive by nature, striving to improve their performance both as compared to their own prior efforts and as compared to others. Humans are also drawn to games and other diversions, such that even tasks that a person may find difficult or annoying can become appealing if different gaming elements are introduced. Existing home and gym-based exercise systems and methods frequently lack key features that allow participants to compete with each other and that gamify exercise activities.

While some existing exercise equipment incorporates diversions such as video display screens that present content or performance data to the user while they exercise, these systems lack the ability to truly engage the user in a competitive or gaming scenario that improves both the user's experience and performance.

To improve the experience and provide a more engaging environment, gyms offer classes such as cycling classes where the instructor and participants exercise on stationary bikes accompanied by music. The instructor and music combine to motivate participants to work harder and maintain better pedal cadence or tempo. More recently, boutique cycling studios have taken the cycling class concept to dedicated spaces to create even more powerful class experiences.

All of these class-based experiences, however, are accessible only at specific times and locations. As a result, they are unavailable to many potential users, generally are very expensive, and often sell-out so that even users in a location convenient to the cycling studio cannot reserve a class. The present invention addresses these problems, providing a stationary bike that incorporates multimedia inputs and outputs for live streaming or archived instructional content, socially networked audio and video chat, networked performance metrics and competition capabilities, along with a range of gamification features.

SUMMARY OF THE INVENTION

A method for displaying live and archived cycling classes, in various embodiments comprising displaying information about available live and archived cycling classes that can be accessed by a first user using a first stationary bike via a digital communication network on a display screen at a first location, whereby the first user can select either a live cycling class or select among a plurality of archived cycling classes. Receiving from the first user a selection of one of the available live or archived cycling classes, outputting digital video and audio content comprising the selected cycling class at the first location to the first user, detecting a plurality of performance parameters from the first stationary bike at the first location at a particular point in the selected cycling class, displaying at least one of the plurality of performance parameters detected from the first stationary bike at the first location on the display screen, and displaying at least one of a plurality of performance parameters from a second stationary bike at a second location on the display screen at the first location such that at least one of the performance parameters from the first stationary bike at the particular point in the selected cycling class and at least one of the performance parameters from the second stationary bike at the same point in the selected cycling class are presented for comparison on the display screen at the first location.

In various exemplary embodiments, the digital video and audio content are output in substantially in real-time. In various exemplary embodiments, the digital video and audio content are archived content provided from a database. In various exemplary embodiments, further comprising presenting the performance parameters in a secondary window. In various exemplary embodiments, the performance parameters include pedal cadence, power output, or heartrate. In various exemplary embodiments, further comprising receiving video chat data from a server for display to the user on the display screen at the first location.

A method for displaying live and archived cycling classes comprising displaying information about available live and archived cycling classes that can be accessed by a first user using a first stationary bike via a digital communication network on a display screen at a first location, whereby the first user can select either a live cycling class or select among a plurality of archived cycling classes, receiving from the first user a selection of one of the available live or archived cycling classes, outputting digital video and audio content comprising the selected cycling class at the first location to the first user, detecting a plurality of performance parameters from the first stationary bike at the first location at a particular point in the selected cycling class, displaying at least one of the plurality of performance parameters detected from the first stationary bike at the first location on the display screen, and displaying at least one of a plurality of performance parameters from each of a plurality of other stationary bikes at a plurality of other locations on the display screen at the first location such that at least one of the performance parameters from the first stationary bike at the particular point in the selected cycling class and at least one of the performance parameters from the plurality of other stationary bikes at the same point in the selected cycling class are presented for comparison on the display screen at the first location.

In various exemplary embodiments, the digital video and audio content are output in substantially in real-time. In various exemplary embodiments, the digital video and audio content are archived content provided from a database. In various exemplary embodiments, further comprising presenting the performance parameters in a secondary window. In various exemplary embodiments, the performance parameters include pedal cadence, power output, or heartrate. In various exemplary embodiments, further comprising receiving video chat data from a server for display to the user on the display screen at the first location.

BRIEF DESCRIPTION OF THE DRAWINGS

FIG. 6 is an illustration of an exemplary embodiment of a user interface screen providing a cycling class schedule as disclosed herein.

FIG. 7 is an illustration of an exemplary embodiment of a user interface screen displaying cycling classes available on-demand as disclosed herein.

FIG. 13 is an illustration of an exemplary embodiment of a web page displaying user information as disclosed herein.

FIG. 14 is an illustration of an exemplary embodiment of a web page displaying user information as disclosed herein.

DETAILED DESCRIPTION

Figure 1:
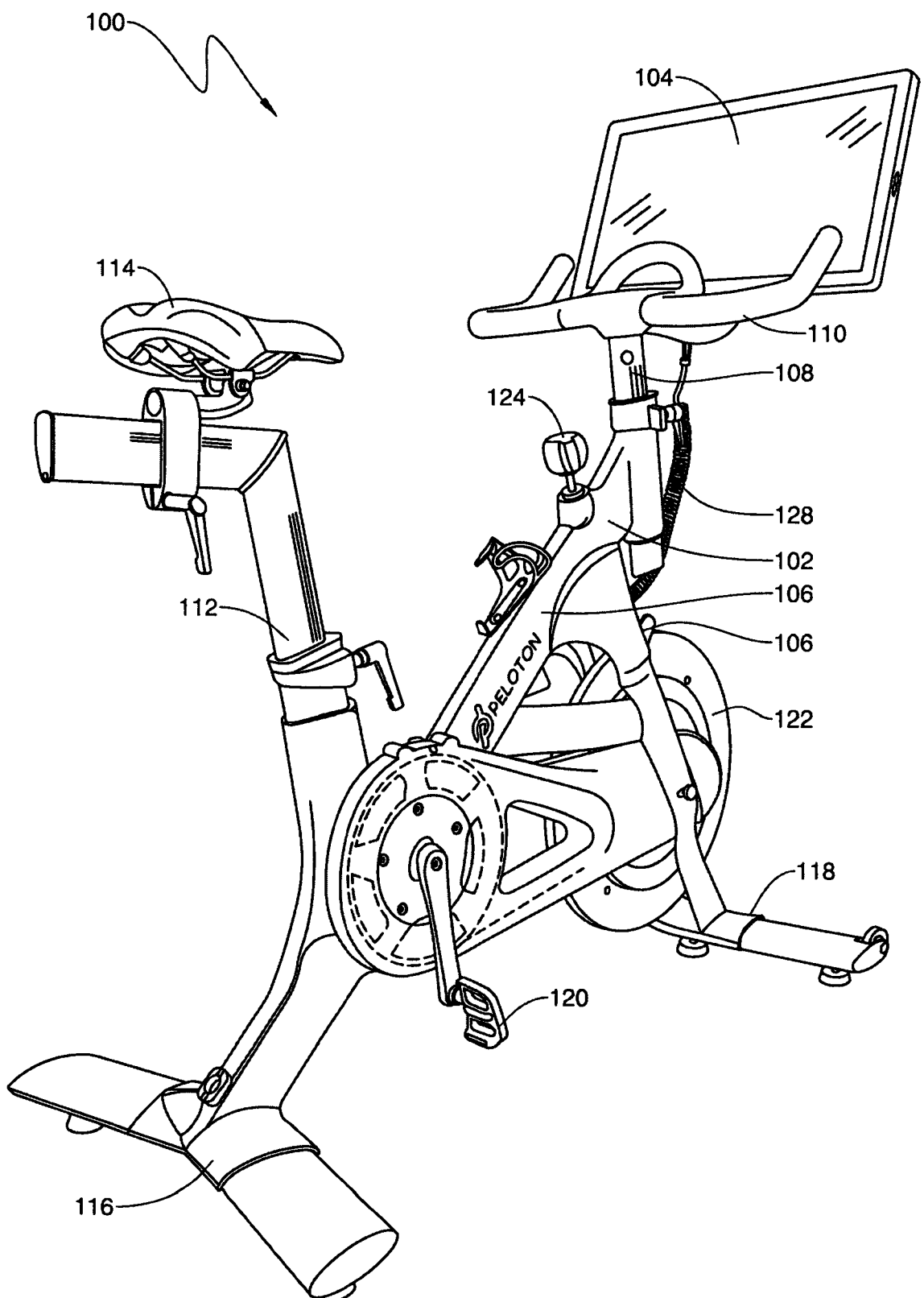
FIG. 1 is a rear perspective view of an exemplary embodiment of a stationary bike as disclosed herein.
Figure 2:
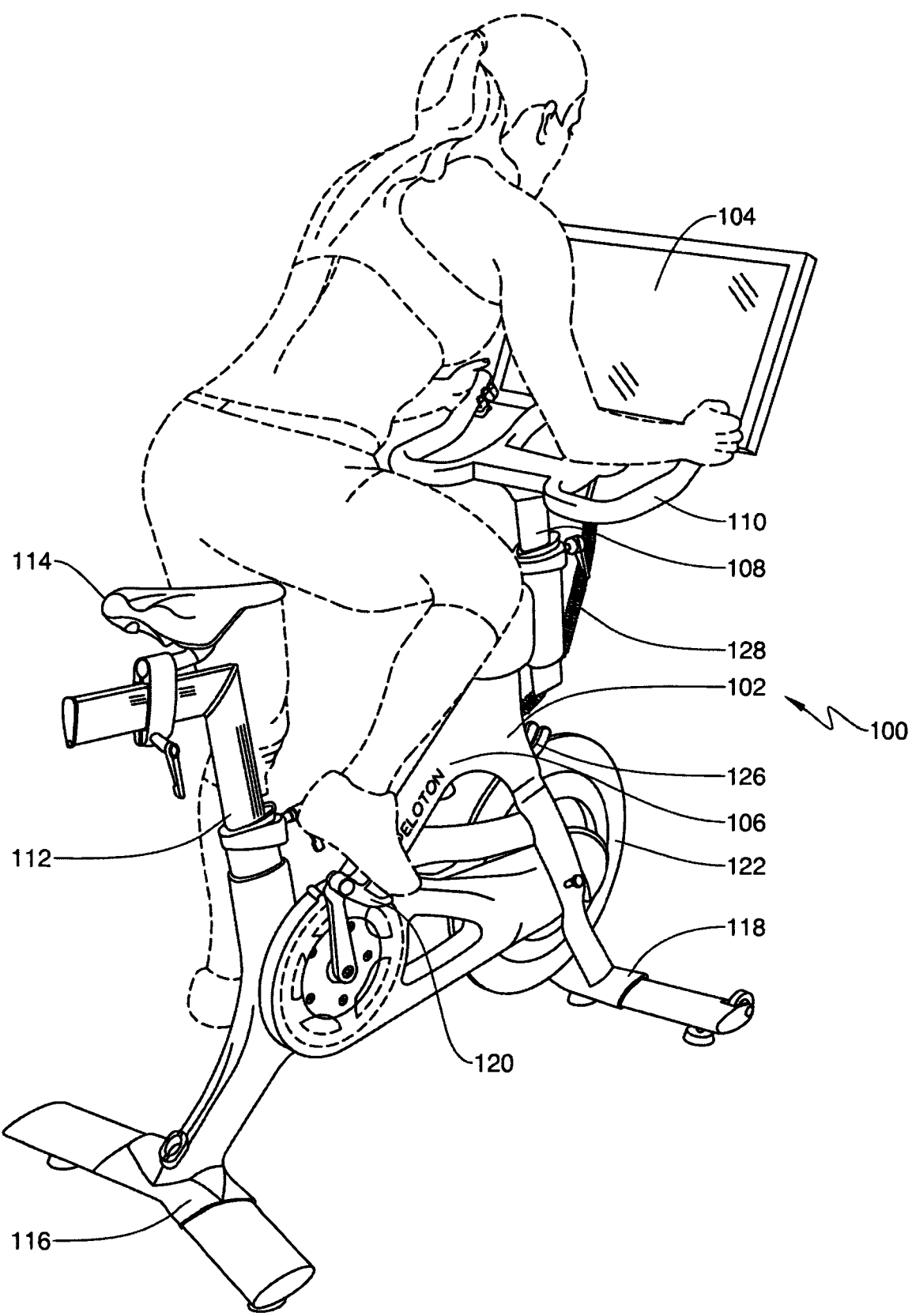
FIG. 2 is a rear perspective view of an exemplary embodiment of a stationary bike as disclosed herein with a rider shown.
Figure 3:
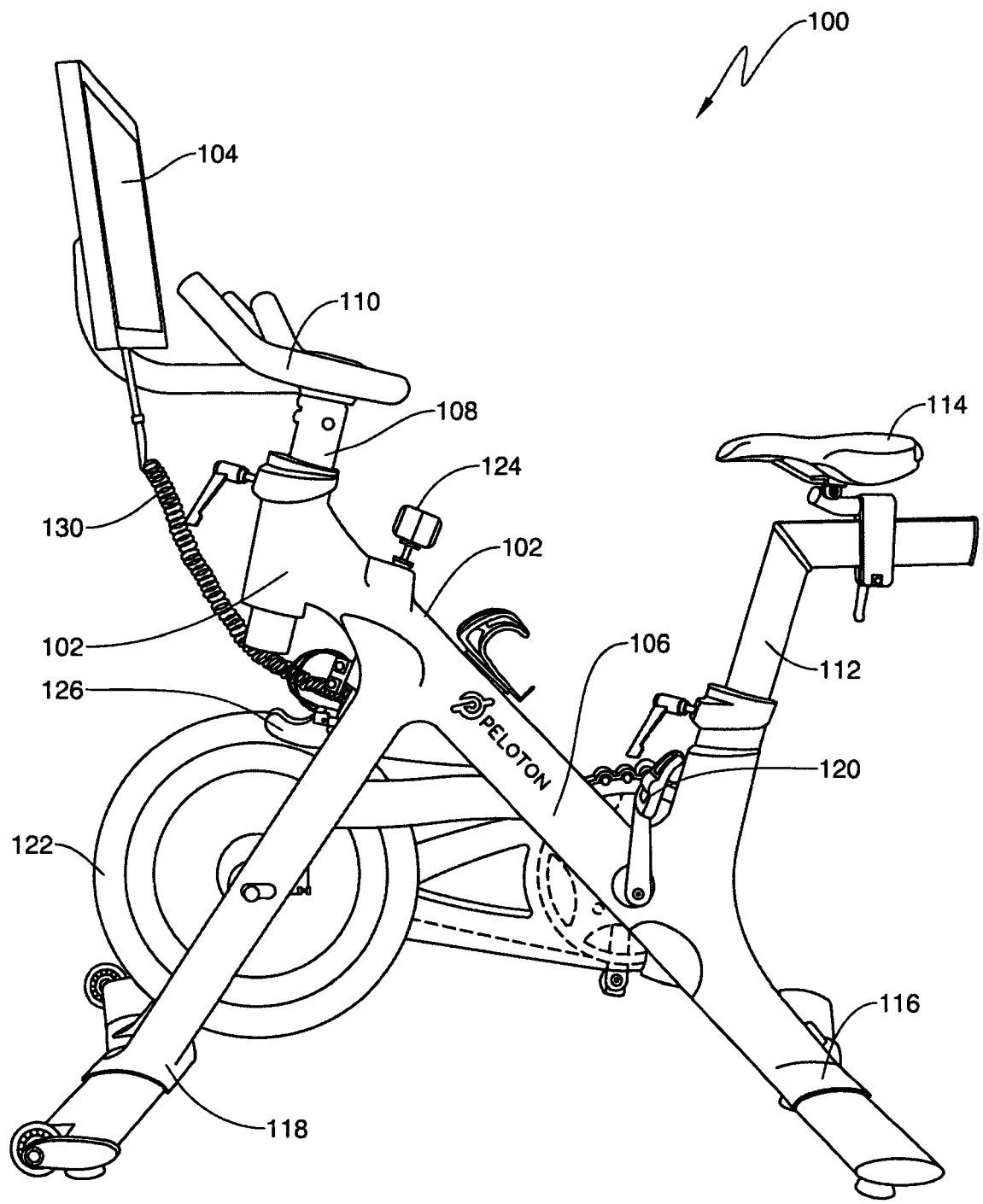
FIG. 3 is a side view of an exemplary embodiment of a stationary bike as disclosed herein.
Figure 4:
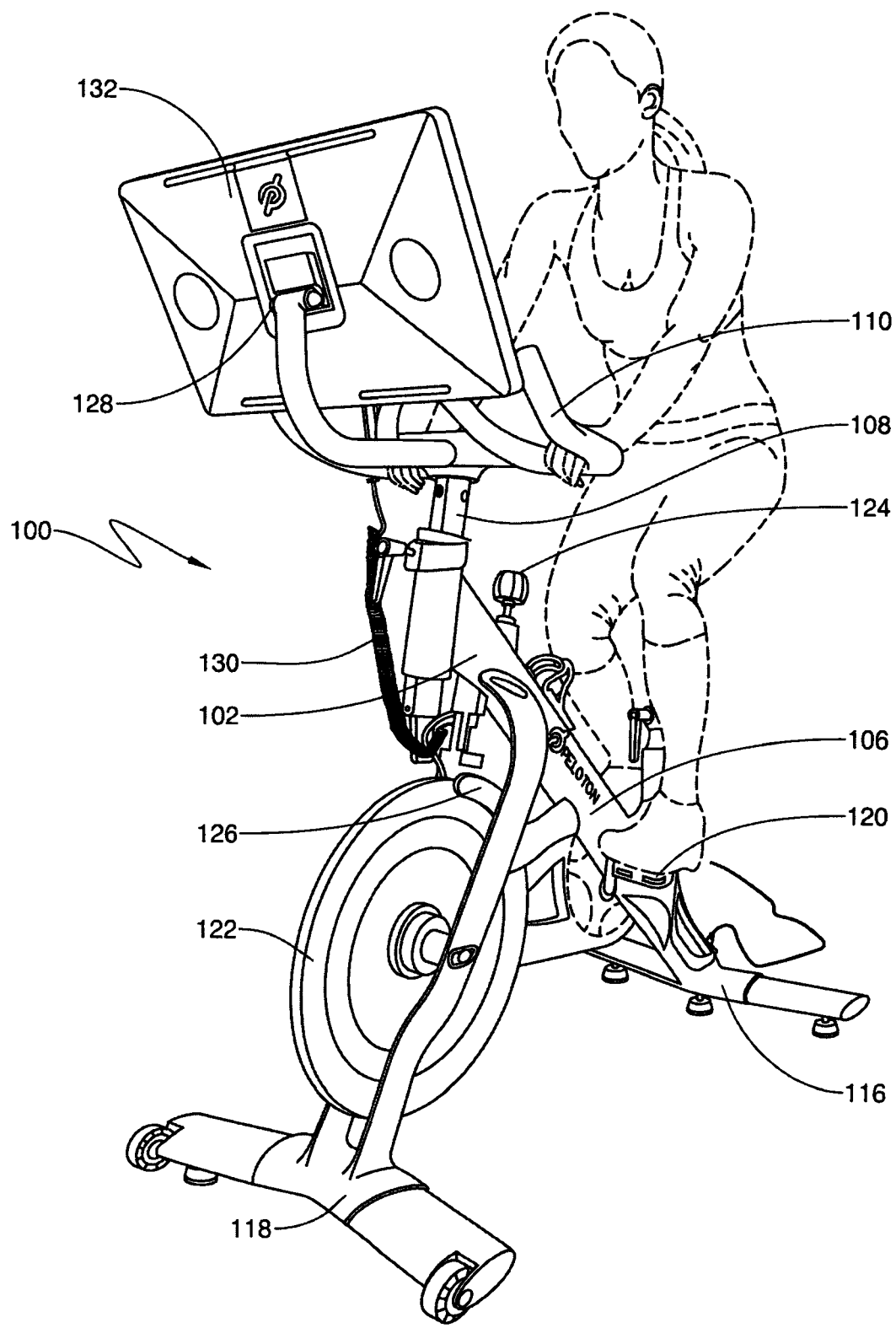
FIG. 4 is a front perspective view of an exemplary embodiment of a stationary bike as disclosed herein with a rider shown.

The following description is presented to enable any person skilled in the art to make and use the invention. For purposes of explanation, specific nomenclature is set forth to provide a thorough understanding of the present invention. Descriptions of specific embodiments or applications are provided only as examples. Various modifications to the embodiments will be readily apparent to those skilled in the art, and general principles defined herein may be applied to other embodiments and applications without departing from the spirit and scope of the invention. Thus, the present invention is not intended to be limited to the embodiments shown, but is to be accorded the widest possible scope consistent with the principles and features disclosed herein.

In various embodiments, the present invention comprises networked exercise systems and methods whereby one or more stationary exercise bicycles, referred to generally herein as stationary bikes, are equipped with an associated local system that allows the user to fully participate in live instructor-led or recorded cycling classes from any location that can access a suitable communications network. The networked exercise systems and methods may include back-end systems with equipment including without limitation servers, digital storage systems, and other hardware as well as software to manage all processing, communications, database, and other functions. The networked exercise systems and methods may also include one or more studio or other recording locations with cameras, microphones, and audio and/or visual outputs where an instructor can lead cycling classes and in some embodiments where live cycling classes can be conducted, and where such classes can be distributed via the communications network. In various embodiments there may be a plurality of recording locations that can interact with each other and/or with any number of individual users.

In various embodiments, the invention provides for full interactivity in all directions. Whether remote or in the same location, instructors can interact with users, users can interact with instructors, and users can interact with other users. Through the disclosed networked exercise system, instructors can solicit feedback from users, and users can provide feedback to the instructor, vote on different choices or options, and communicate regarding their experience. The present invention allows for interaction through all media, including one or more video channels, audio including voice and/or music, and data including a complete range of performance data, vital statistics, chat, voice, and text-based and other communications.

In various embodiments, the invention also allows an unlimited number of remote users to view the same live or recorded content simultaneously, and interact with some or all of the other user viewing same content. Remote users can participate in live cycling classes offered from any recording location, or they can access recorded classes archived in the system database. In various embodiments, a plurality of remote users can simultaneously access the same recorded class and interact with each other in real time, or they can access the same recorded class at different times and share data and communications about their performance or other topics.

Thus, it can be seen that the present invention encompasses networked exercise systems and methods that provide for content creation, content management and distribution, and content consumption. Various aspects of the invention and the potential interactions among such different aspects of the invention will now be described in more detail.

Stationary Bike

Referring generally to FIGS. 1-4, in various exemplary embodiments of the invention, a local system 100 comprises a stationary bike 102 with integrated or connected digital hardware including at least one display screen 104.

In various exemplary embodiments, the stationary bike 102 may comprise a frame 106, a handlebar post 108 to support the handlebars 110, a seat post 112 to support the seat 114, a rear support 116 and a front support 118. Pedals 120 are used to drive a flywheel 122 via a belt, chain, or other drive mechanism. The flywheel 122 may be a heavy metal disc or other appropriate mechanism. In various exemplary embodiments, the force on the pedals necessary to spin the flywheel 122 can be adjusted using a resistance adjustment knob 124. The resistance adjustment knob may directly or indirectly control a device that increases or decreases the resistance of the flywheel to rotation. For example, rotating the resistance adjustment knob clockwise may cause a set of magnets 126 to move relative to the flywheel, increasing its resistance to rotation and increasing the force that the user must apply to the pedals to make the flywheel spin.

The stationary bike 102 may also include various features that allow for adjustment of the position of the seat 114, handlebars 110, etc. In various exemplary embodiments, a display screen 104 may be mounted in front of the user forward of the handlebars. Such display screen may include a hinge 128 or other mechanism to allow for adjustment of the position or orientation of the display screen relative to the rider.

The digital hardware associated with the stationary bike 102 may be connected to or integrated with the stationary bike 102, or it may be located remotely and wirelessly connected to the stationary bike. The display screen 104 may be attached to the stationary bike or it may be mounted separately, but should be positioned to be in the line of sight of a person using the stationary bike. The digital hardware may include digital storage, processing, and communications hardware, software, and/or one or more media input/output devices such as display screens, cameras, microphones, keyboards, touchscreens, headsets, and/or audio speakers. In various exemplary embodiments these components may be integrated with the stationary bike. All communications between and among such components may be multichannel, multi-directional, and wireless or wired, using any appropriate protocol or technology. In various exemplary embodiments, the system may include associated mobile and web-based application programs that provide access to account, performance, and other relevant information to users from local or remote personal computers, laptops, mobile devices, or any other digital device.

In various exemplary embodiments, the stationary bike 102 may be equipped with various sensors that can measure a range of performance metrics from both the stationary bike and the rider, instantaneously and/or over time. For example, the stationary bike may include power measurement sensors such as magnetic resistance power measurement sensors or an eddy current power monitoring system that provides continuous power measurement during use. The stationary bike may also include a wide range of other sensors to measure speed, pedal cadence, flywheel rotational speed, etc. The stationary bike may also include sensors to measure rider heart-rate, respiration, hydration, or any other physical characteristic. Such sensors may communicate with storage and processing systems on the bike, nearby, or at a remote location, using wired or wireless connections.

Hardware and software within the sensors or in a separate package may be provided to calculate and store a wide range of performance information. Relevant performance metrics that may be measured or calculated include distance, speed, resistance, power, total work, pedal cadence, heart rate, respiration, hydration, calorie burn, and/or any custom performance scores that may be developed. Where appropriate, such performance metrics can be calculated as current/instantaneous values, maximum, minimum, average, or total over time, or using any other statistical analysis. Trends can also be determined, stored, and displayed to the user, the instructor, and/or other users. A user interface may provide for the user to control the language, units, and other characteristics for the various information displayed.

Display and User Interface

Referring generally to FIGS. 1-12, in various exemplary embodiments the stationary bike 102 may be equipped with one or more large display screens 104, cameras, microphones, and speakers or other audio outputs.

The display screen(s) 104 may be mounted directly to the stationary bike 102 or otherwise placed within the viewing area of the user. In various exemplary embodiments, at least one display screen is integrated into or attached to the stationary bike, and is positioned in front of the rider generally centered on the handlebars 110 of the stationary bike as illustrated in the figures. Various mechanisms can be used to allow the user to customize the position of the display screen(s).

In an exemplary embodiment, a display screen 104 may be attached to the stationary bike 102 via a curved structure extending up and forward from the front stem of the frame 106. The curved structure may include a slot or aperture through it and extending along a portion of the length of the curved structure. A mounting post or similar structure on the display screen may attach to the curved structure, such as by a pin that passes through the mounting post or structure and the curved structure. In an exemplary embodiment, the pin may have a mechanism such as threads that allow it to be tightened to hold and lock the mounting post or structure at a particular location and position.

Display screen 104 may be driven by a user input device such as a touchscreen, mouse, or other device. In various exemplary embodiments a touchscreen display is mounted on the stationary bike generally centered between the handlebars and located just below the handlebars. The display screen may be any size, but optimally is large enough and oriented to allow the display of a range of information including one or more video streams, a range of performance metrics for the user and others, and a range of different controls.

In various exemplary embodiments the user can use a touchscreen or other interface to selectively present a range of different information on the screen including live and/or archived video, performance data, and other user and system information. The user interface can provide a wide range of control and informational windows that can be accessed and removed individually and/or as a group by a click, touch, or gesture. In various exemplary embodiments, such windows may provide information about the user's own performance and/or the performance of other participants in the same class both past and present.

The user interface can be used to access member information, login and logout of the system, access live content such as live exercise classes and archived content (referred to in the Figures as "Rides on-demand"). User information may be displayed in a variety of formats and may include historical and current performance and account information, social networking links and information, achievements, etc. The user interface can also be used to access the system to update profile or member information, manage account settings such as information sharing, and control device settings.

Referring to FIGS. 5-12, a user interface 200 may be presented on the display screen 104 to allow the user to manage their experience, including selecting information to be displayed and arranging how such information is displayed on their system. The user interface may present multiple types of information overlaid such that different types of information can be selected or deselected easily by the user. For example, performance information may be displayed over video content using translucent or partially transparent elements so the video behind the information elements can be seen together with the information itself.

Figure 5:
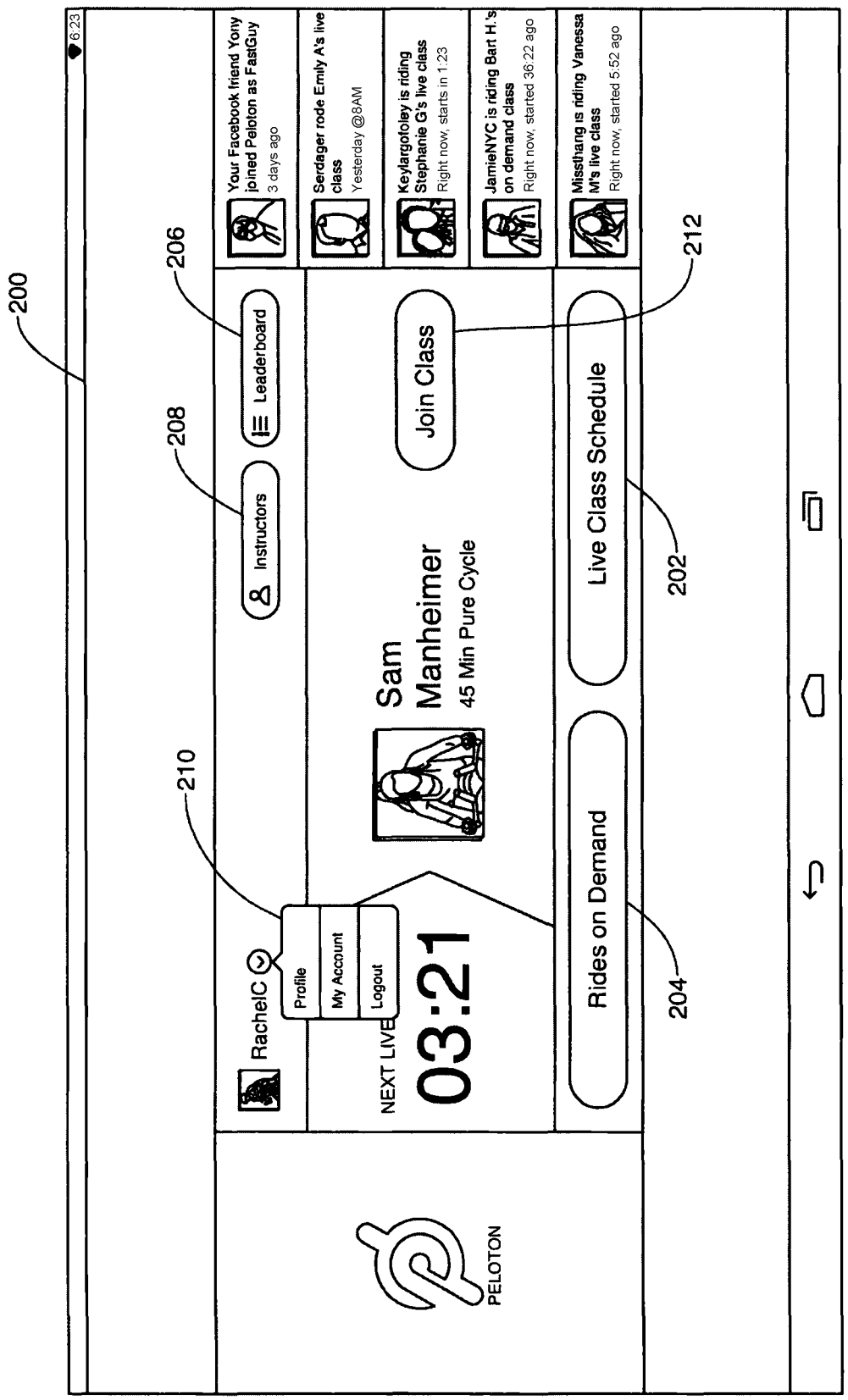
FIG. 5 is an illustration of an exemplary embodiment of a user interface home screen as disclosed herein.

The user interface 200 may present a variety of screens to the user, which the user can move among quickly using the provided user input device, including by touching if a touchscreen is used. In various exemplary embodiments, the user interface may provide a home screen that provides basic information about the system and available options. Referring to FIG. 5, such a home screen may provide direct links to information such as scheduled classes 202, archived classes 204, a leaderboard 206, instructors 208, and/or profile and account information 210. The screen may also provide direct links to content such as a link to join a particular class 212. The user can navigate among the different screens in the user interface by selecting such links using the applicable input device such as by touching the touchscreen at the indicated location, or by swiping to bring on a new screen. The user interface may also provide other information relevant to the user such as social network information, and navigation buttons that allow the user to move quickly among the different screens in the user interface.

Figure 6:
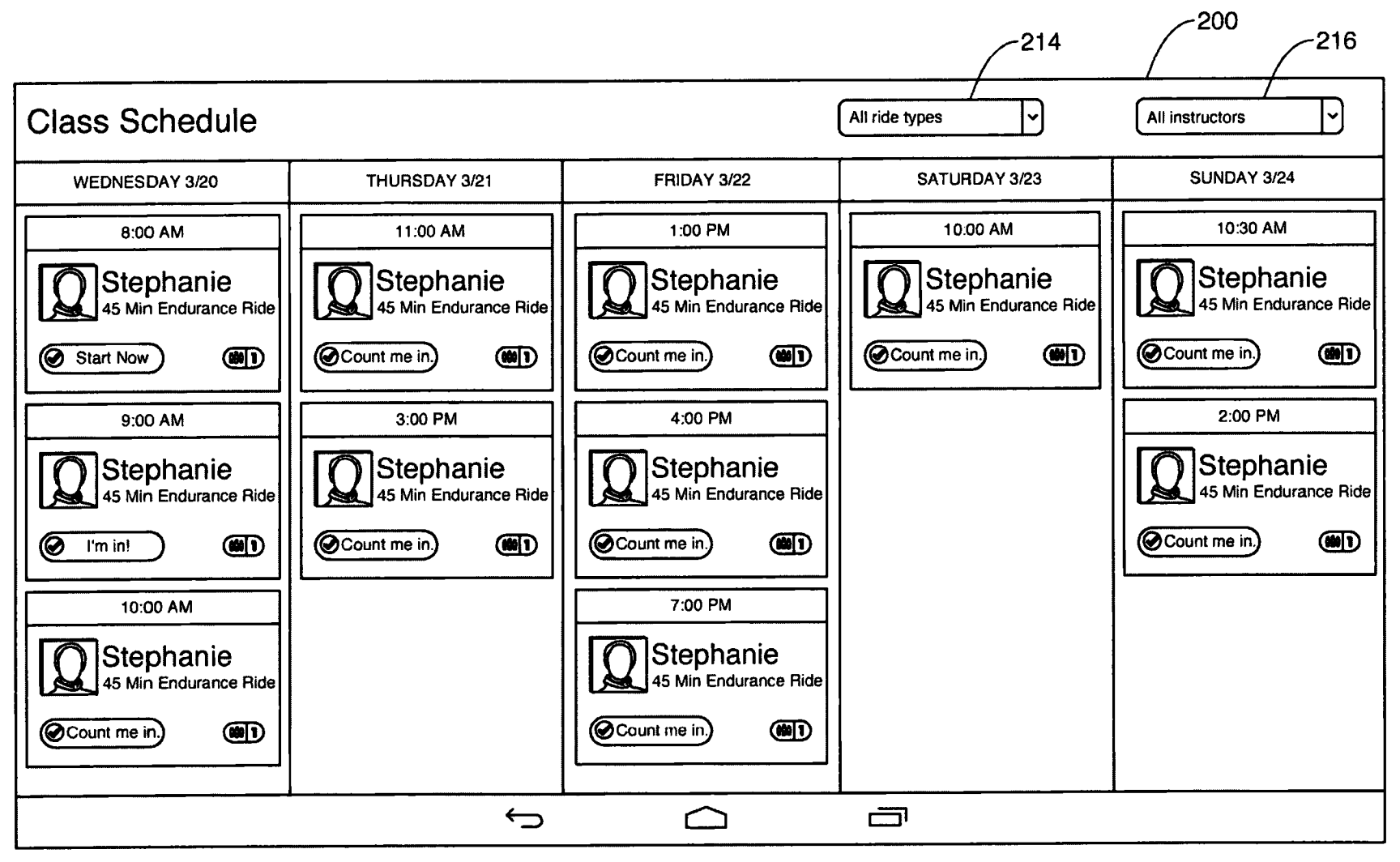

In various exemplary embodiments, the user can select among both live and archived content. For example, if the user selects scheduled classes 202, they may be presented with a screen showing the schedule of upcoming classes. FIG. 6 shows an exemplary schedule of upcoming classes presented on the screen through the user interface 200, with classes shown like a traditional calendar. Drop-down or other display features allow users to find classes by ride type 214, instructor 216, or by any other appropriate category. The user interface 200 allows users to select future classes or to start a class that is underway or about to begin. The class schedule may be presented in any suitable format, including calendar, list, or any other appropriate layout.

Figure 7:
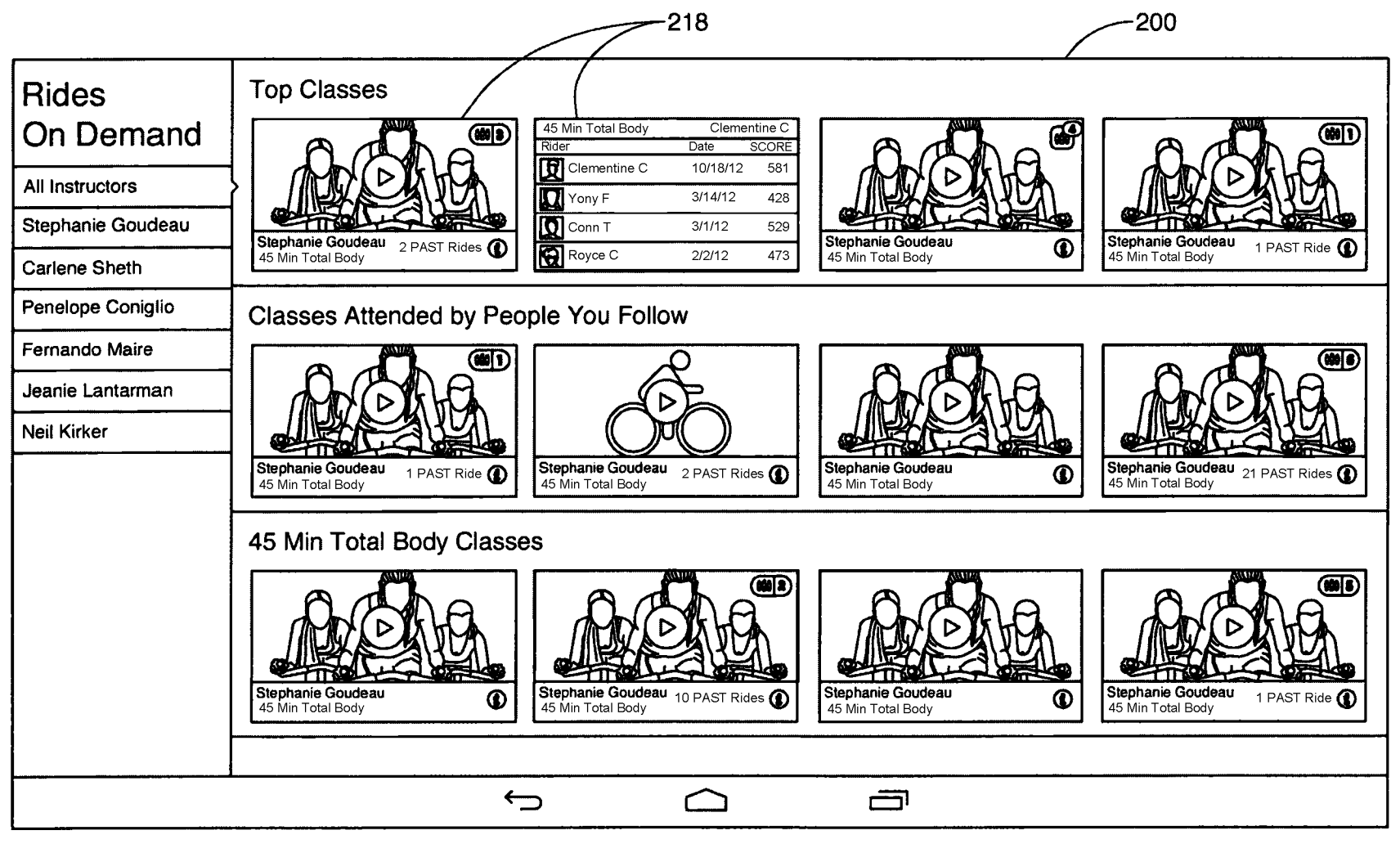

In various exemplary embodiments, if the user selects archived classes 204, they may be presented with a screen showing available archived classes sorted by any appropriate category. FIG. 7 shows an exemplary display of archived classes. Thumbnails or icons 218 representing archived classes may be displayed in any suitable format, and may include information on how many times the user has ridden that class in the past or other performance or class-related information. A class may be accessed by selecting a particular thumbnail or icon.

Figure 8:
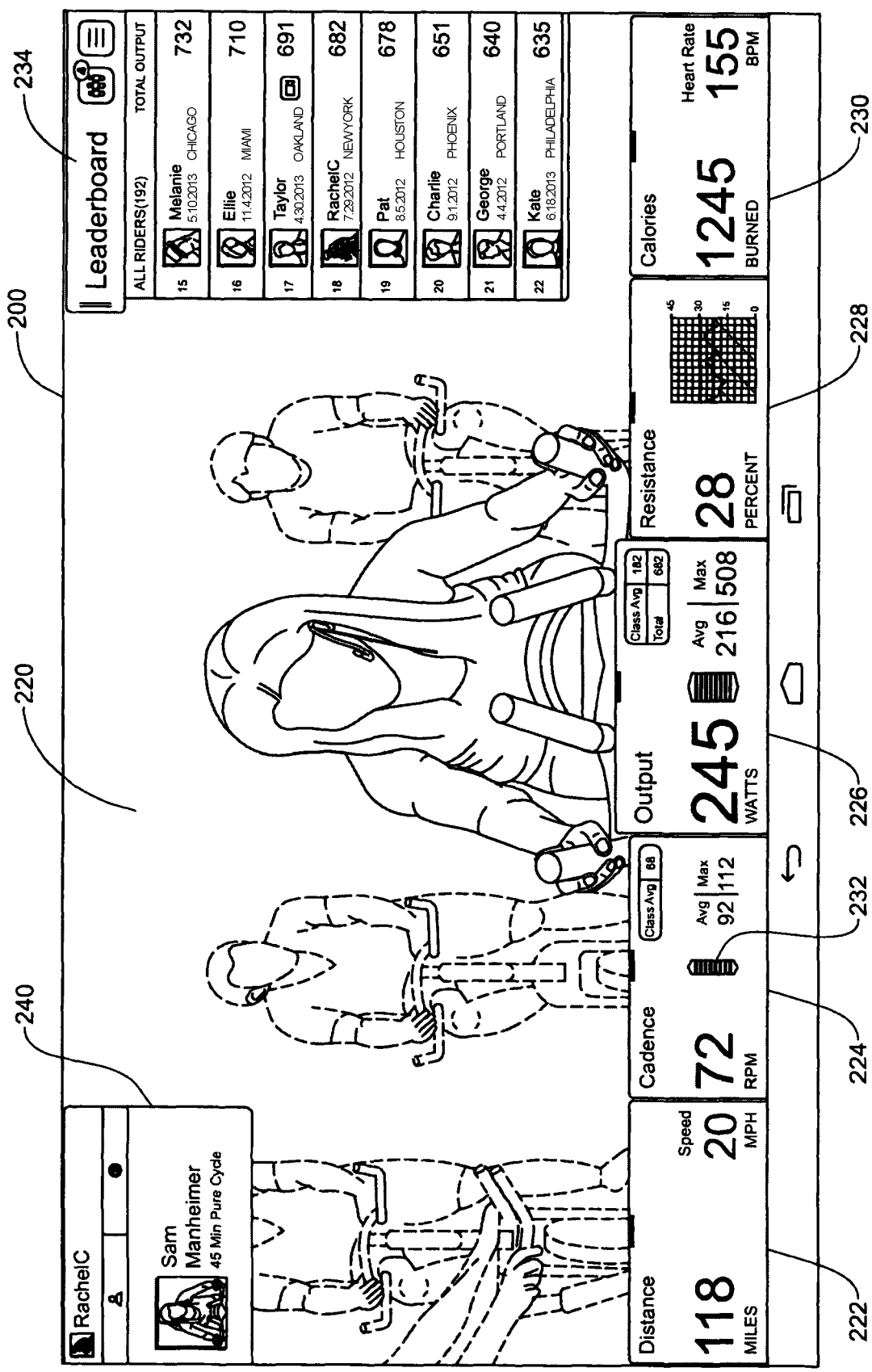
FIG. 8 is an illustration of an exemplary embodiment of a user interface screen displaying a live or on-demand cycling class underway.
Figure 9:
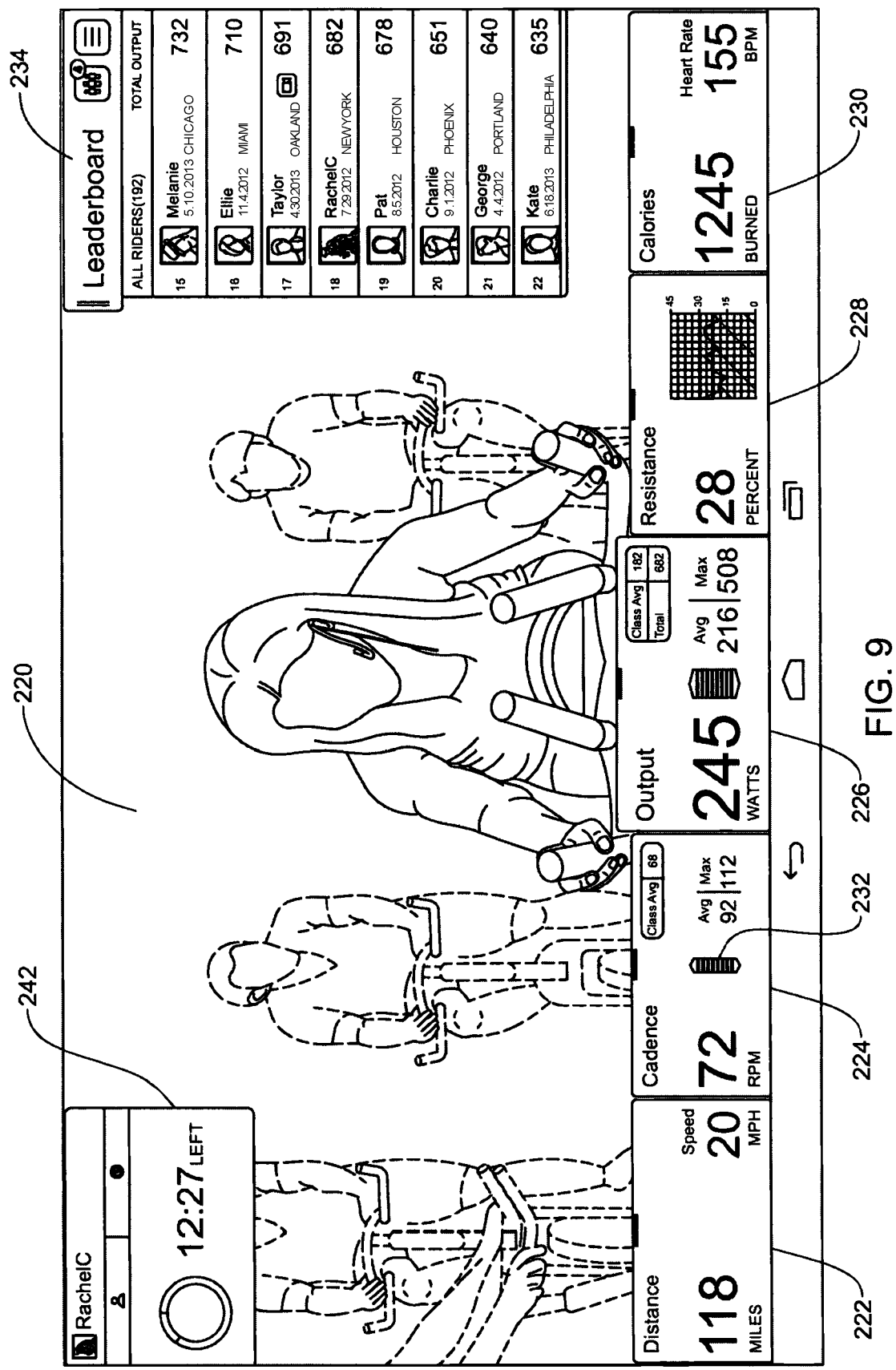
FIG. 9 is an illustration of an exemplary embodiment of a user interface screen displaying a live or on-demand cycling class underway.
Figure 10:
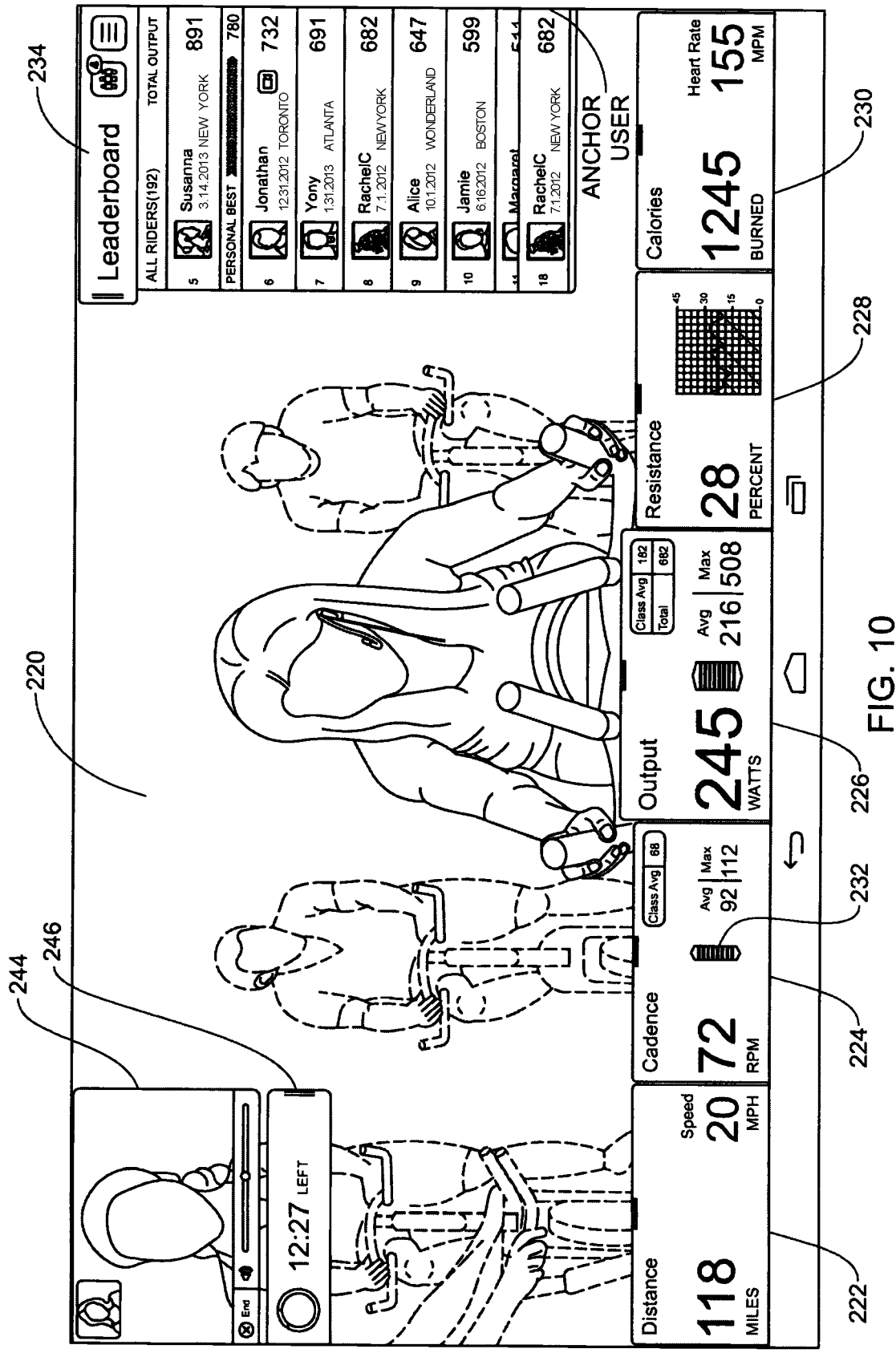
FIG. 10 is an illustration of an exemplary embodiment of a user interface screen displaying a live or on-demand cycling class underway with a live video chat open in a secondary window and the leaderboard scrolling.

Referring to FIGS. 8-10, when a class is being playing on the display screen 104 through the user interface 200, in various exemplary embodiments the primary video feed may be shown as the background video full-screen or in a sub-window on the screen. Information elements may be provided on different parts of the display screen to indicate any performance metrics, including time ridden, elapsed time, time left, distance, speed, resistance, power, total work, pedal cadence, heart rate, respiration, hydration, calorie burn, and/or any custom performance scores that may be developed. The displayed information may also include the trend or relationship between different performance metrics. For example, the display can indicate a particular metric in a color that indicates current performance compared to average performance for a class or over time, such as red to indicate that current performance is below average or green to indicate above average performance. Trends or relative performance can also be shown using color and graphics, such as a red down arrow to show that current performance is below average.

FIGS. 8-10 show a primary window 220 showing the live or archived class that the user selected. In various exemplary embodiments, performance metric windows 222, 224, 226, 228, and 230 may show specific performance metrics for the user's current ride, past rides, or other performance information. Such performance metric windows may be presented anywhere on the display screen, and may be user selectable such that they can be displayed or removed by a screen touch or gesture. As shown in FIG. 8, window 222 displays distance and speed. Window 224 displays current pedal cadence, along with the user's average and maximum cadence and the class average, and an indicator arrow 232 showing whether the user's cadence is increasing or decreasing. Window 226 shows power output in watts, together with average output, maximum output, class average, and total output, along with a similar indicator arrow. Window 228 shows resistance as both a number and graphically, and window 230 shows calories burned and heart rate.

The user interface may allow the user to toggle between display of maximum, average, and total results for different performance metrics. The user interface may also allow the user to hide or display information elements, including performance metrics, video streams, user information, etc. all at once or individually. Performance information can also be displayed in various display bars that can be hidden or displayed as a group or individually. The user interface may provide for complete controls for audio volume, inputs, and outputs as well as display output characteristics.

A leaderboard 234 may also be displayed to allow the user to see their performance in comparison to others taking the same class. In various exemplary embodiments, a leaderboard may be configured to display the relative performance of all riders, or one or more subgroups of riders. For example, the user may be able to select a leaderboard that shows the performance of riders in a particular age group, male riders, female riders, male riders in a particular age group, riders in a particular geographic area, etc. Users may be provided with the ability to deselect the leaderboard entirely and remove it from the screen. In various exemplary embodiments, the system may incorporate various social networking aspects such as allowing the user to follow other riders, or to create groups or circles of riders. User lists and information may be accessed, sorted, filtered, and used in a wide range of different ways. For example, other users can be sorted, grouped and/or classified based on any characteristic including personal information such as age, gender, weight, or based on performance such as current power output, speed, or a custom score.

The leaderboard 234 may be fully interactive, allowing the user to scroll up and down through the rider rankings, and to select a rider to access their detailed performance data, create a connection such as choosing to follow that rider, or establish direct communication such as through an audio and/or video connection. The leaderboard may also display the user's personal best performance in the same or a comparable class, to allow the user to compare their current performance to their previous personal best. The leaderboard may also highlight certain riders, such as those that the user follows, or provide other visual cues to indicate a connection or provide other information about a particular entry on the leaderboard.

In various exemplary embodiments, the leaderboard will also allow the user to view their position and performance information at all times while scrolling through the leaderboard. For example, as shown in FIG. 10 if the user scrolls up toward the top of the leaderboard such as by dragging their fingers upward on the touchscreen, when the user's window reaches the bottom of the leaderboard, it will lock in position and the rest of the leaderboard will scroll underneath it. Similarly, if the user scrolls down toward the bottom of the leaderboard, when the user's window reaches the top of the leaderboard, it will lock in position and the rest of the leaderboard will continue to scroll underneath it.

In various exemplary embodiments, the system calculates and displays one or more custom scores to describe one or more aspects of the users' performance. One example of such a custom score would be a decimal number calculated for a particular class or user session. Such a score could also be calculated using performance data from some or all classes or sessions over a particular period of time. In an exemplary embodiment, the custom score takes into account the amount of time ridden, total work during that time period, and number of classes in a given time period.

In various exemplary embodiments, performance information about other users may be presented on the leaderboard 234 or in any other format, including formats that can be sorted by relevant performance parameters. Users may elect whether or not to make their performance available to all users, select users, and/or instructors, or to maintain it as private so that no one else can view it.

In various exemplary embodiments the user interface may also present one or more video streams from a range of different sources. For example, one video stream may be the live or archived class content shown in the primary window, while one or more additional video streams may be displayed in other windows on the screen display 104. The various video streams may include live or recorded streaming instructor video or any other video content, including one or more live video chat streams.

The user interface may also provide additional windows that can be used to display a range of content including additional performance data, information about the class, instructor, other riders, etc., or secondary video streams. Such additional windows can allow the user to see a range of information regarding other current or past participants to compare performance, and open or close voice or video chat streams or other communication channels. In various exemplary embodiments the user can simultaneously access other content including movies, television channels, online channels, etc. Referring to FIGS. 8 through 10, secondary window 240, 242, 244 may display a range of information and content. In FIG. 8, secondary window 240 displays the name of the user, the name of the current class and basic class information. In FIG. 9, secondary window 242 displays the name of the user and the amount of time remaining in the current class. In FIG. 10, secondary window 244 displays a video chat session, while the time remaining is displayed in a second secondary window 246.

Stationary Bike Local System

In various exemplary embodiments, the local system 100 comprises the stationary bike 102 and a range of associated sensing, data storage, processing, and communications components and devices either onboard the stationary bike itself or located near the stationary bike. This local system may communicate with one or more remote servers through wired or wireless connections using any suitable network or protocol.

In various exemplary embodiments, the stationary bike 102 may be equipped with various sensors to measure and/or store data relating to user performance metrics such as speed, resistance, power, cadence, heart rate, hydration level, etc. The stationary bike may also be equipped with or connected to various data inputs such as touchscreens, video cameras, and/or microphones. These sensors and other inputs can communicate with local and/or remote processing and storage devices via any suitable communications protocol and network, using any suitable connection including wired or wireless connections. In various exemplary embodiments, local communication may be managed using a variety of techniques. For example, local communication may be managed using wired transport with a serial protocol to communicate between sensors and the console. Local communication may also be managed using a wireless communication protocol such as the ANT or ANT+ protocol. ANT is a 2.4 GHz practical wireless networking protocol and embedded system solution specifically designed for wireless sensor networks (WSN) that require ultra low power. Advantages include extremely compact architecture, network flexibility and scalability, case of use and low system cost. Various combinations of wired and wireless local communication may also be used.

Access to any appropriate communications network such as the internet may be used to provide information to and receive information from other stationary bikes or other resources such as a backend system or platform. In various exemplary embodiments, the local system 100 can access and display information relating to other users either directly through a distributed platform or indirectly through a central platform regardless of their location. Such other users may be present at the same location or a nearby location, or they may be at a remote location.

In various exemplary embodiments, the local system 100 may include an integrated onboard computer system comprising a display screen 104, one or more processors, data storage, and communications components. The processing, data storage, and communications components may be located within housing 132 to form a single integrated onboard computer and display screen, or they may be separately housed locally on or near the stationary bike. The local system may include one or more video cameras, microphones, and/or audio outputs such as speakers or audio connectors.

In various exemplary embodiments, the local system 100 receives a variety of data inputs from sensors on the stationary bike 102 or the rider, and processes and stores that data. This data can be displayed to the user as discussed above, stored locally, and/or shared via any suitable network with other local systems and/or with a central platform via any appropriate network.

Figure 11:
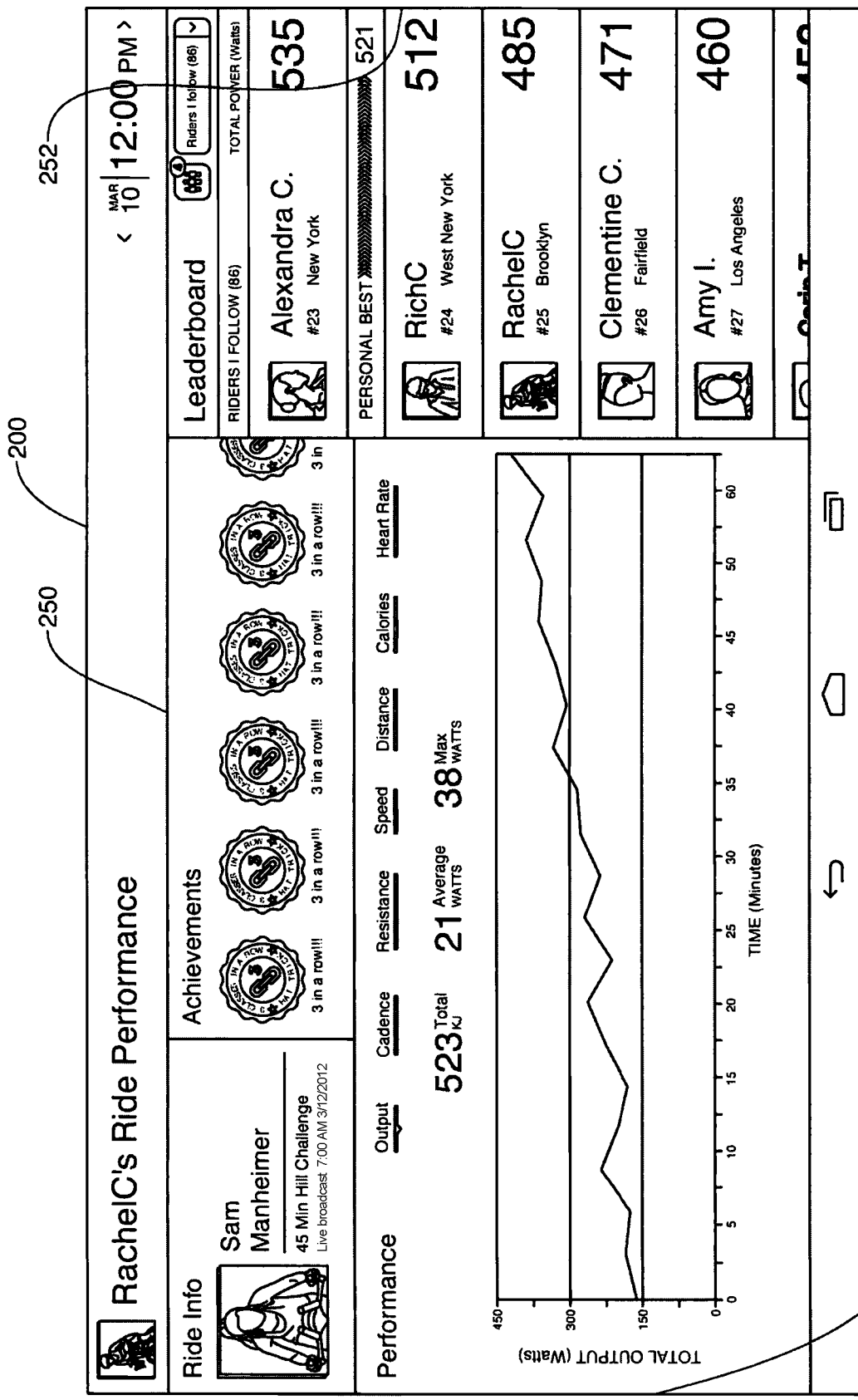
FIG. 11 is an illustration of an exemplary embodiment of a user interface screen displaying user performance and other information.
Figure 12:
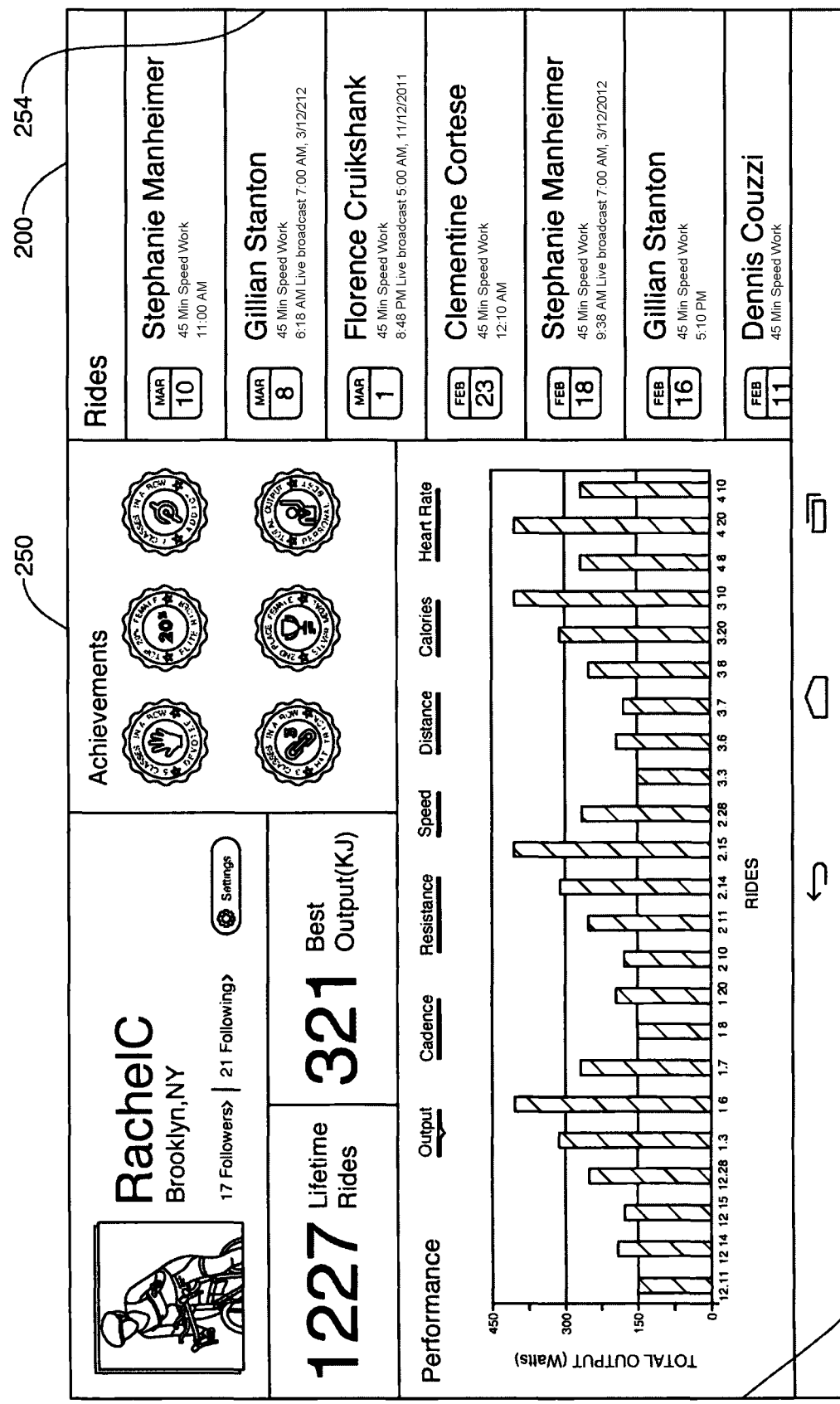
FIG. 12 is an illustration of an exemplary embodiment of a user interface screen displaying user performance and other information.
Figure 13:
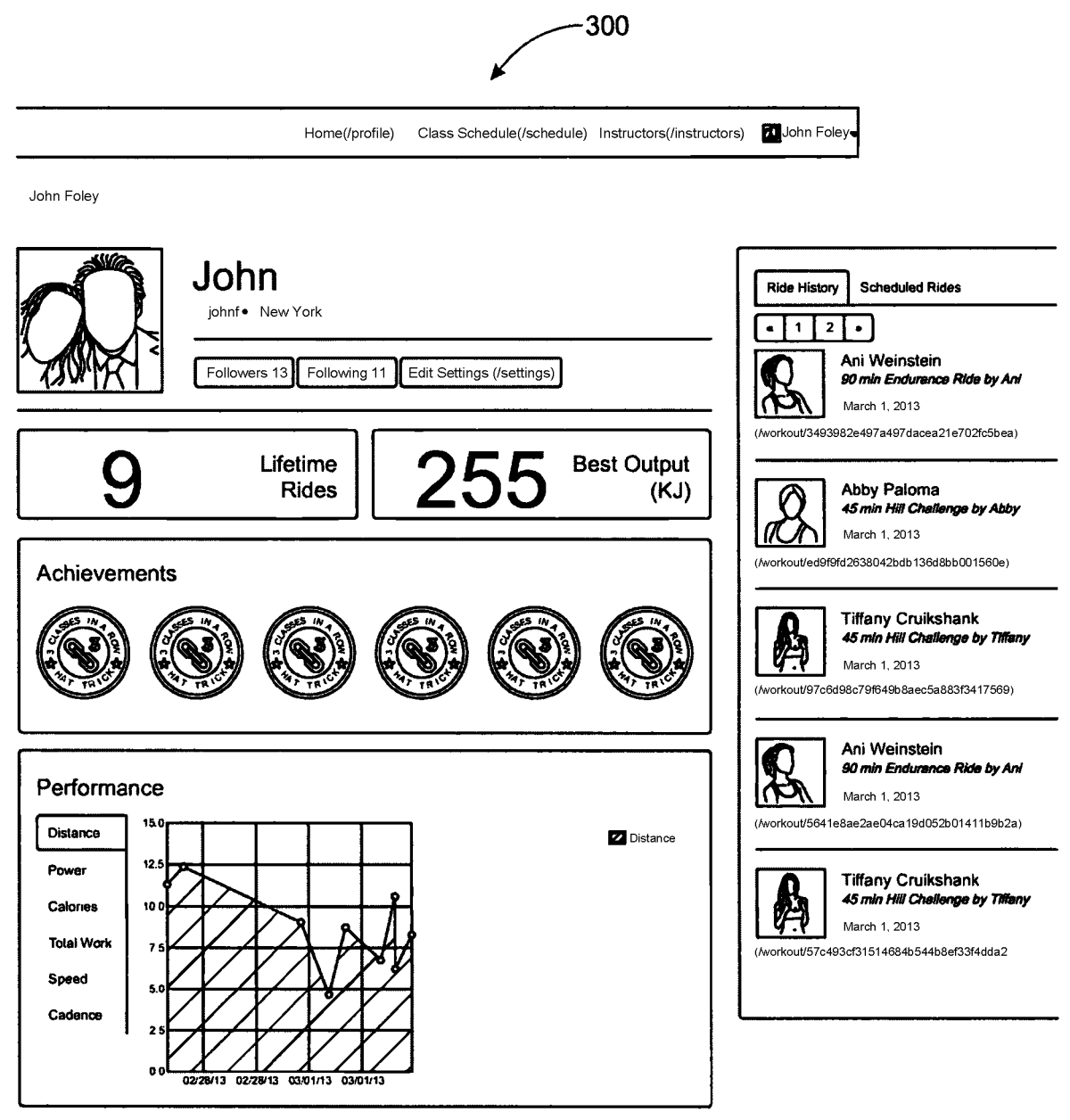
Figure 14:
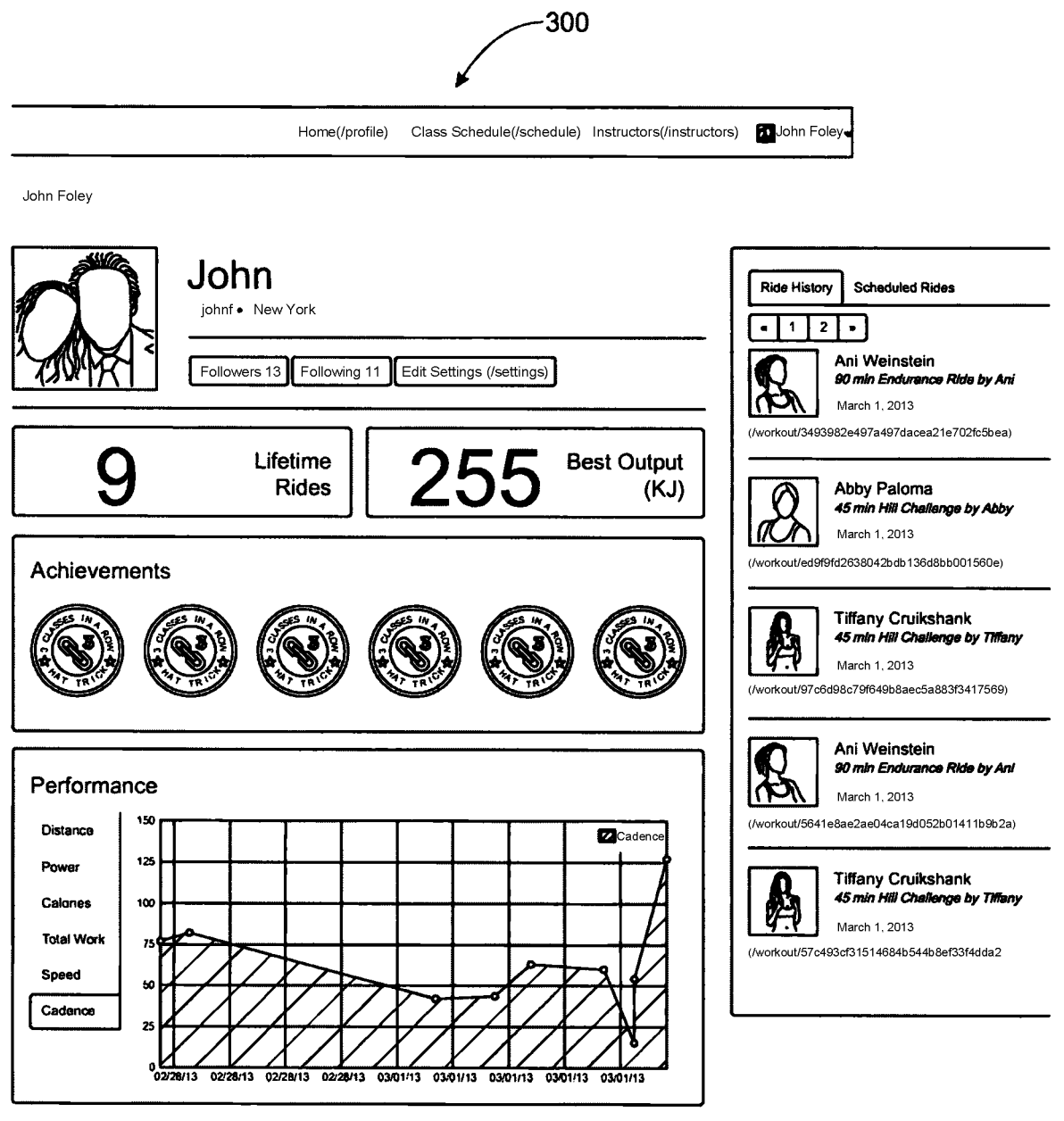

Referring to FIGS. 11 and 12, the user interface 200 may be used to access local system 100 data as well as data maintained remotely. In various exemplary embodiments, the user interface may present one or more windows that may display to the user information about their current or past performances 248 using a range of metrics, their achievements, 250, their position on a leaderboard as compared to a peer group 252, their planned activities 254, their social network, etc. The user interface may be implemented through a local or remote system. In various exemplary embodiments, the user interface may be run through a local program or application using the local operating system such as an Android or iOS application, or via a browser based system. Referring to FIGS. 13 and 14, such information may also be accessed remotely via any suitable network such as the internet. In various exemplary embodiments, users may be able to access a website 500 from any digital device that can provide access to a complete range of user information. Users may be able to review historical information, communicate with other riders, schedule classes, access instructor information, etc. through such a website.

Content Creation and Distribution

Content for delivery to users including live and archived exercise classes may be created and stored in various local or remote locations and shared across the networked exercise system. This overview of such a networked exercise system is exemplary only and it will be readily understood that the present invention can be implemented through a variety of different system architectures using centralized or distributed content creation and distribution techniques.

In various exemplary embodiments, the networked exercise system is managed through one or more networked backend servers and includes various databases for storage of user information, system information, performance information, archived content, etc. Users' local systems 100 are in communication with the networked backend servers via any appropriate network, including without limitation the internet. As an example of an alternative distribution approach, in various exemplary embodiments the backend servers could be eliminated and data could be communicated throughout the system in a distributed or peer-to-peer manner rather than via a central server network. In such a system, performance data may be broken up into small packets or "pieces" and distributed among user devices such that complete data sets are quickly distributed to all devices for display as required.

Content for distribution through the network can be created in a variety of different ways. Content recording locations may include professional content recording studios or amateur and home-based locations. In various exemplary embodiments, recording studios may include space for live, instructor-led, in-studio cycling classes with live studio participation or may be dedicated studios with no live, in-studio participation. Recording equipment including microphones and one or more cameras can be used to capture the instructor and/or participants during the class. Multiple cameras can provide different views and 3D cameras can be used to create 3D content. In various exemplary embodiments, content may also be generated locally by users. For example, stationary bikes 102 may be equipped with recording equipment including microphones and cameras. Users may generate live or recorded classes that can be transmitted, stored in the system, and distributed throughout the network.

Figure 15:
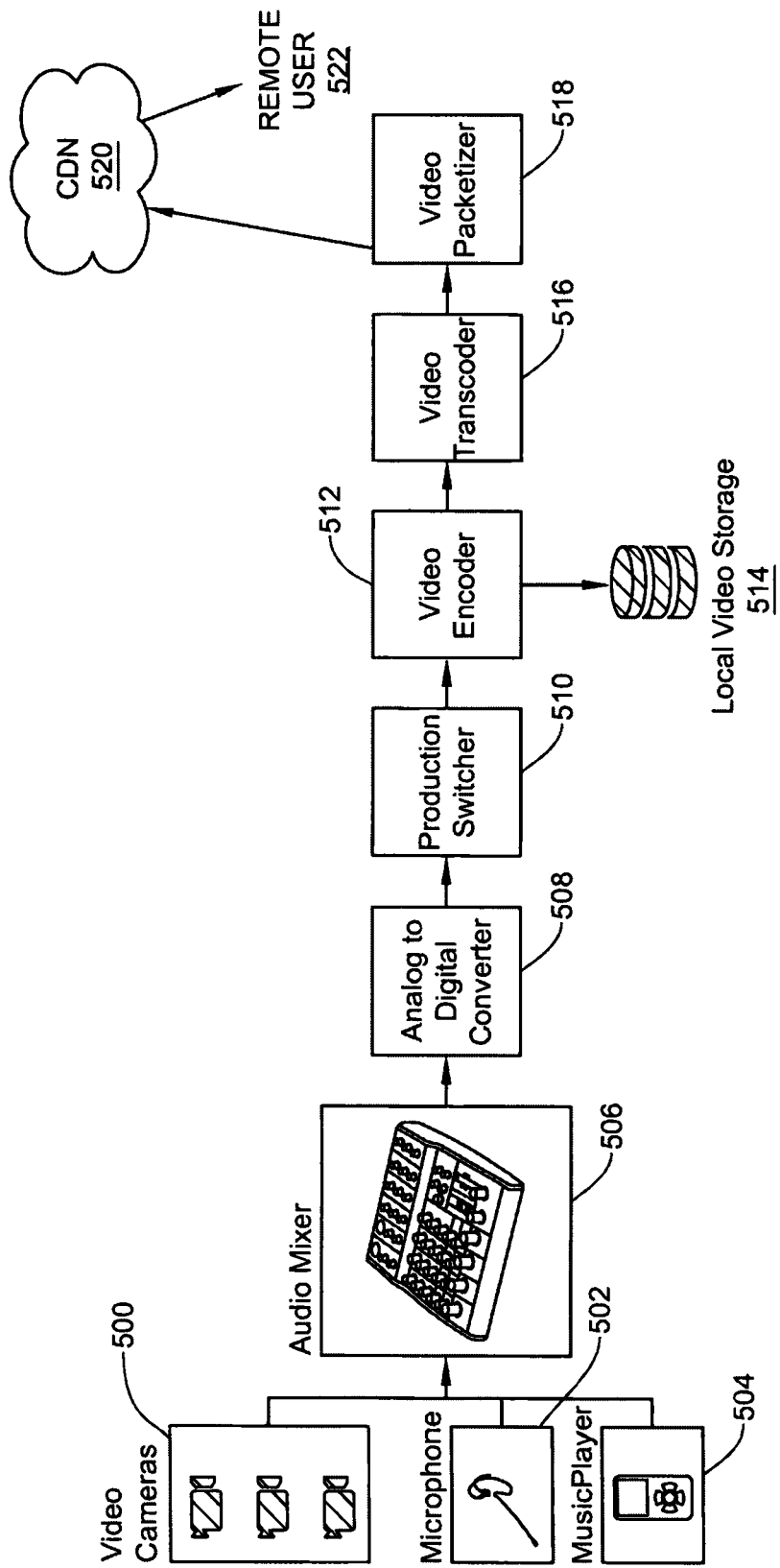
FIG. 15 is a schematic showing an exemplary embodiment of the data flow for content creation and distribution.

Referring to FIG. 15, class content may be generated using one or more video cameras 500, an instructor microphone 502, and a music player 504 as inputs to an audio mixer 506. The audio mixer outputs content to an analog to digital converter 508, which provides converted data to a production switcher 510. The production switcher sends the production video to a video encoder 512, which stores the encoded video to a local storage device 514, and sends it to a video transcoder 516. The video transcoder outputs the transcoded data to a video packetizer 518, which then sends the packetized data stream out through the content distribution network 520 to remote system users 522. In various exemplary embodiments, instructors and/or users may be provided with access to a content creation platform that they can use to help them create content. Such a platform may provide tools for selecting and editing music, managing volume controls, pushing out chat or other communications to users.

As described above, through the user interface on their stationary bike 102, users may access lists, calendars, and schedules of live and recorded cycling classes available for delivery through the display screen 104. In various exemplary embodiments, once the user selects a class, the local system accesses and displays a primary data stream for the class. This primary data stream may include video, music, voice, text, or any other data, and may represent a live or previously recorded cycling class. The local system may be equipped for hardware video accelerated encoding/decoding to manage high-definition video quality at up to 1080 pixels based on existing technology. The local system may automatically adjust bitrate/quality of the data stream for the class in order to bring rider the highest quality video according to user's bandwidth/hardware limitations.

In various exemplary embodiments, the networked exercise systems and methods may include multi-directional communication and data transfer capabilities that allow video, audio, voice, and data sharing among all users and/or instructors. This allows users to access and display multi-directional video and audio streams from the instructor and/or other users regardless of location, and to establish direct communications with other users to have private or conferenced video and/or audio communications during live or recorded classes. Such data streams can be established through the local system 100 for presentation via the display screen 104 the primary window or in a secondary window such as that shown in FIG. 10 at secondary window 244. In various exemplary embodiments, users can manage multiple data streams to select and control inputs and outputs. The local system may allow the user to control the volume of primary audio stream for the class as well as other audio channels for different users or even unrelated audio streams such as telephone calls or their own music selections. For example, this would allow a user to turn down the instructor volume to facilitate a conversation with other users.

For live classes, in various exemplary embodiments the instructor may have the ability to communicate with the entire class simultaneously or to contact individual users, and solicit feedback from all users regardless of location in real-time. For example, instructors could ask users verbally, or text a pop-up message to users, seeking feedback on difficulty level, music choice, terrain, etc. Users could then respond through their onboard system by selecting an appropriate response, or providing verbal feedback. This allows instructors to use crowdsourcing to tailor a class to the needs of the participants, and to improve their classes by soliciting feedback or voting on particular class features or elements.

In various exemplary embodiments, instructors may also be able to set performance targets, and the system can measure and display to the user and the instructor their performance relative to the target. For example, the instructor may set target metrics e.g. target power and cadence, then display this next to users' readings with a color coding to indicate whether or not the user is meeting this target. The system may allow the instructor to remotely adjust bike settings for individual users.

In various exemplary embodiments, users can control access to their own information, including sensor data, performance metrics, and personal information. Such data can be held at the local system, transmitted for storage and management by a remote system and shared with other users, or stored remotely but not shared with other users. Users may also elect to disclose their presence on the system to other users, or to participate in a class without making their presence known to other users.

In various exemplary embodiments, users can access a list of all or selected current and/or past class participants. Such lists may include performance information for such users, such as total power, speed, cadence, resistance, or a custom score that provides information about relative user performance. Such lists may also include controls to allow the user to open up live streams to the user such as live video chat streams.

System Features and User Resources

In various exemplary embodiments, the networked exercise system and methods may allow users to create accounts and save and manage their performance data. As discussed above, the system may allow users to browse schedules for upcoming live classes, signup for future live streaming classes, and setup reminders. Users may also be able to invite others to participate in a live class, and setup text, email, voice, or other notifications and calendar entries. Users may be able to access system, account, performance, and all other data via web-based or application-based interfaces for desktop and/or mobile devices, in addition to the user interface for the local system 100 associated with their stationary bike 102.

In various exemplary embodiments, the system can provide for simultaneous participation by multiple users in a recorded class, synchronized by the system and allowing access to all of the same communication and data sharing features that are available for a live class. With such a feature, the riders simultaneously participating in the same archived class can compete against each other, as well as against past performances or "ghost" riders for the same class.

Figure 16:
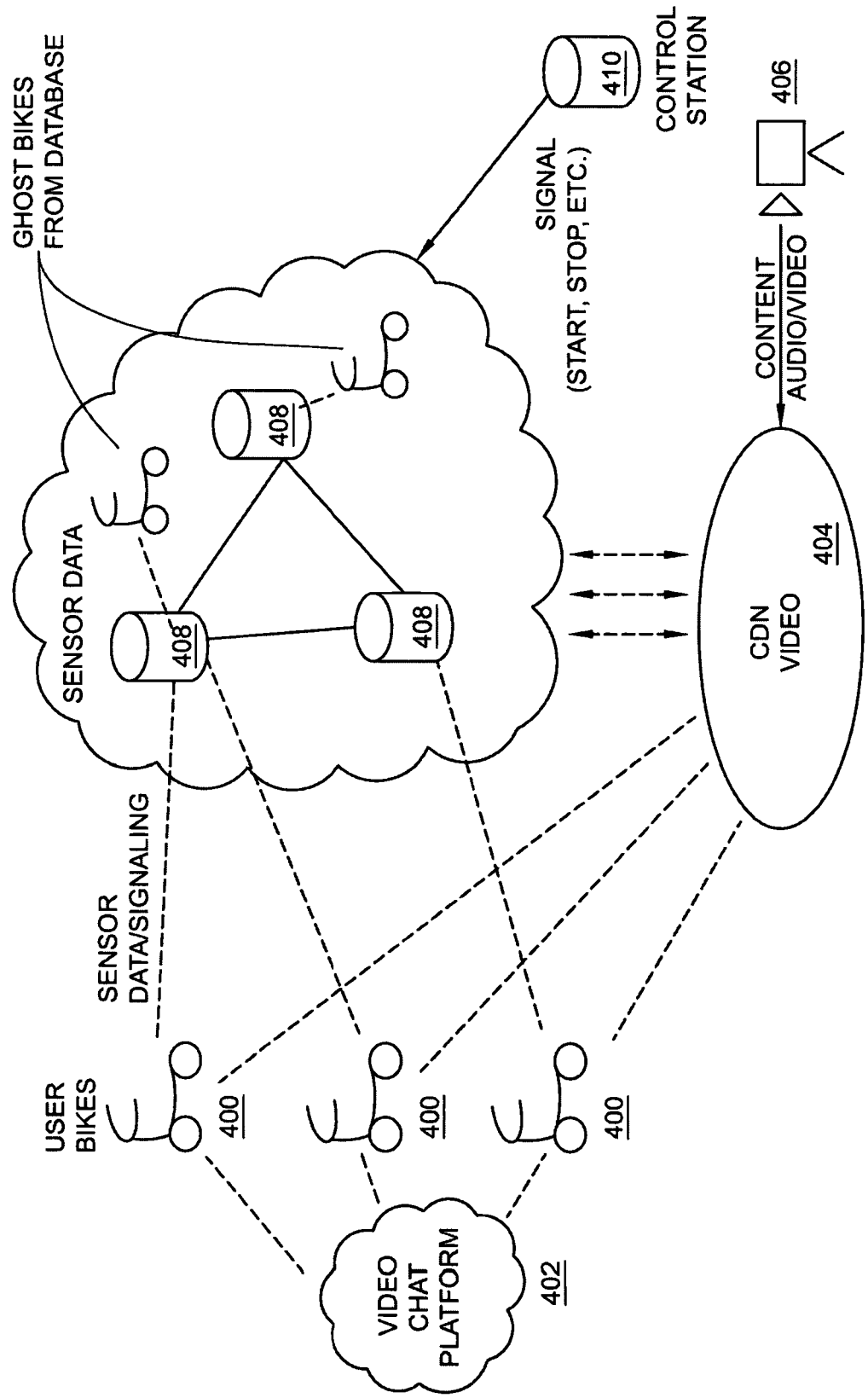
FIG. 16 is an illustration of an exemplary embodiment of a basic network architecture as disclosed herein.
Figure 17:
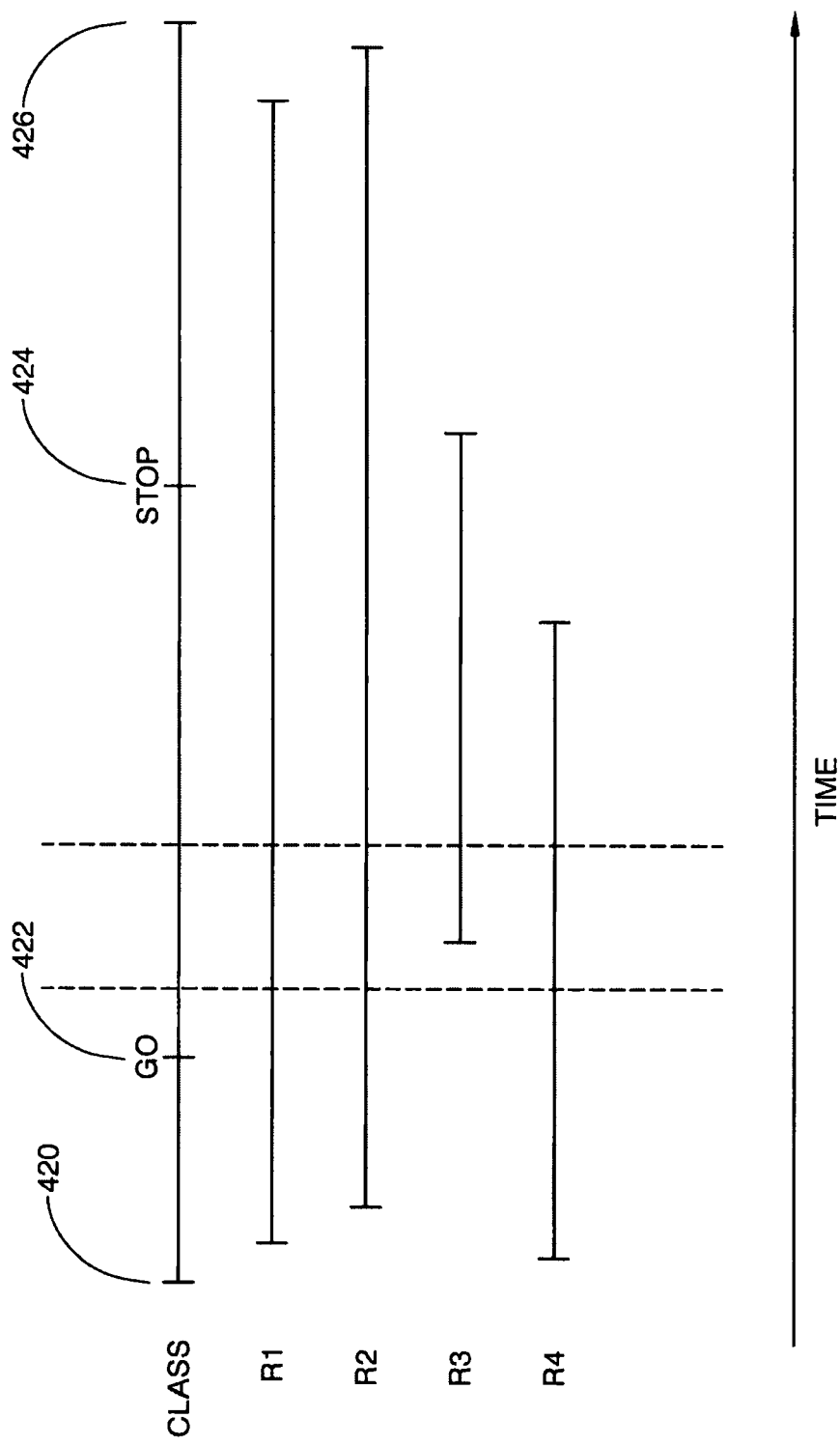
FIG. 17 is a chart showing an exemplary embodiment of a method for synchronizing data among different users participating in the same live or on-demand cycling class.

Referring to FIGS. 16-17, the system may be configured to feed synchronized live and/or archived video content and live and/or archived sensor data to users over the network. In various exemplary embodiments, the networked exercise system may be configured with a plurality of user bikes 400 in communication with a video chat platform 402, a video content distribution network 404 that receives audio video content from one or more content sources 406. The user bikes 400 may also be in communication with various other networks and servers. For example, the user bikes 400 may exchange sensor and performance data and/or signaling with various databases 408, including historical or "ghost bike" data. A control station may provide signals via the network to control the collection, storage, and management of data across the system.

One challenge for the use of comparative data from live and/or historical sources is synchronization, since some users may start riding prior to the start of the actual class, while others may join after the class has started. In order to provide accurate data regarding class performance for the leaderboard, including archived performance data, each class may have a specific "go" or start signal that serves as the starting time point for the data comparison. Archived performance data may be calibrated to the same "go" signal as live participant data, allowing for comparative data to be presented through a leaderboard or other display through the end of the class. A "stop" signal at the end of the class marks the end time point for the performance comparison for both live and archived performance data. If a rider joins the class after the "go" signal, their data can be synched correctly starting at the time they join the ride.

FIG. 17 shows various events relative to time, which is increasing from left to right on the scale at the bottom. The timeline for the class itself, whether live or archived, is shown at the top, with timelines for four different riders below it. The video being delivered for a live or archived class may begin before the actual class starts at the video start point 420. The GO signal point 422 indicates the start of the class or the class's comparison period, the STOP signal point 424 indicates the end of the class or the end of the class's comparison period, and the end video point 426 indicates the end of the video stream. For Riders 1, 2, and 4, who all start riding before the GO signal point, the GO signal serves as their starting time point for class performance metrics. For Rider 3, the point in time when they actually start will serve as their starting time point for class performance metrics. For Riders 1, 2, and 3 who continued past the STOP signal point, their end point for class performance metrics will be the STOP signal point, while the end point for Rider 4 will be the time when they actually stopped riding.

Using such a system, live and past performance (ghost bike) data for the user or other participants can be provided during a class in a range of numerical and graphical formats for comparison and competition. Live and past performance data or target performance data for the user can also be displayed simultaneously to allow users to compare their performance to a benchmark in real time during or after a class.

In various exemplary embodiments, the system may also allow users to establish handicapping systems to equalize the competition among different users or user groups allowing for broad based competitions.

In an exemplary embodiment, the system may use information provided by users to target advertising to users both during rides and during any other activities across any platforms. Advertising can be targeted based on personal data, performance characteristics, music choices, or any other data gathered by the system. For example, users that provide positive feedback about a particular music choice may be targeted for future music releases by the same or similar artists.

In various exemplary embodiments, the system may include a unique identifier on each bike to allow the system or user to track metrics on bike. This information could be used to user identification, or for maintenance, location, etc. In various exemplary embodiments, the system may also be configured to provide for closed classes. This would allow for a private instructor to work with an individual or small group, or for a group of users to ride together with or without an instructor.

In various exemplary embodiments, users can log in and/or access the system and account information via any appropriate communication technology including without limitation NFC, Bluetooth, WAN, etc. Users can also be provided with a cardkey, FOB, or other device or the stationary bike can provided with facial recognition or voice recognition technology that automatically logs the user in and accesses their account information. Users can login from their home stationary bike or from any other bike that can access the system. Thus, while traveling a user can still access their complete account history, all content, and all features from any networked stationary bike such as at a hotel, a gym, or a cycling studio in a different location.

In various exemplary embodiments, a mobile application may allow users on non-networked stationary bikes to access the system via a mobile digital device such as a tablet computer or mobile phone and access content, live streams, and other system features. The mobile device could access the system via any appropriate network using a dedicated application or browser.

In various exemplary embodiments, one or more secondary display screens may be used by the system to display class content. Using a device such as CHROMECAST or a similar integrated device to enable it to display content provided by the system through the user interface, a secondary display screen may be used to display class content or other content provided by the system. The user interface could automatically detect the availability of such an enabled device and allow the user to select the display screen for particular content.

Gamification

The interactive features of various aspects of the invention provide for a wide range of different ways to gamify the user experience. Various types of rewards and honors can be created for different achievements to create incentives for improving performance or reaching other goals.

In various exemplary embodiments, the instructor or users can create mini-competitions for participation by all users or just a selected subset of users such as a group of friends. Competitions such as sprints, hill climbs, maximum power output, etc. can be preset or created in real-time through the user interface. Winners can be rewarded with prizes such as badges, trophies, or biking specific honors such as a green or yellow jersey. Competitions can be created within a class or session, or across multiple classes or sessions like multi-stage bicycle races. A wide range of direct competitions can be created between and among users, with the different performance characteristics of different bikes calibrated and normalized to account for differences in bikes based on different riders. In various exemplary embodiments, the system provides locations or technologies to validate stationary bikes to assure that the bikes in a particular competition are properly calibrated and normalized to establish a level playing field.

Other games can be created to encourage exploration of different types of classes based on user characteristics, such as awarding badges or other honors for completion of a variety of different types of classes or classes led by different instructors.

In various exemplary embodiments the instructors, including both professional and amateur instructors, may share in the revenues generated by or attributed to their classes based on number of participants or any other metric.

What is claimed is:

1. A method, comprising:
providing, for display on a display device associated with a first exercise device, an on-demand exercise class, wherein the on-demand exercise class comprises previously recorded content and a timeline;
receiving information indicative of a first user's live activity associated with the first exercise device, the first user's live activity information being associated with first user's physical activity;
retrieving information indicative of a second user's archived activity associated with a second exercise device, the second user's archived activity information associated with second user's physical activity;
synchronizing the first user's live activity information with the second user's archived activity information;
synchronizing the timeline and the previously recorded content of the on-demand exercise class to graphically indicate a remaining time or an elapsed time in the on-demand exercise class; and
providing, for display on display device, the first user's live activity information and the second user's archived activity information as a ranked list and the timeline.

2. The method of claim 1, further comprising:
providing, for display on the display device, the previously recorded content of the on-demand exercise class together with the ranked list and the timeline.

3. The method of claim 1, further comprising:
providing, for display on the display device, together with the timeline, a first indicia graphically indicating a type of physical activity to be performed by the first user during a first portion of the on-demand exercise class.

4. The method of claim 1, further comprising:
providing, for display on the display device, together with the timeline, multiple indicia, each indicia corresponding to a physical activity to be performed by the first user during a corresponding portion of the on-demand exercise class.

5. The method of claim 1, wherein the timeline includes a plurality of time segments corresponding to different portions of the on-demand exercise class associated with physical activities performed by the first user.

6. The method of claim 5, wherein lengths of the time segments in the timeline correspond to durations of the physical activities.

7. The method of claim 1, further comprising:
updating the timeline to graphically indicate the remaining time or the elapsed time of the on-demand exercise class.

8. The method of claim 1, wherein the synchronizing the first user's live activity information with the second user's archived activity information further comprises:
synchronizing, at a control station, the first user's live activity information with the second user's archived activity information based on points in time associated with the on-demand exercise class.

9. The method of claim 8, further comprising:
synchronizing the timeline with the first user's live activity information based on the points in time; and
receiving, from the control station, at the first exercise device the first user's live activity information, the second user's archived activity information, and the timeline.

10. The method of claim 9, further comprising:
causing the display device to display the ranked list of the first user's live activity information and the second user's archived activity information, wherein the ranked list is continuously updated such that the displayed activity information compares the physical activity of the first user and the second user participating in the on-demand exercise class.

11. The method of claim 1, further comprising:
storing the first user's live activity information and the second user's archived activity information in a central database to be included as archived user activity information during a subsequent replay of the on-demand exercise class.

12. The method of claim 1, wherein the previously recorded content includes an instructor video content demonstrating how to perform at least one physical activity.

13. An exercise system, comprising:
a display coupled to a first stationary exercise device and configured to:
display a plurality of exercise classes;
in response to receiving a selection of an instructor-led exercise class from the plurality of exercise classes, receive content of the instructor-led exercise class, the content comprising video content configured to display an instructor;
display video content of the selected instructor-led exercise class;
obtain first user activity information according to points in time, wherein the first user activity information is information based on physical activity by a first user associated with movement of the first stationary exercise device;
display a timeline that indicates graphically and according to the points in time a remaining time or an elapsed time in the selected instructor-led exercise class;
receive synchronized activity information of first exercise participants that are participating in the instructor-led exercise class and second exercise participants that participated in a previous replay of the instructor-led exercise class; and
display a leaderboard, the leaderboard comprising a list that includes a correspondence between the first user and the first user activity information and a correspondence between the first and second exercise participants and the activity information of the first and second exercise participants.

14. The exercise system of claim 13, wherein the display coupled to the first stationary exercise device is further configured to:
display the timeline as time segments; and
display, at each one of the time segments, an indicia graphically indicating a type of physical activity to be performed by the first user.

15. The exercise system of claim 13, wherein the timeline includes a first segment and a second segment, the first segment indicating a first type of physical activity and the second segment indicating a second type of physical activity, and wherein the first and second types of physical activities are to be performed by the first user during the respective first and second segments of the selected instructor-led exercise class.

16. The exercise system of claim 13, wherein the display coupled to the first stationary exercise device is further configured to:
display updates to the leaderboard based on changes in the first user activity information and changes in the first and second exercise participants' activity information.

17. The exercise system of claim 13, wherein the first stationary exercise device comprises a first treadmill and the instructor-led exercise class comprises receiving indications of an instructor running on a moving belt of a second treadmill during a portion of the instructor-led exercise class.

18. The exercise system of claim 13, wherein the display coupled to the first stationary exercise device is further configured to:
display updates to the timeline to graphically indicate the remaining time or the elapsed time of the instructor-led exercise class.

19. A non-transitory computer-readable medium storing instructions thereon, which when executed by a processor cause the processor to perform operations, the operations comprising:
providing to a display associated with an exercise device, content of an exercise class and a timeline, wherein the timeline comprises time segments corresponding to different portions of the exercise class associated with different types of physical activity to be performed by a user;
receiving information indicative of the user's live activity associated with the exercise device, the information being associated with the user's physical activity;
synchronizing the information indicative of the user's live activity with archived information indicative of other users' activity that participated in a previous replay of the exercise class;
providing updates to the timeline to graphically indicate a remaining time or an elapsed time for at least one of the time segments in the exercise class; and
providing, during at least part of a duration of the exercise class, the information indicative of the user's live activity and the archived information indicative of other users' activity to be presented on the display as an updating ranked list together with the updates to the timeline.

20. The non-transitory computer-readable medium of claim 19, wherein the operations further comprise:
causing indicia to be displayed on the display along at least one of the time segments, wherein the indicia graphically indicates the types of physical activity to be performed by the user.

* * * * *

UNITED STATES PATENT AND TRADEMARK OFFICE
CERTIFICATE OF CORRECTION

PATENT NO. : 12,249,413 B2
APPLICATION NO. : 18/586390
DATED : March 11, 2025
INVENTOR(S) : John Paul Foley et al.

Page 1 of 2

It is certified that error appears in the above-identified patent and that said Letters Patent is hereby corrected as shown below:

In the Specification

In the RELATED APPLICATIONS:

Column 1, Line 7 change "U.S. patent application Ser. No." to --U.S. Patent Application No.--.

Column 1, Lines 8-9 change "U.S. patent application Ser. No." to --U.S. Patent Application No.--.

Column 1, Line 11 change "U.S. patent application Ser. No." to --U.S. Patent Application No.--.

Column 1, Line 14 change "U.S. patent application Ser. No." to --U.S. Patent Application No.--.

Column 1, Line 17 change "U.S. patent application Ser. No." to --U.S. Patent Application No.--.

Column 1, Line 20 change "U.S. patent application Ser. No." to --U.S. Patent Application No.--.

Column 1, Lines 22-23 change "U.S. patent application Ser. No." to --U.S. Patent Application No.--.

Column 1, Lines 25-26 change "U.S. patent application Ser. No." to --U.S. Patent Application No.--.

Column 1, Lines 27-28 change "U.S. patent application Ser. No." to --U.S. Patent Application No.--.

Column 1, Line 31 change "U.S. patent application Ser. No." to --U.S. Patent Application No.--.

Column 1, Line 34 change "U.S. patent application Ser. No." to --U.S. Patent Application No.--.

Column 1, Line 37 change "U.S. patent application Ser. No." to --U.S. Patent Application No.--.

Column 1, Line 40 change "U.S. patent application Ser. No." to --U.S. Patent Application No.--.

Signed and Sealed this
Thirteenth Day of May, 2025

Coke Morgan Stewart
*Acting Director of the United States Patent and Trademark Office*

CERTIFICATE OF CORRECTION (continued)
U.S. Pat. No. 12,249,413 B2

Column 1, Line 48 change "U.S. patent application Ser. No." to --U.S. Patent Application No.--.

Column 1, Lines 55-56 change "U.S. patent application Ser. No." to --U.S. Patent Application No.--.

Column 1, Line 59 change "U.S. patent application Ser. No." to --U.S. Patent Application No.--.

Column 1, Line 62 change "U.S. patent application Ser. No." to --U.S. Patent Application No.--.

Column 10, Line 65 change "case of use and" to --ease of use and--.